(12) United States Patent
Jung et al.

(10) Patent No.: US 12,058,931 B2
(45) Date of Patent: Aug. 6, 2024

(54) HETEROCYCLIC COMPOUND AND ORGANIC LIGHT EMITTING DEVICE COMPRISING SAME

(71) Applicant: LG CHEM, LTD., Seoul (KR)

(72) Inventors: Min Woo Jung, Daejeon (KR); Dong Hoon Lee, Daejeon (KR); Boon Jae Jang, Daejeon (KR); Sang Duk Suh, Daejeon (KR); Jungha Lee, Daejeon (KR); Su Jin Han, Daejeon (KR); Seulchan Park, Daejeon (KR); Sunghyun Hwang, Daejeon (KR)

(73) Assignee: LG CHEM, LTD., Seoul (KR)

( * ) Notice: Subject to any disclaimer, the term of this patent is extended or adjusted under 35 U.S.C. 154(b) by 708 days.

(21) Appl. No.: 17/264,627

(22) PCT Filed: Nov. 6, 2019

(86) PCT No.: PCT/KR2019/014993
§ 371 (c)(1),
(2) Date: Jan. 29, 2021

(87) PCT Pub. No.: WO2020/096351
PCT Pub. Date: May 14, 2020

(65) Prior Publication Data
US 2021/0320260 A1    Oct. 14, 2021

(30) Foreign Application Priority Data

Nov. 6, 2018 (KR) ...................... 10-2018-0135443
Nov. 6, 2019 (KR) ...................... 10-2019-0140737

(51) Int. Cl.
*H10K 85/60* (2023.01)
*C07D 405/14* (2006.01)
(Continued)

(52) U.S. Cl.
CPC ......... *H10K 85/654* (2023.02); *C07D 405/14* (2013.01); *C07D 409/14* (2013.01);
(Continued)

(58) Field of Classification Search
CPC ............ H10K 85/654; H10K 85/6574; C07D 405/14; C07D 409/14
See application file for complete search history.

(56) References Cited

U.S. PATENT DOCUMENTS

2004/0251816 A1    12/2004  Leo et al.
2019/0013490 A1    1/2019   Cho et al.
(Continued)

FOREIGN PATENT DOCUMENTS

KR    10-2000-0051826 A    8/2000
KR    10-2016-0027940 A    3/2016
(Continued)

OTHER PUBLICATIONS

Partial machine translation of KR 20190001116 (generated Sep. 17, 2023).*

(Continued)

*Primary Examiner* — Kregg T Brooks
(74) *Attorney, Agent, or Firm* — Bryan Cave Leighton Paisner LLP

(57) ABSTRACT

A heterocyclic compound represented by Chemical Formula 1 and an organic light emitting device comprising the same, and the heterocyclic compound providing improved efficiency, low driving voltage, and improved lifetime characteristics of the organic light emitting device.

(Continued)

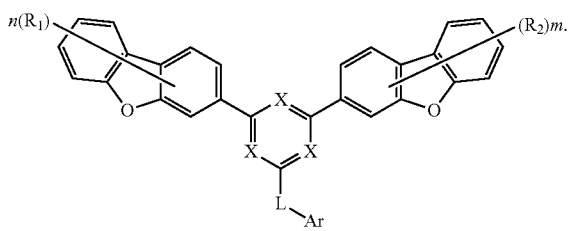

8 Claims, 1 Drawing Sheet

(51) Int. Cl.
  *C07D 409/14* (2006.01)
  *C07F 7/08* (2006.01)
  *C09K 11/06* (2006.01)
  *H10K 50/11* (2023.01)
  *H10K 85/40* (2023.01)
  *H10K 101/10* (2023.01)

(52) U.S. Cl.
  CPC ............ *C07F 7/0812* (2013.01); *C09K 11/06* (2013.01); *H10K 85/40* (2023.02); *H10K 85/6572* (2023.02); *H10K 85/6574* (2023.02); *H10K 85/6576* (2023.02); *C09K 2211/1018* (2013.01); *H10K 50/11* (2023.02); *H10K 2101/10* (2023.02)

(56) References Cited

U.S. PATENT DOCUMENTS

| | | |
|---|---|---|
| 2019/0165280 A1 | 5/2019 | Jang et al. |
| 2019/0181351 A1 | 7/2019 | Jang et al. |
| 2019/0245149 A1 | 8/2019 | Heo et al. |
| 2020/0251659 A1 | 8/2020 | Lee et al. |
| 2020/0388766 A1* | 12/2020 | Kim .................. H10K 85/342 |

FOREIGN PATENT DOCUMENTS

| | | |
|---|---|---|
| KR | 10-2017-0113320 A | 10/2017 |
| KR | 10-2017-0113397 A | 10/2017 |
| KR | 10-2018-0002351 A | 1/2018 |
| KR | 10-2018-0013449 A | 2/2018 |
| KR | 10-1847347 B1 | 4/2018 |
| KR | 10-2018-0055679 A | 5/2018 |
| KR | 10-1857703 B1 | 5/2018 |
| KR | 10-2018-0061074 A | 6/2018 |
| KR | 10-2018-0086126 A | 7/2018 |
| KR | 10-2018-0112962 A | 10/2018 |
| KR | 20190001116 A * | 1/2019 |
| WO | 2003/012890 A2 | 2/2003 |

OTHER PUBLICATIONS

Partial machine translation of KR 20180112962 (generated Sep. 17, 2023).*

* cited by examiner

[FIG. 1]
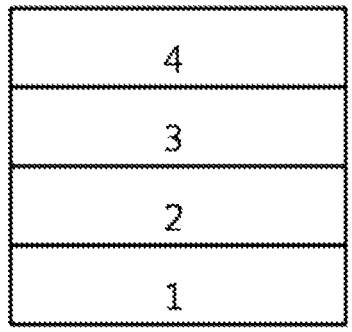
[FIG. 2]
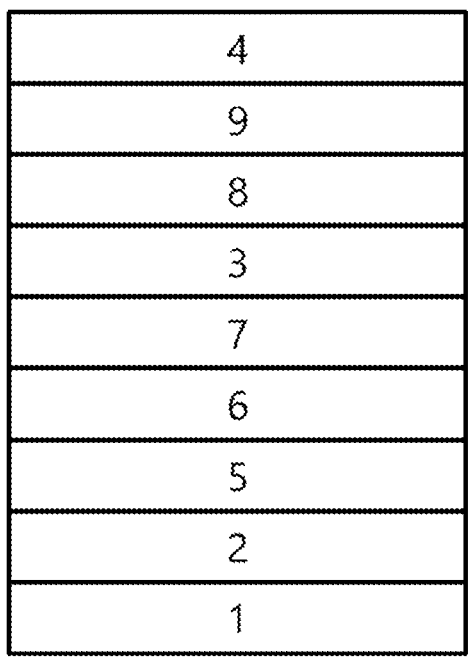

HETEROCYCLIC COMPOUND AND ORGANIC LIGHT EMITTING DEVICE COMPRISING SAME

CROSS-REFERENCE TO RELATED APPLICATION(S)

This application is a National Stage Application of International Application No. PCT/KR2019/014993 filed on Nov. 6, 2019, which claims priority to Korean Patent Application No. 10-2018-0135443 filed on Nov. 6, 2018 and Korean Patent Application No. 10-2019-0140737 filed on Nov. 6, 2019, the disclosures of which are incorporated herein by reference in their entireties.

TECHNICAL FIELD

The present disclosure relates to a novel compound and an organic light emitting device comprising the same.

BACKGROUND

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies are being conducted thereon.

The organic light emitting device generally has a structure which comprises an anode, a cathode, and an organic material layer interposed between the anode and the cathode. The organic material layer frequently has a multilayered structure that comprises different materials in order to enhance efficiency and stability of the organic light emitting device, and for example, the organic material layer may be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

There is a continuing need for the development of new materials for the organic materials used in the organic light emitting devices as described above.

RELATED ARTS (Patent Literature 0001) Korean Unexamined Patent Publication No. 10-2000-0051826

DETAILED DESCRIPTION

Technical Problem

It is an object of the present disclosure to provide a novel compound and an organic light emitting device comprising the same.

Technical Solution

According to one embodiment of the present disclosure, there is provided a compound represented by the following Chemical Formula 1:

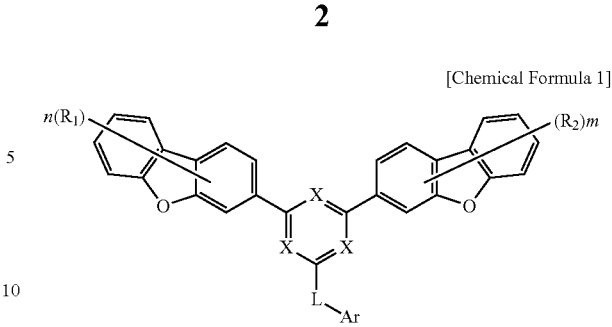

[Chemical Formula 1]

in Chemical Formula 1,

X is each independently N or CH, and at least one of X is N, n and m are each independently an integer of 0 to 3, and the sum of n and m is 1 or more, $R_1$ and $R_2$ are each independently a substituted or unsubstituted $C_{6-10}$ aryl, L is a substituted or unsubstituted $C_{6-60}$ arylene, and Ar is a substituted or unsubstituted $C_{5-60}$ heteroaryl containing any one or more heteroatoms selected from the group consisting of N, O and S, or tri($C_{6-60}$ aryl)silyl.

According to another aspect of the present disclosure, there is provided an organic light emitting device comprising: a first electrode; a second electrode that is provided to face the first electrode; and one or more organic material layers that are provided between the first electrode and the second electrode, wherein one or more layers of the organic material layers include a compound represented by Chemical Formula 1.

Advantageous Effects

The above-mentioned compound represented by Chemical Formula 1 can be used as a material of an organic material layer of an organic light emitting device, and can improve the efficiency, achieve low driving voltage and/or improve lifetime characteristics in the organic light emitting device. In particular, the compound represented by the Chemical Formula 1 may be used as a hole injection material, hole transport material, hole injection and transport material, light emitting material, electron transport material, or electron injection material.

BRIEF DESCRIPTION OF THE DRAWINGS

FIG. 1 depicts an example of an organic light emitting device comprising a substrate 1, an anode 2, a light emitting layer 3, and a cathode 4.

FIG. 2 depicts an example of an organic light emitting device comprising a substrate 1, an anode 2, a hole injection layer 5, a hole transport layer 6, an electron blocking layer 7, a light emitting layer 3, an electron transport layer 8, an electron injection layer 9 and a cathode 4.

DETAILED DESCRIPTION

Hereinafter, embodiments of the present disclosure will be described in more detail to facilitate understanding of the invention.

The present disclosure provides the compound represented by Chemical Formula 1.

As used herein, the notation ⊢, ⊣ or ╎ means a bond linked to another substituent group.

As used herein, the term "substituted or unsubstituted" means being unsubstituted or substituted with one or more substituents selected from the group consisting of deuterium; a halogen group; a cyano group; a nitro group; a hydroxy group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a heterocyclic group containing at least one of N, O and S atoms, or being unsubstituted or substituted with a substituent to which two or more substituents of the above-exemplified substituents are connected. For example, "a substituent in which two or more substituents are connected" may be a biphenyl group. Namely, a biphenyl group may be an aryl group, or it may also be interpreted as a substituent in which two phenyl groups are connected.

In the present disclosure, the carbon number of a carbonyl group is not particularly limited, but is preferably 1 to 40. Specifically, the carbonyl group may be a compound having the following structural formulas, but is not limited thereto:

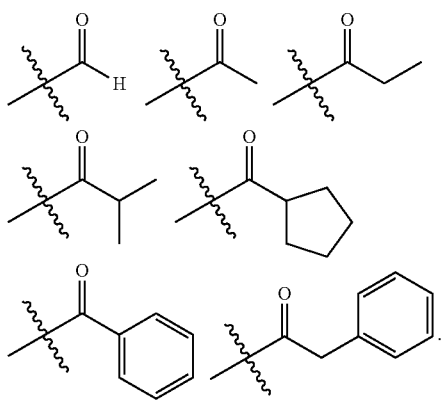

In the present disclosure, an ester group may have a structure in which oxygen of the ester group may be substituted by a straight-chain, branched-chain, or cyclic alkyl group having 1 to 25 carbon atoms, or an aryl group having 6 to 25 carbon atoms. Specifically, the ester group may be a compound having the following structural formulas, but is not limited thereto:

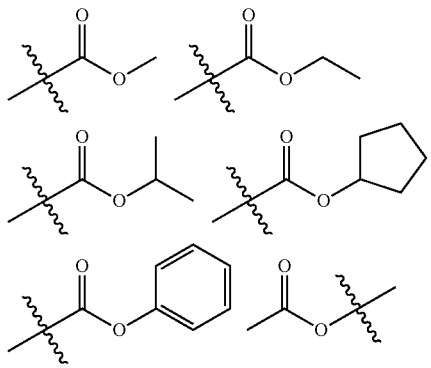

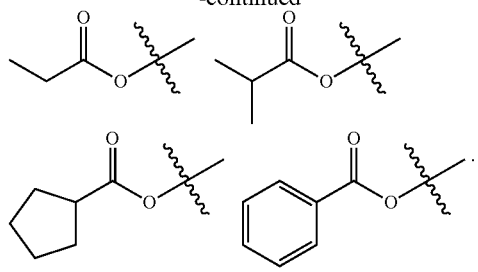

In the present disclosure, the carbon number of an imide group is not particularly limited, but is preferably 1 to 25. Specifically, the imide group may be a compound having the following structural formulas, but is not limited thereto:

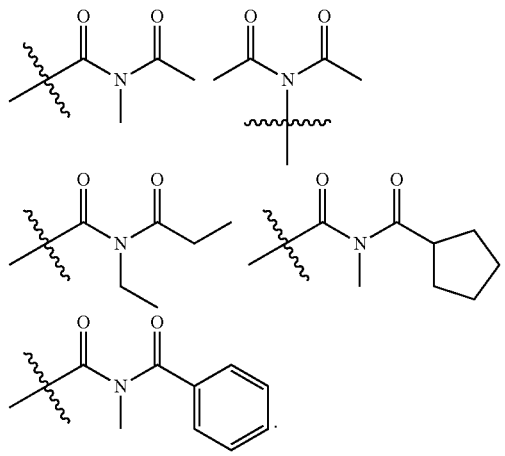

In the present disclosure, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but is not limited thereto.

In the present disclosure, a boron group specifically includes a trimethylboron group, a triethylboron group, a t-butyldimethylboron group, a triphenylboron group, and a phenylboron group, but is not limited thereto.

In the present disclosure, examples of a halogen group include fluorine, chlorine, bromine, or iodine.

In the present disclosure, the alkyl group may be straight-chain or branched-chain, and the carbon number thereof is not particularly limited, but is preferably 1 to 40. According to one embodiment, the carbon number of the alkyl group is 1 to 20. According to another embodiment, the carbon number of the alkyl group is 1 to 10. According to another embodiment, the carbon number of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present disclosure, the alkenyl group may be straight-chain or branched-chain, and the carbon number thereof is not particularly limited, but is preferably 2 to 40. According to one embodiment, the carbon number of the alkenyl group is 2 to 20. According to another embodiment, the carbon number of the alkenyl group is 2 to 10. According to still another embodiment, the carbon number of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present disclosure, a cycloalkyl group is not particularly limited, but the carbon number thereof is preferably 3 to 60. According to one embodiment, the carbon number of the cycloalkyl group is 3 to 30. According to another embodiment, the carbon number of the cycloalkyl group is 3 to 20. According to still another embodiment, the carbon number of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present disclosure, an aryl group is not particularly limited, but the carbon number thereof is preferably 6 to 60, and it may be a monocyclic aryl group or a polycyclic aryl group. According to one embodiment, the carbon number of the aryl group is 6 to 30. According to one embodiment, the carbon number of the aryl group is 6 to 20. The aryl group may be a phenyl group, a biphenyl group, a terphenyl group or the like as the monocyclic aryl group, but is not limited thereto.

The polycyclic aryl group includes a naphthyl group, an anthracenyl group, a phenanthryl group, a pyrenyl group, a perylenyl group, a chrysenyl group, or the like, but is not limited thereto.

In the present disclosure, the fluorenyl group may be substituted, and two substituents may be linked with each other to form a spiro structure. In the case where the fluorenyl group is substituted,

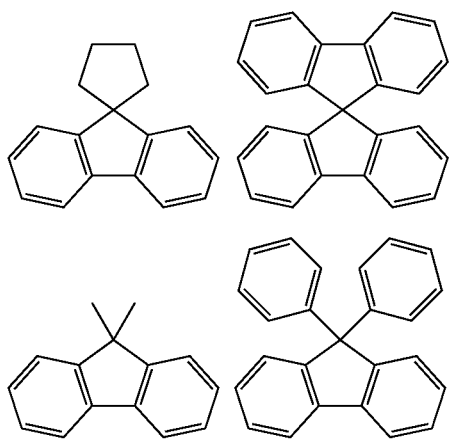

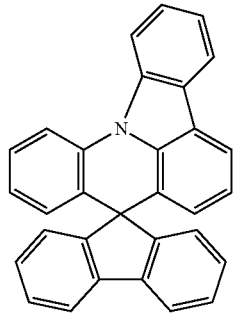

and the like can be formed. However, the structure is not limited thereto.

In the present disclosure, a heterocyclic group is a heterocyclic group containing one or more of O, N, Si and S as a heteroatom, and the carbon number thereof is not particularly limited, but is preferably 2 to 60. Examples of the heterocyclic group include a thiophene group, a furan group, a pyrrole group, an imidazole group, a thiazole group, an oxazol group, an oxadiazol group, a triazol group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzoimidazole group, a benzothiazol group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present disclosure, the aryl group in the aralkyl group, the aralkenyl group, the alkylaryl group, the arylamine group and the arylsily group is the same as the aforementioned examples of the aryl group. In the present disclosure, the alkyl group in the aralkyl group, the alkylaryl group and the alkylamine group is the same as the aforementioned examples of the alkyl group. In the present disclosure, the heterocyclic group in the heteroarylamine can be applied to the aforementioned description of the heteroaryl group. In the present disclosure, the alkenyl group in the aralkenyl group is the same as the aforementioned examples of the alkenyl group.

In the present disclosure, the aforementioned description of the aryl group may be applied except that the arylene is a divalent group. In the present disclosure, the aforementioned description of the heterocyclic group can be applied except that the heteroarylene is a divalent group. In the present disclosure, the aforementioned description of the aryl group or cycloalkyl group can be applied except that the hydrocarbon ring is not a monovalent group but formed by combining two substituent groups. In the present disclosure, the aforementioned description of the heterocyclic group can be applied, except that the heterocyclic group is not a monovalent group but formed by combining two substituent groups.

Preferably, the Chemical Formulas 1 may be the following Chemical Formulas 1-1:

[Chemical Formula 1-1]

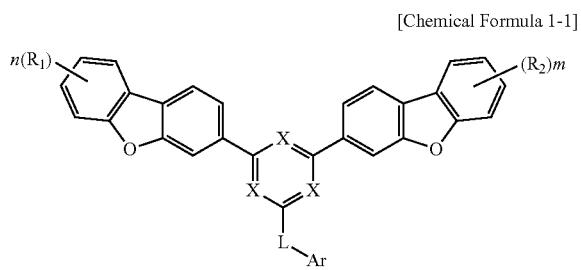

in Chemical Formula 1-1,

X, L, Ar, $R_1$, $R_2$, n and m are the same as defined above.

Preferably, the sum of n and m may be 1 or 2, and more preferably the sum of n and m may be 1.

Preferably, $R_1$ and $R_2$ may be phenyl.

Preferably, all of X may be N.

Preferably, L may be a substituted or unsubstituted $C_{6-20}$ arylene, more preferably phenylene.

Preferably, Ar may be any one selected from the group consisting of:

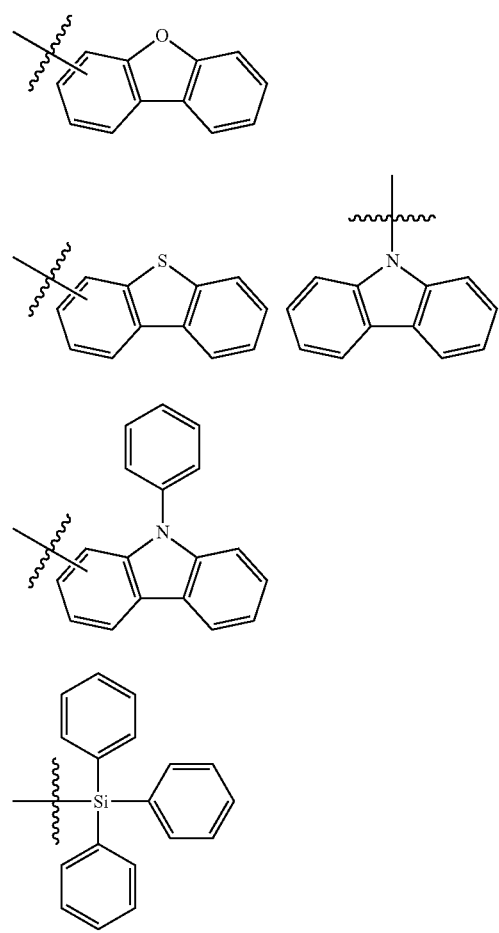

For example, the compound may be selected from the group consisting of the following compounds:

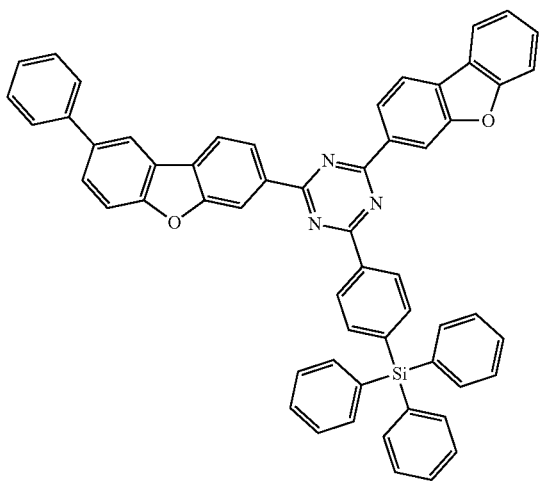

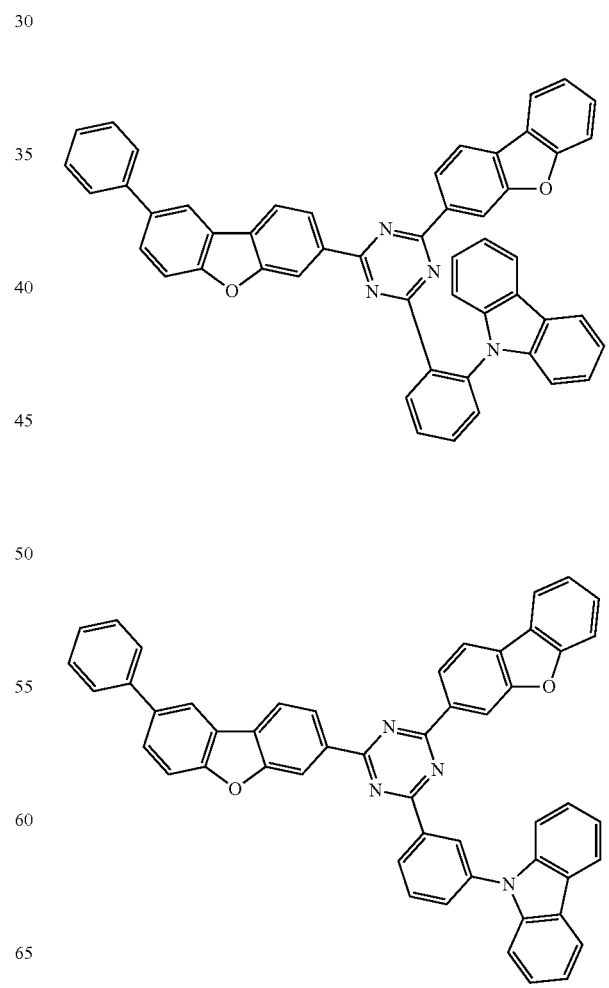

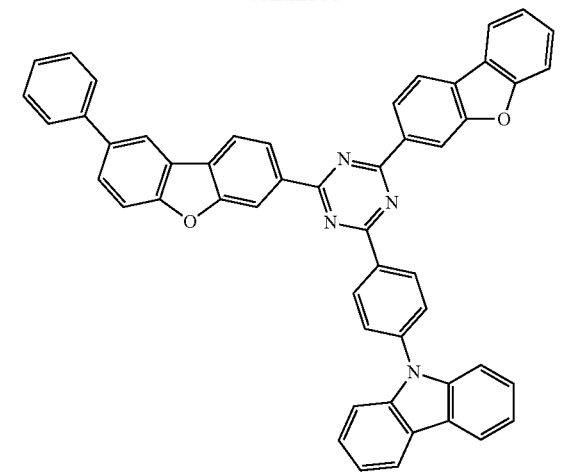
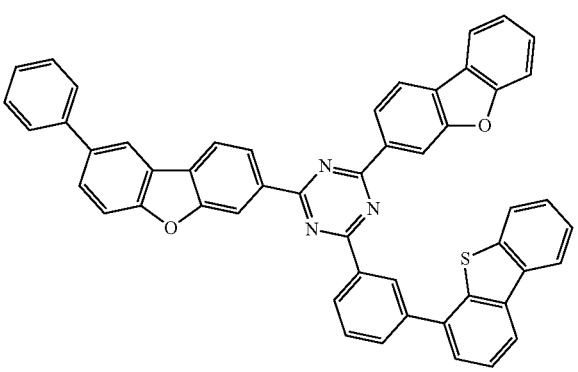
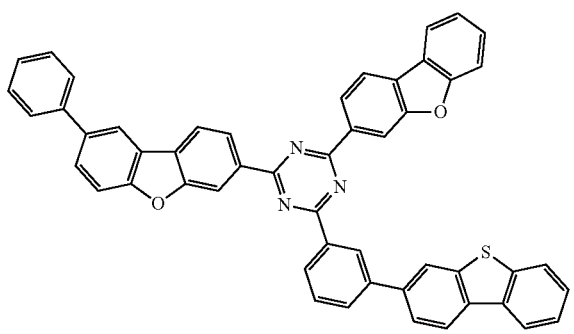
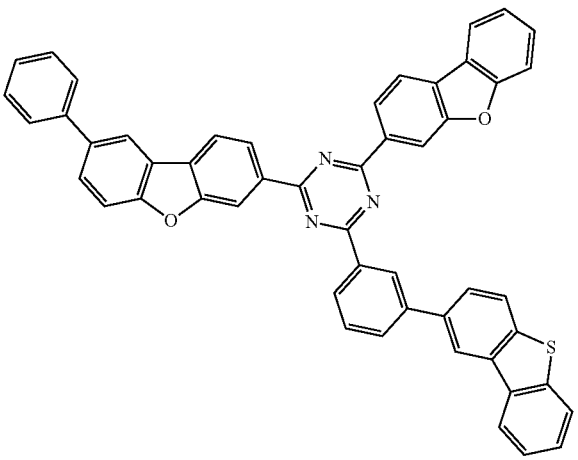
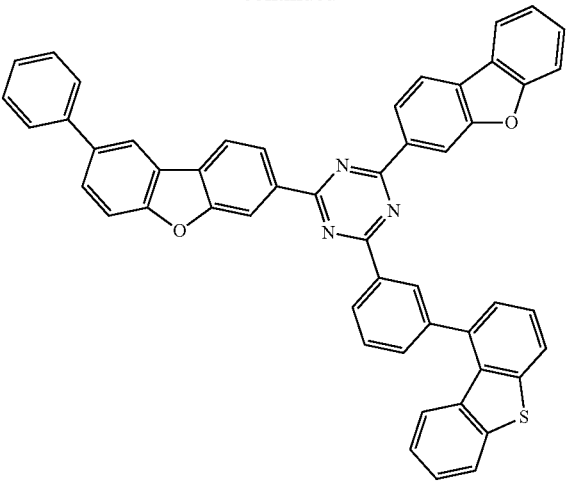
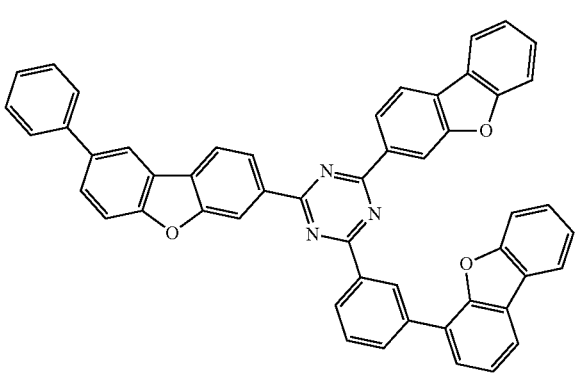
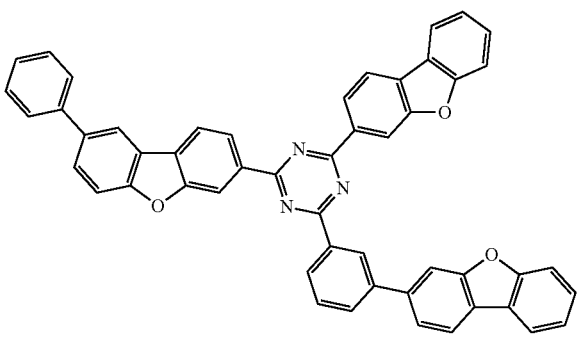
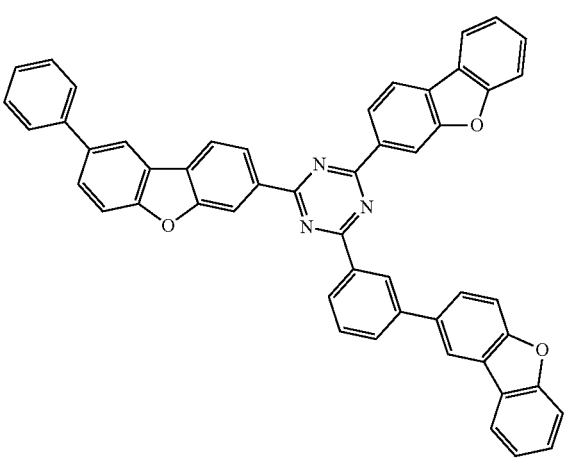

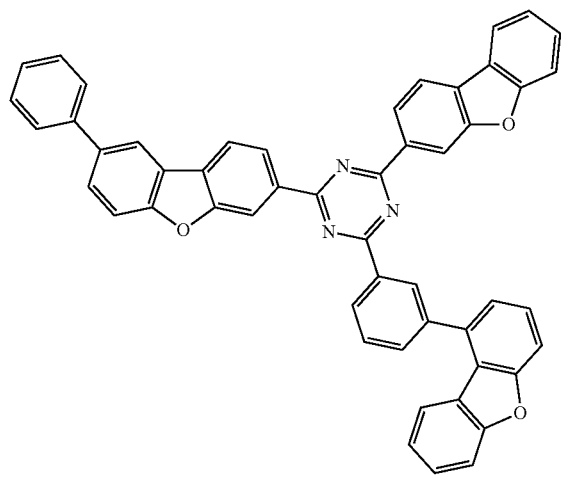
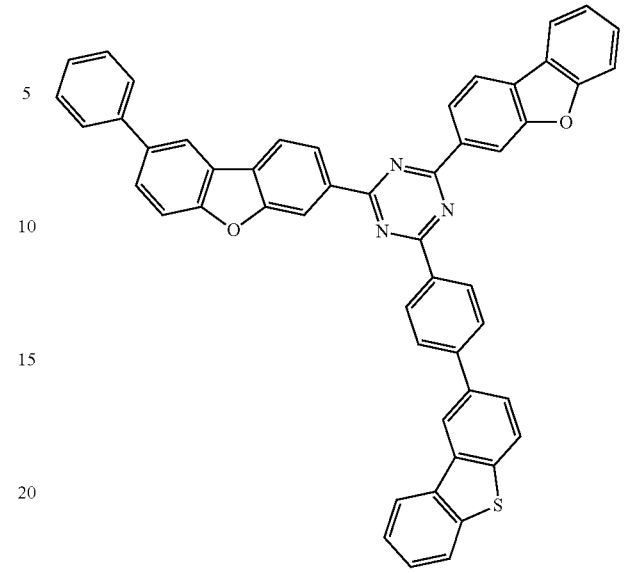
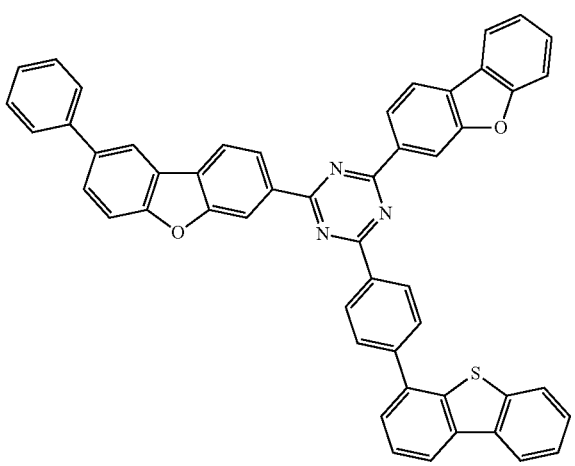
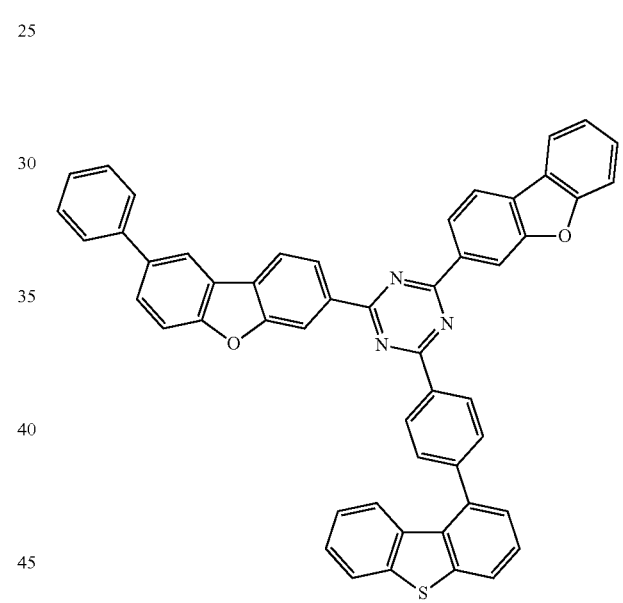
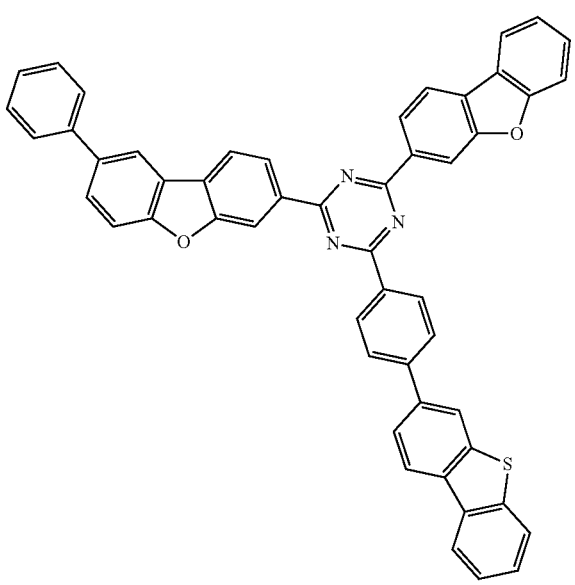
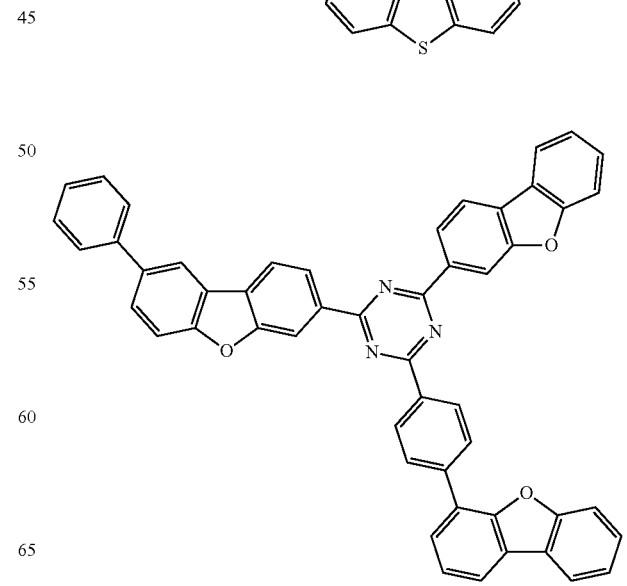

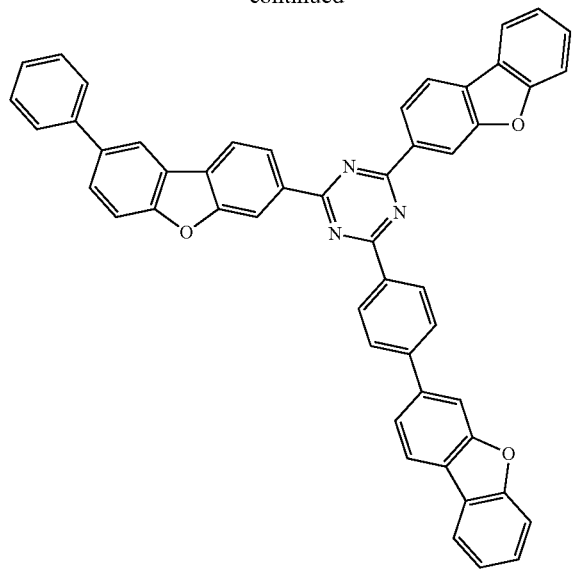
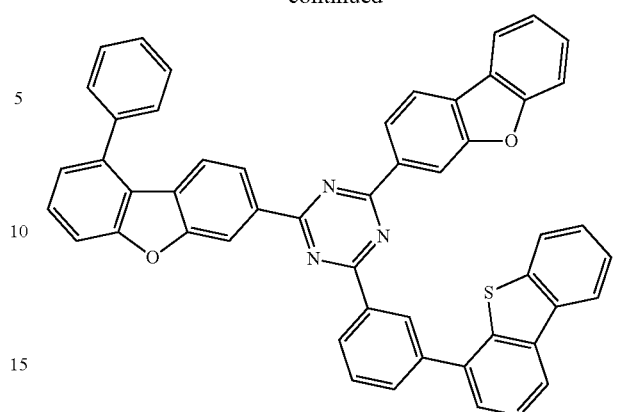
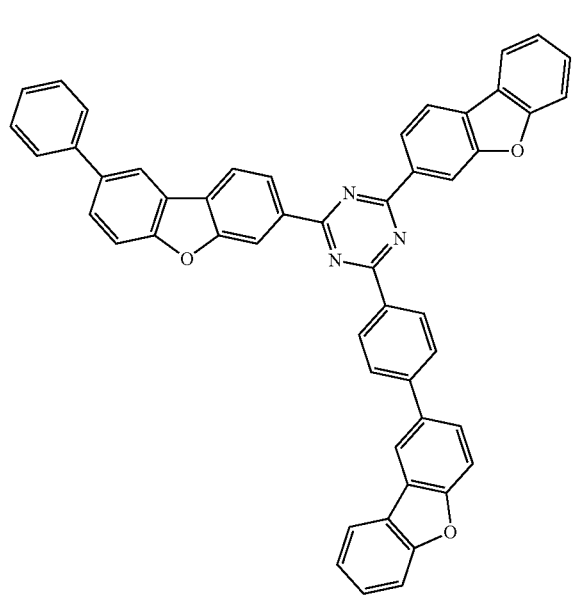
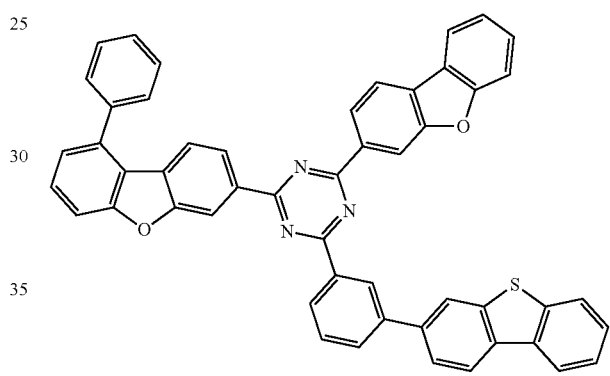
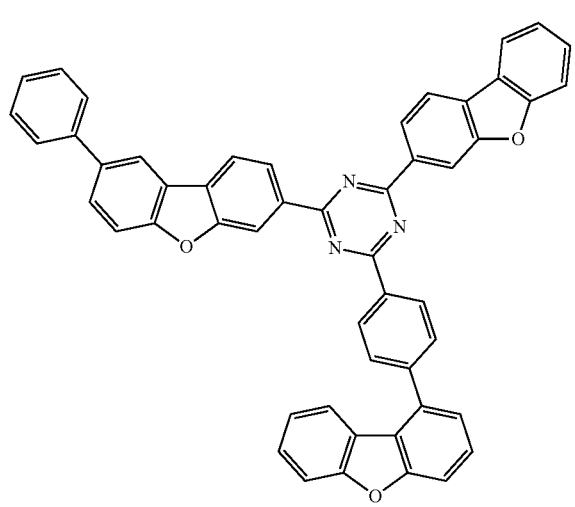
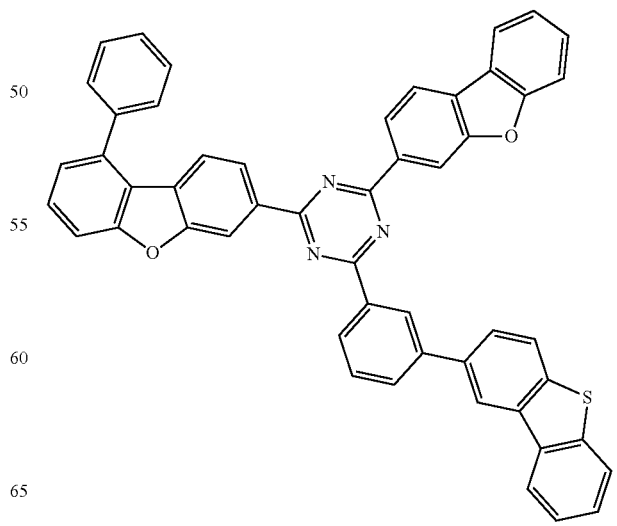

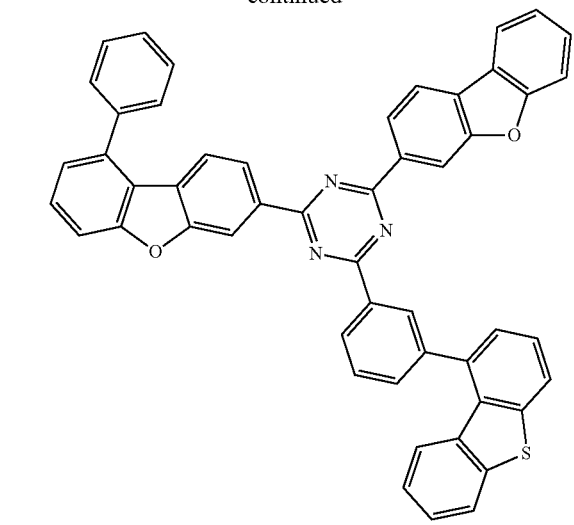
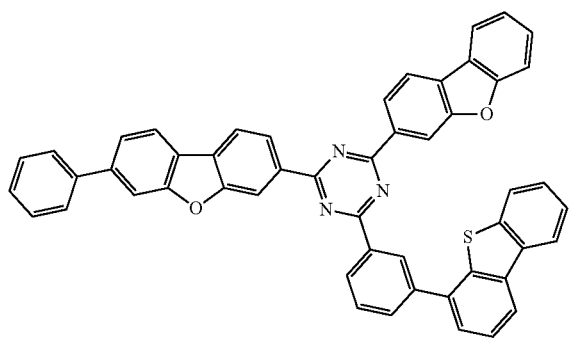
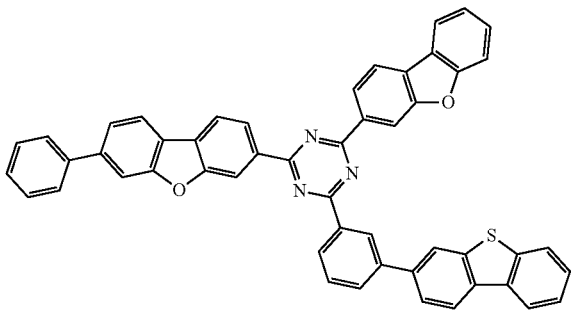
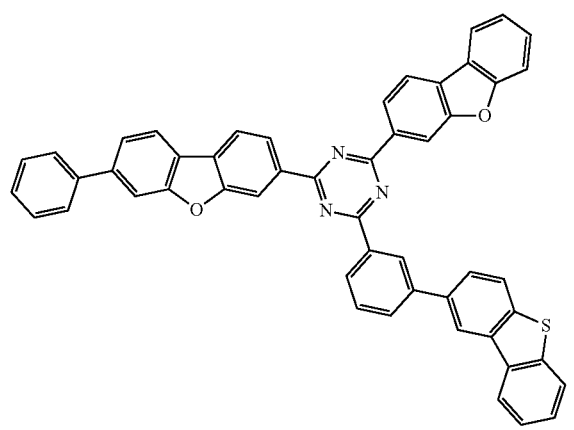
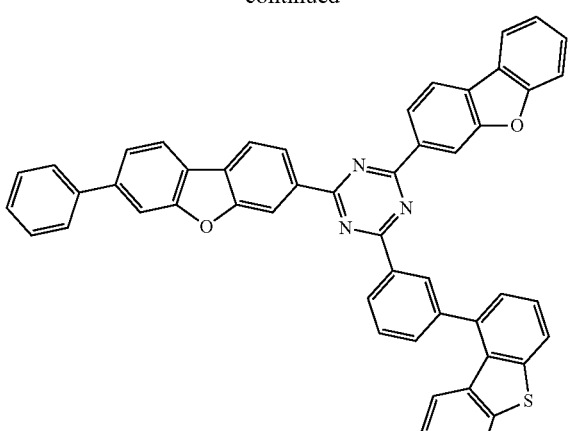
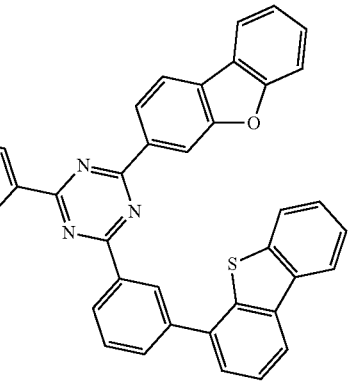
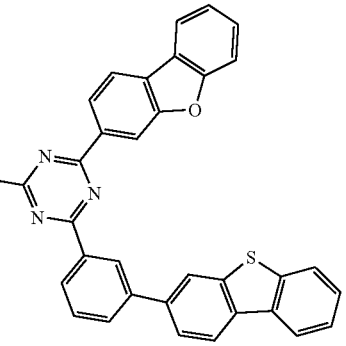
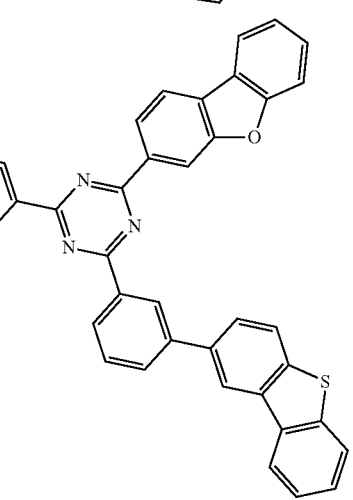

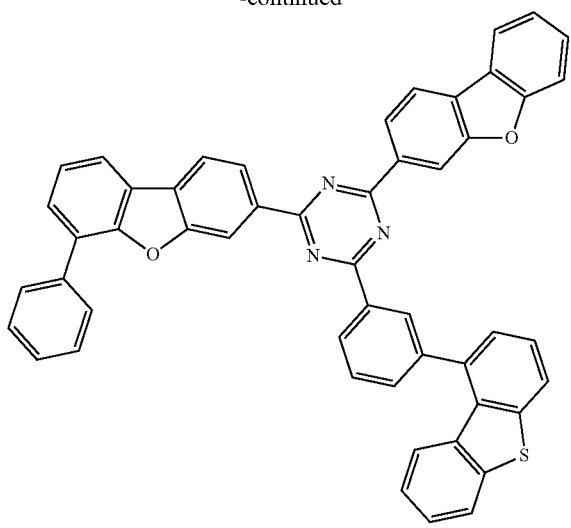
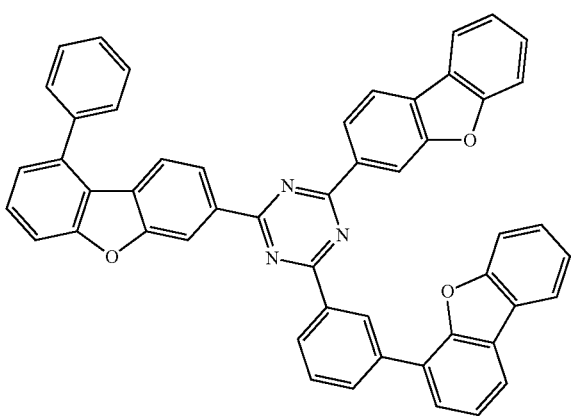
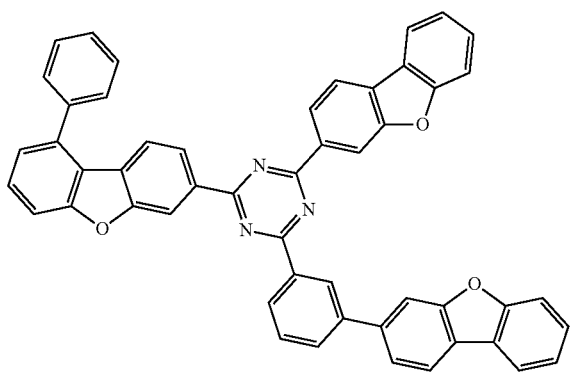
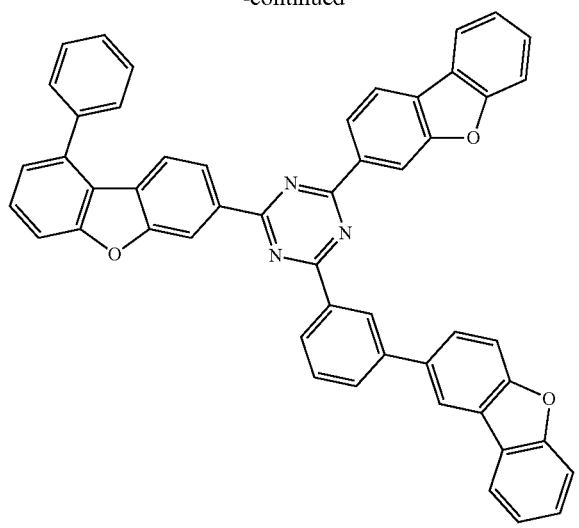
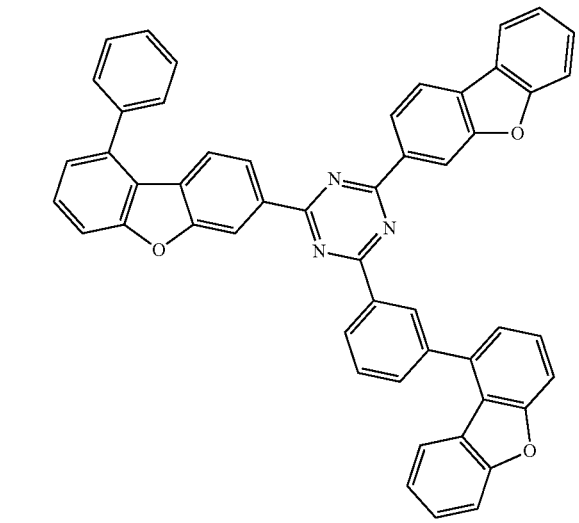
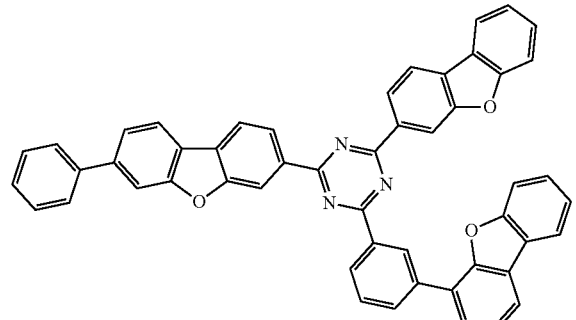
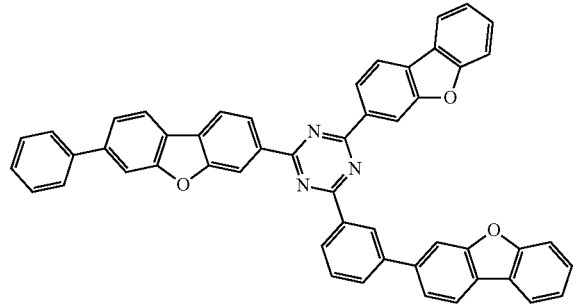

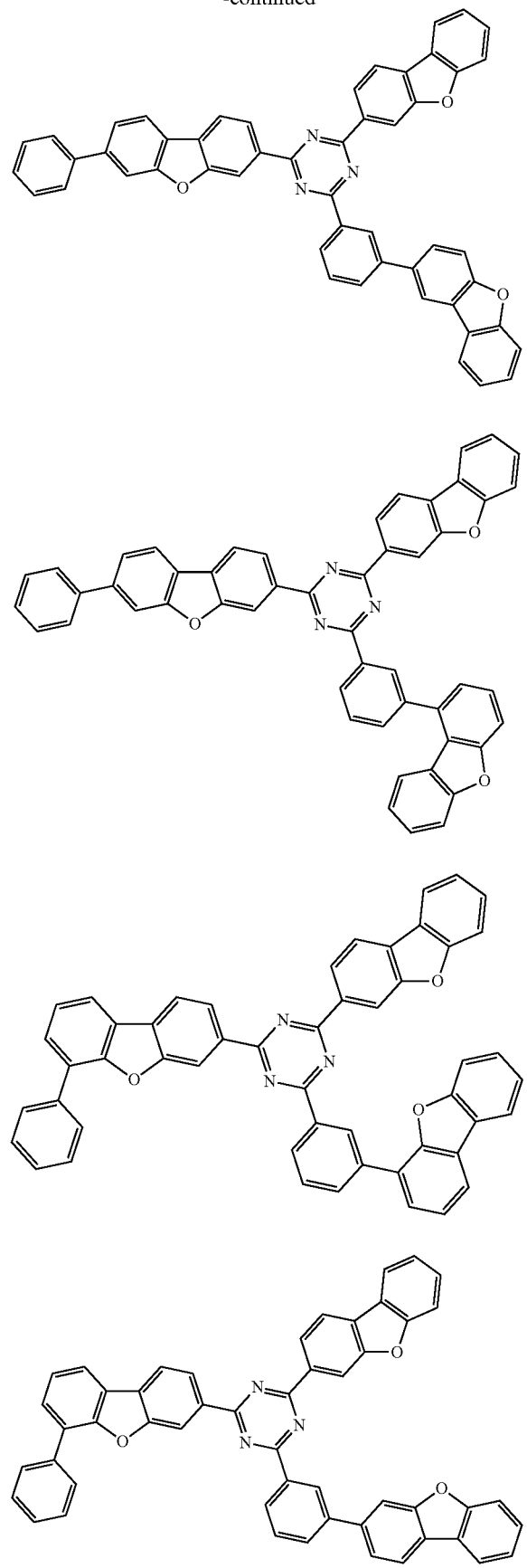
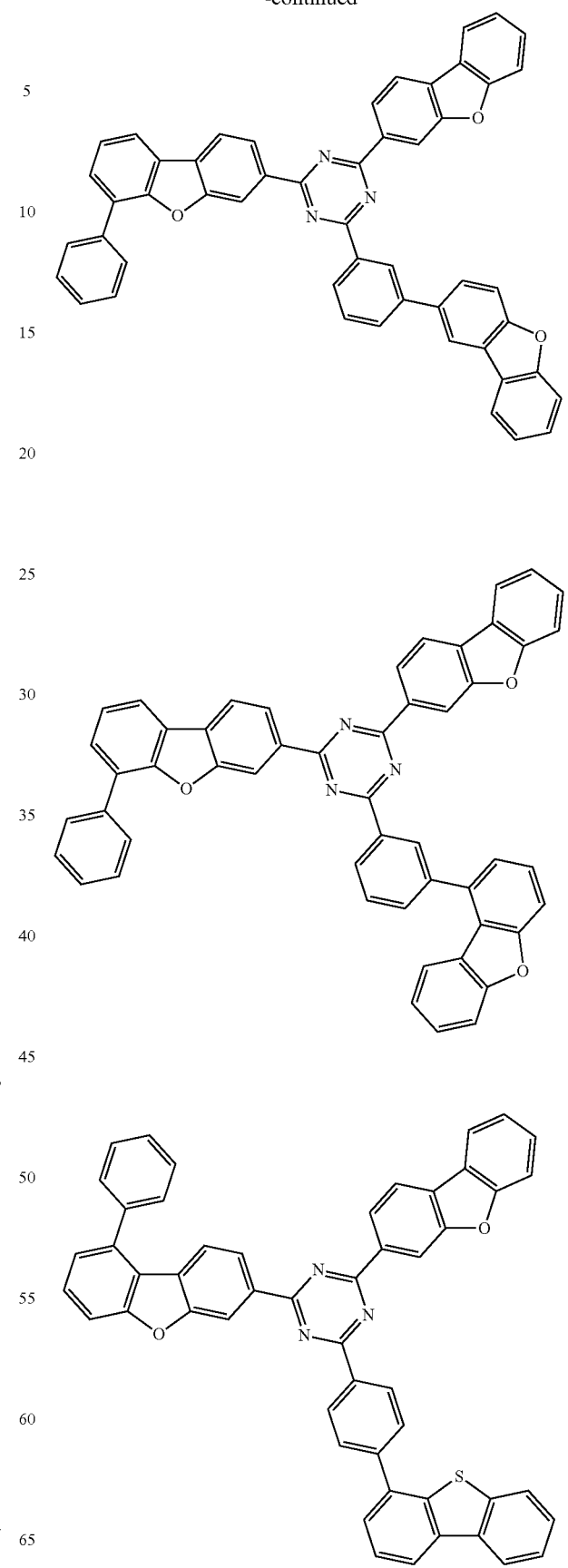

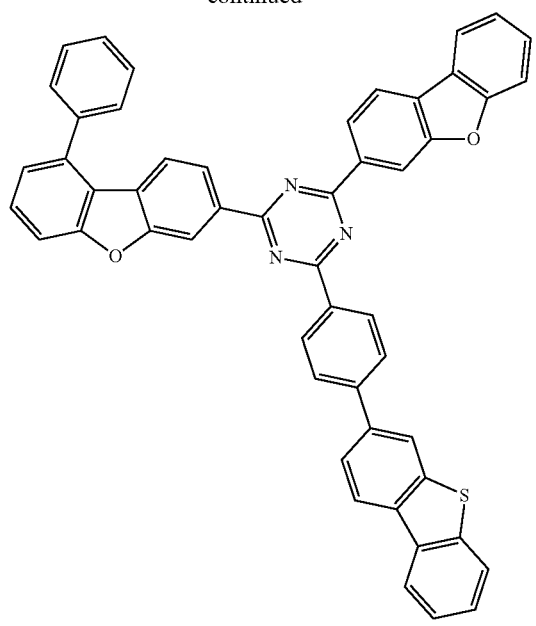
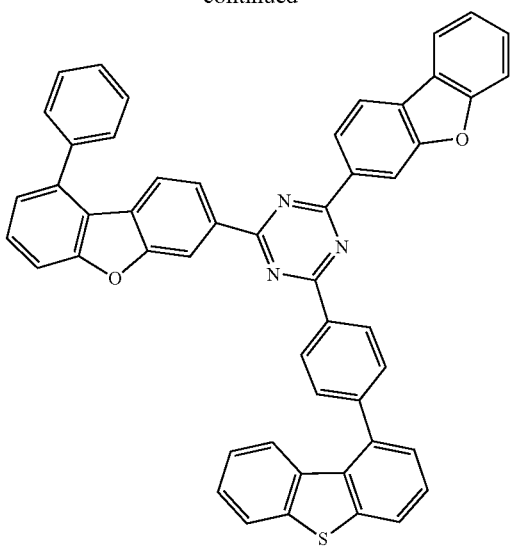
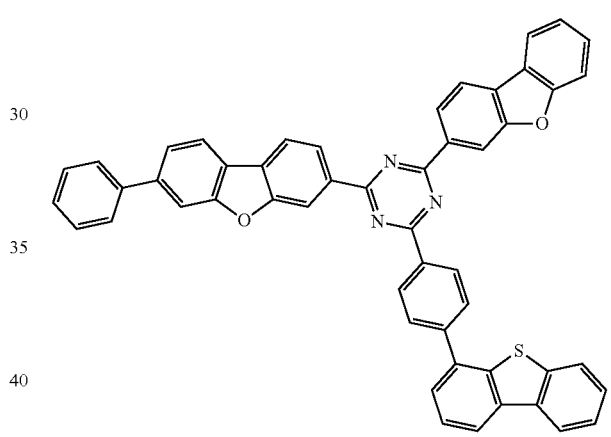
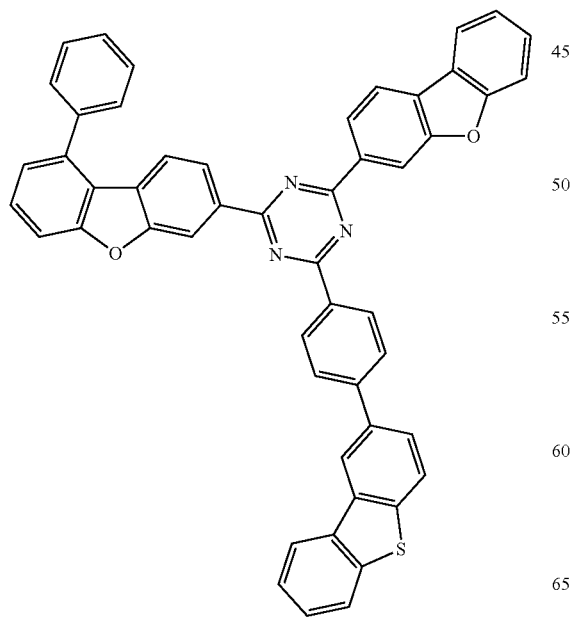
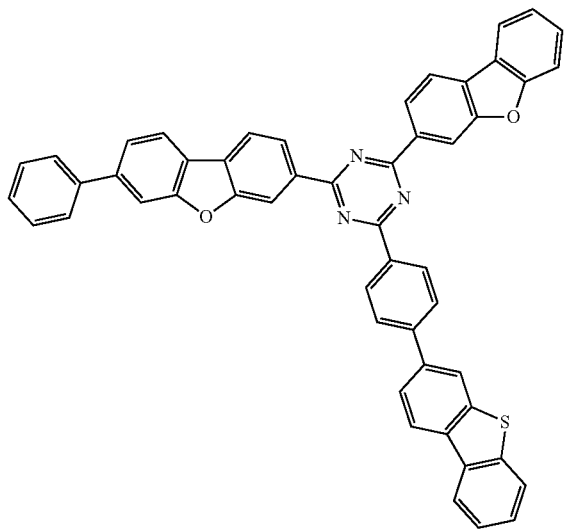

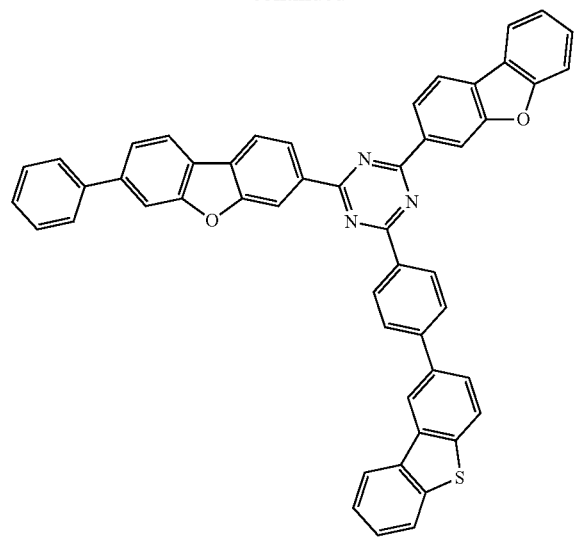
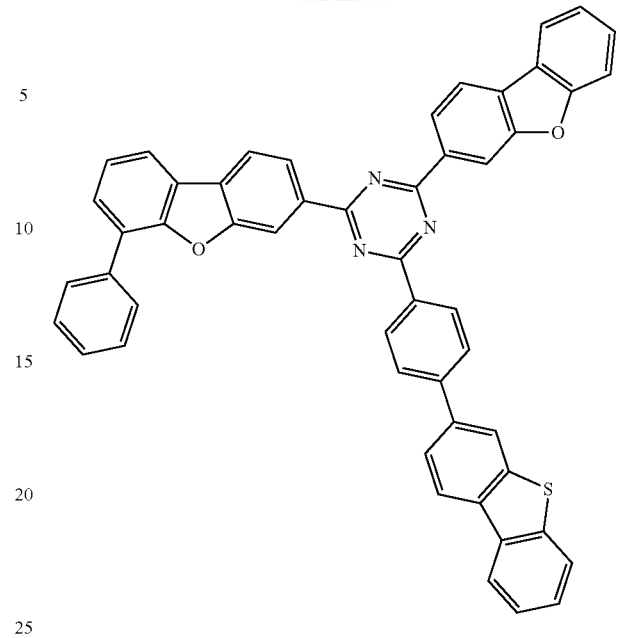
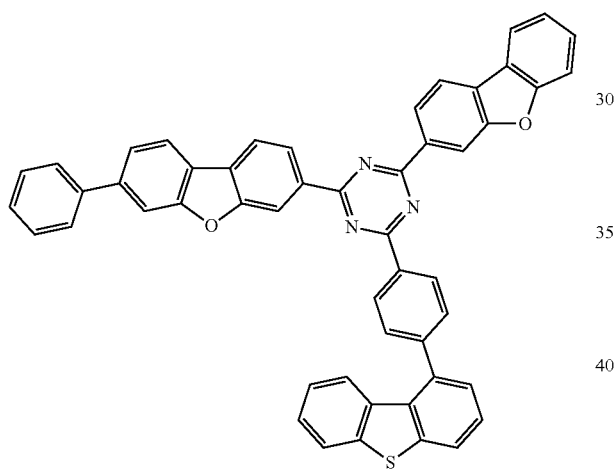
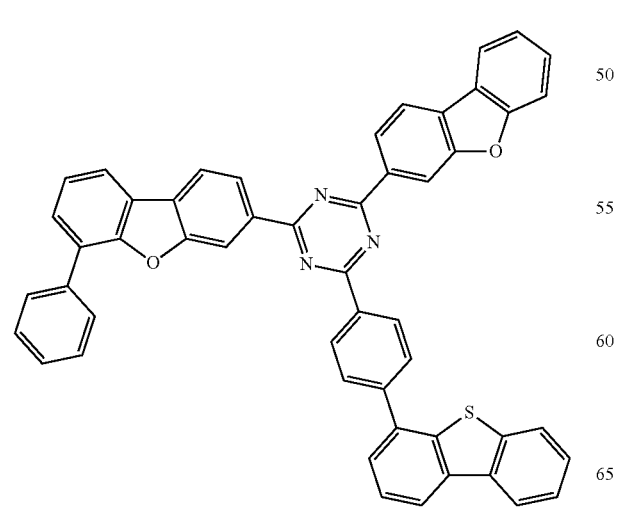
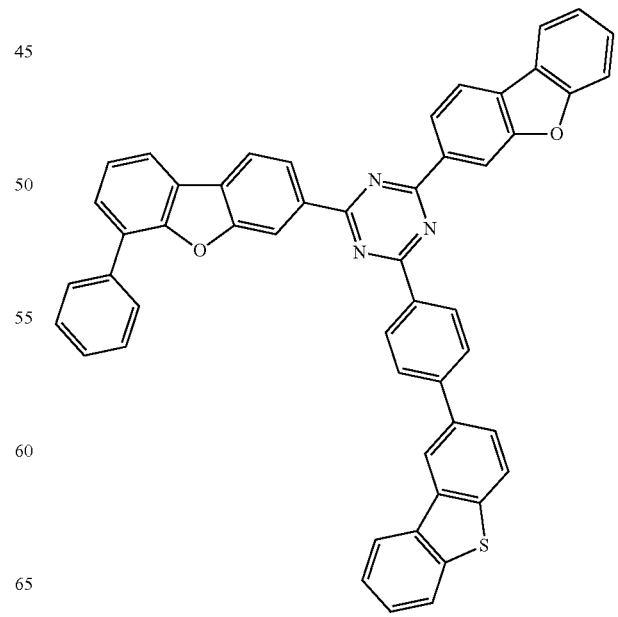

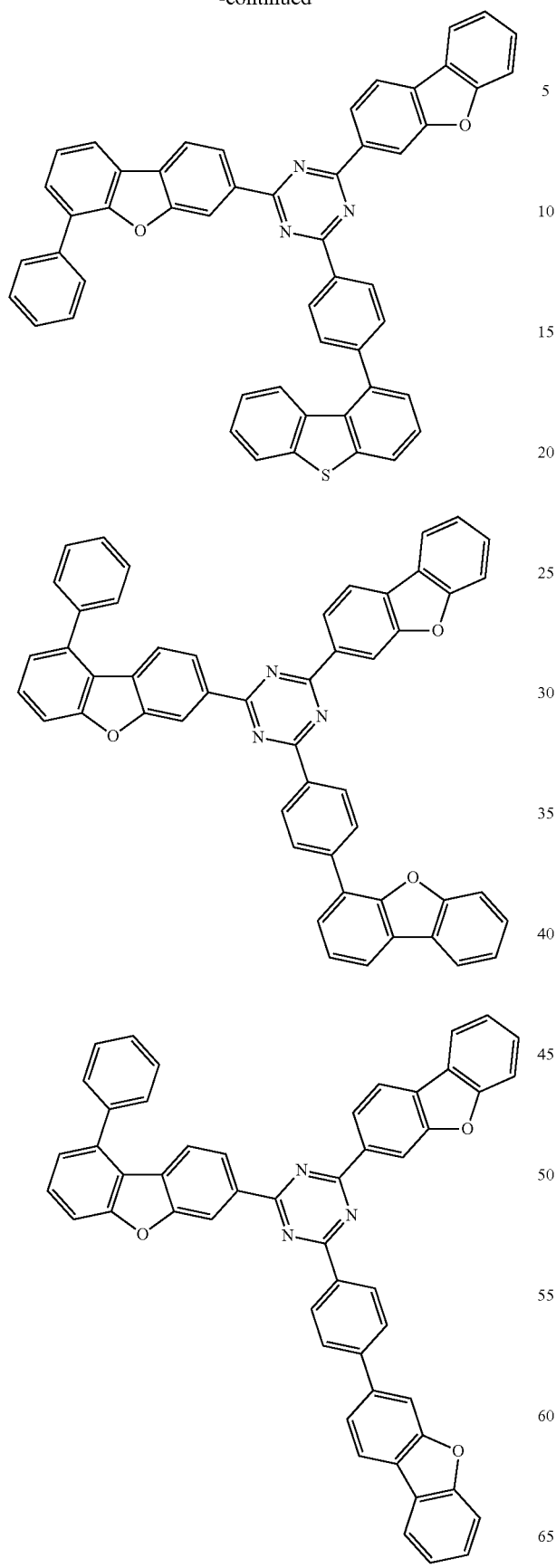
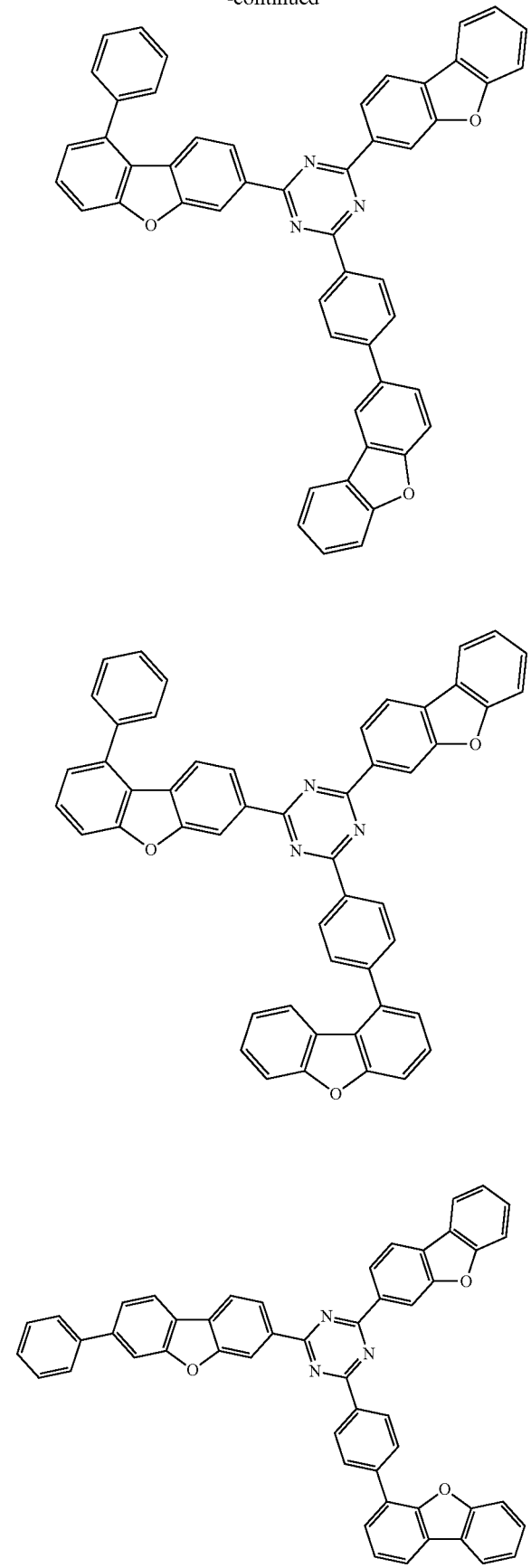

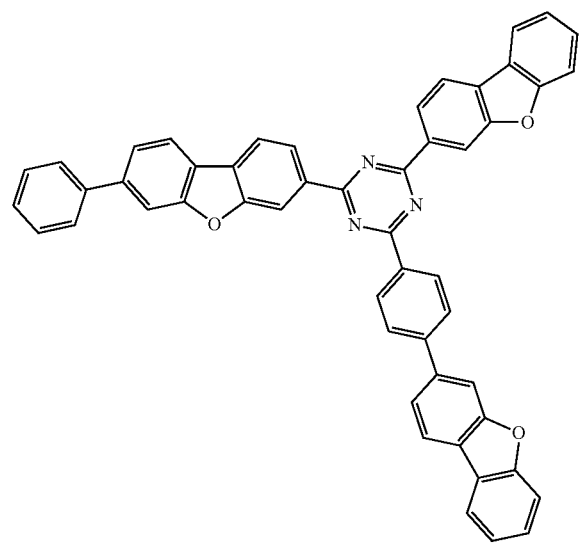
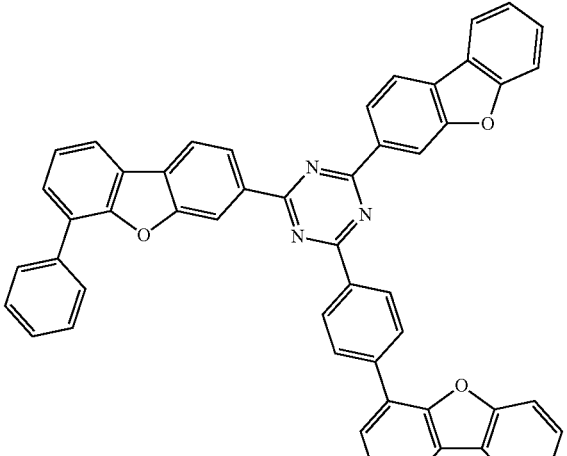

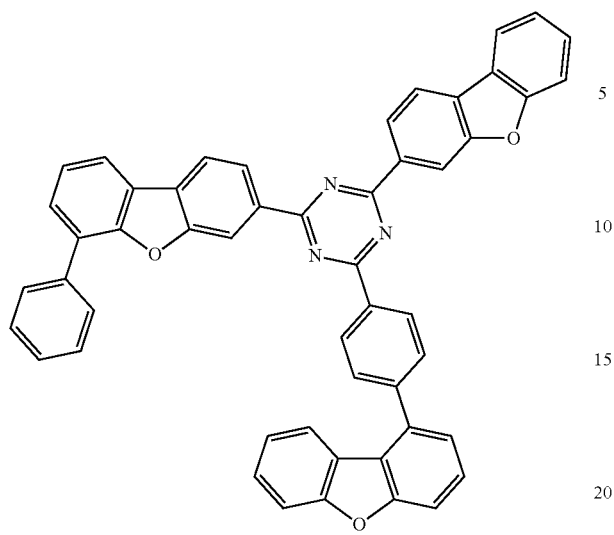
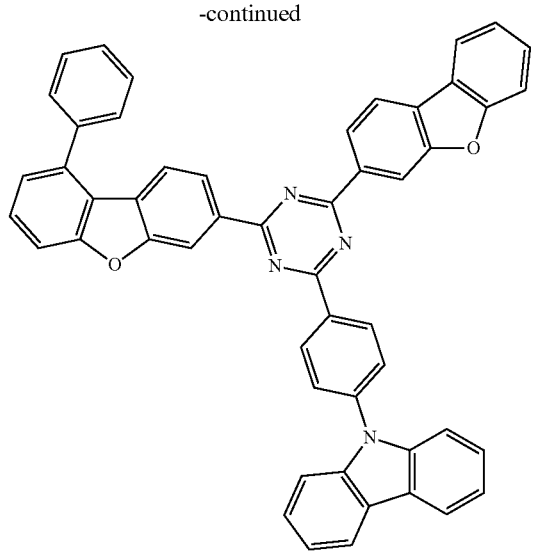
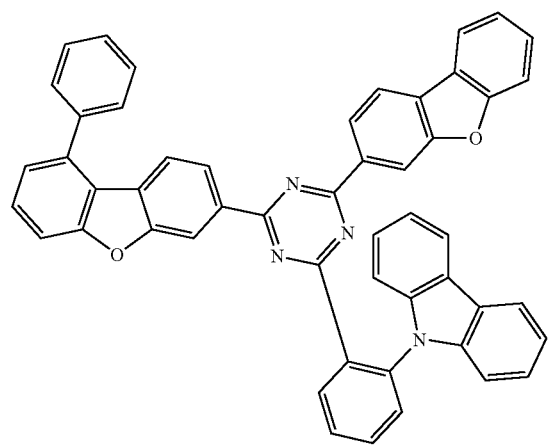
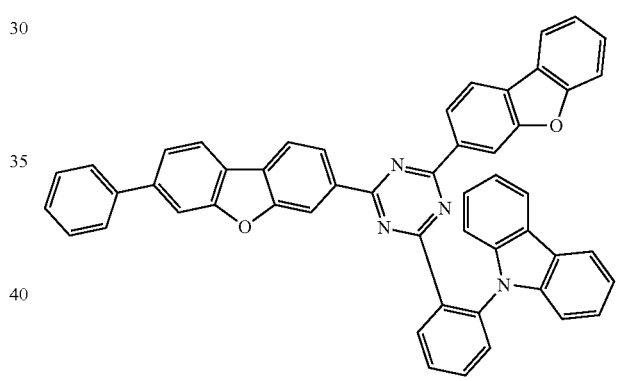
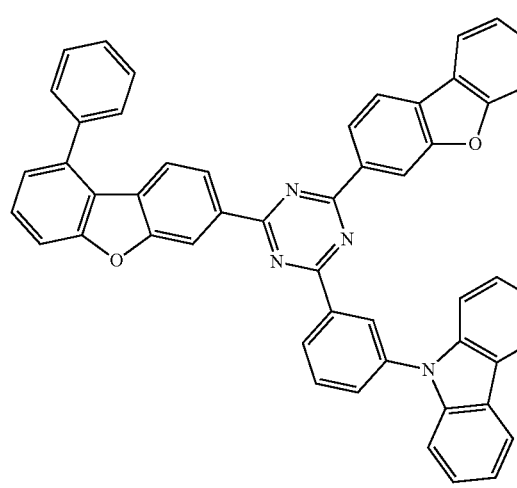
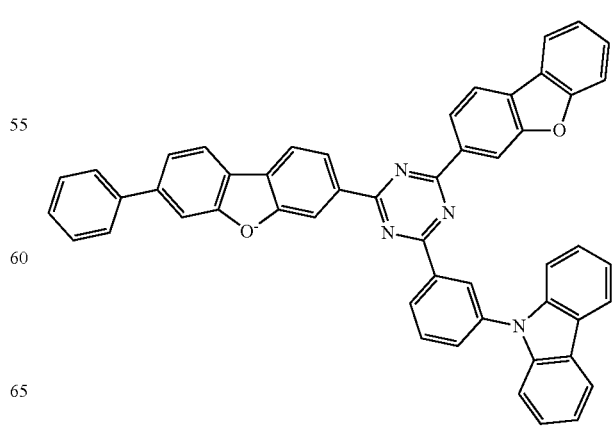

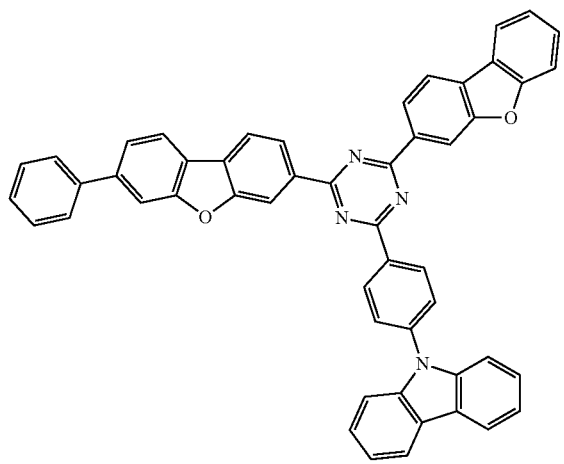

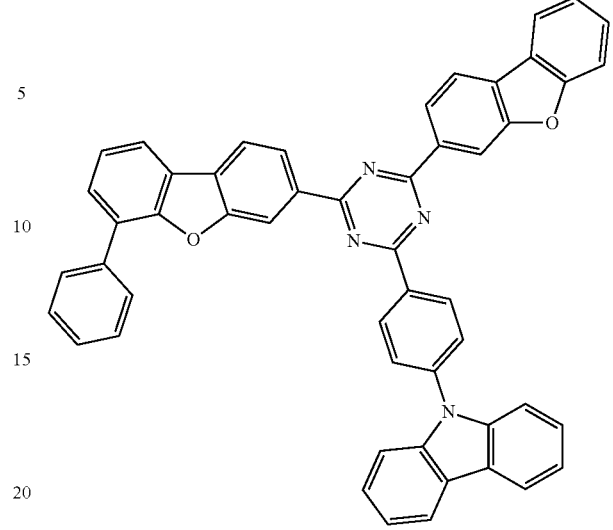

Meanwhile, the compound represented by Chemical Formula 1 can be prepared by the preparation method as shown in the following Reaction Scheme 1.

[Reaction Scheme 1]

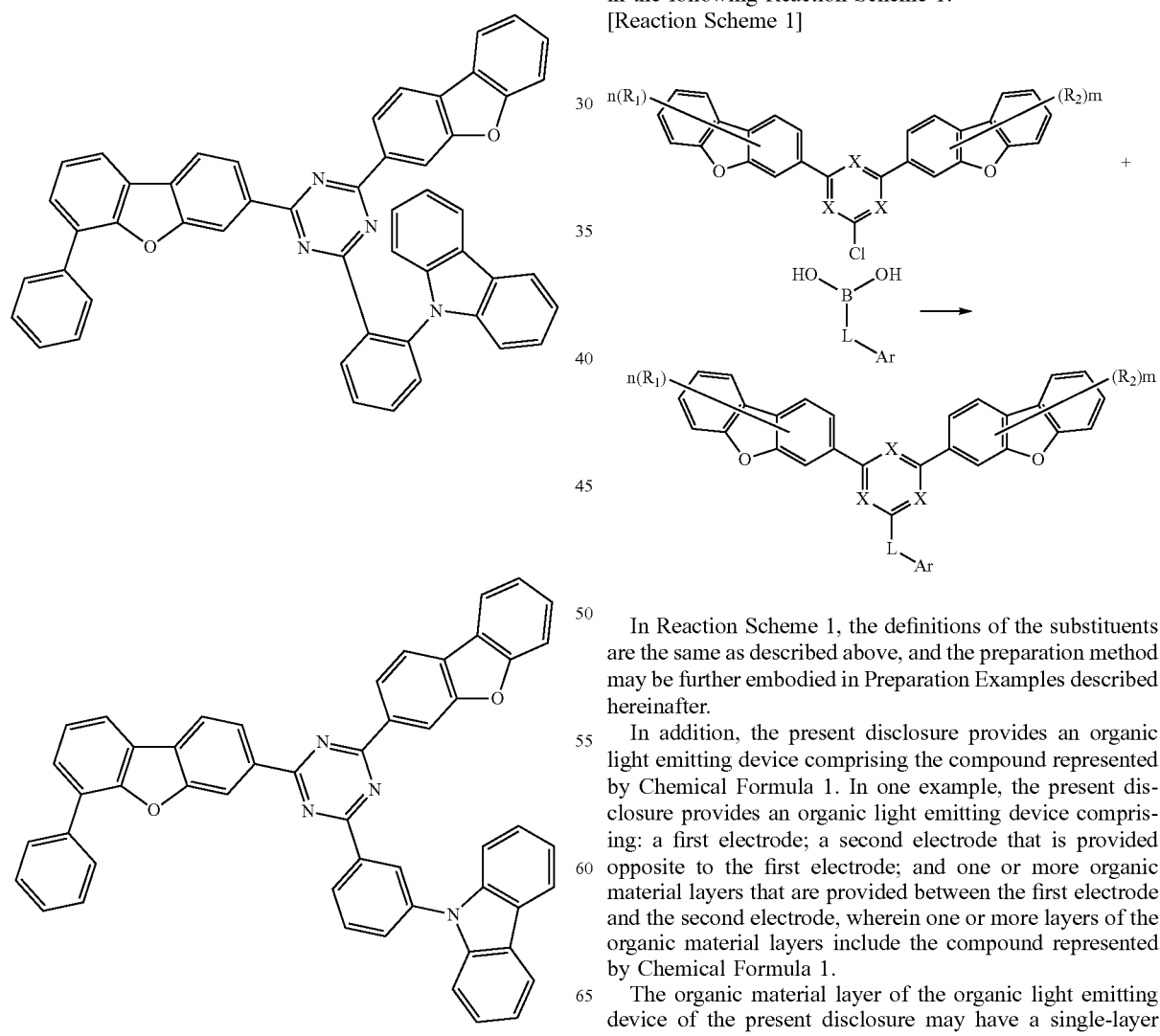

In Reaction Scheme 1, the definitions of the substituents are the same as described above, and the preparation method may be further embodied in Preparation Examples described hereinafter.

In addition, the present disclosure provides an organic light emitting device comprising the compound represented by Chemical Formula 1. In one example, the present disclosure provides an organic light emitting device comprising: a first electrode; a second electrode that is provided opposite to the first electrode; and one or more organic material layers that are provided between the first electrode and the second electrode, wherein one or more layers of the organic material layers include the compound represented by Chemical Formula 1.

The organic material layer of the organic light emitting device of the present disclosure may have a single-layer structure, or it may have a multilayered structure in which two or more organic material layers are stacked. For example, the organic light emitting device of the present disclosure may have a structure comprising a hole injection layer, a hole transport layer, an electron blocking layer, a light emitting layer, an electron transport layer, an electron injection layer and the like as the organic material layer. However, the structure of the organic light emitting device is not limited thereto, and it may include a smaller number of organic material layers.

Further, the organic material layer may include a hole injection layer, a hole transport layer, a layer for simultaneously performing hole injection and transport, wherein the hole injection layer, the hole transport layer, the layer for simultaneously performing hole injection and transport may include the compound represented by Chemical Formula 1.

Further, the organic material layer may include a light emitting layer, wherein the light emitting layer may include the compound represented by Chemical Formula 1. In this case, the compound represented by Chemical Formula 1 may be used as a host material in the light emitting layer.

Further, the light emitting layer may include two or more types of hosts. When the light emitting layer includes two or more types of hosts, at least one of the hosts may be the compound represented by Chemical Formula 1.

Further, the organic material layer may include an electron transport layer, or an electron injection layer, wherein the electron transport layer, or the electron injection layer includes the compound represented by Chemical Formula 1.

Further, the electron transport layer, the electron injection layer, or a layer for simultaneously performing electron transport and electron injection may include the compound represented by Chemical Formula 1.

Further, the organic material layer may include a light emitting layer and an electron transport layer, wherein the electron transport layer may include the compound represented by Chemical Formula 1.

Further, the organic light emitting device according to the present disclosure may be a normal type organic light emitting device in which an anode, one or more organic material layers, and a cathode are sequentially stacked on a substrate.

Further, the organic light emitting device according to the present disclosure may be an inverted type organic light emitting device in which a cathode, one or more organic material layers, and an anode are sequentially stacked on a substrate.

FIG. 1 depicts an example of an organic light emitting device comprising a substrate 1, an anode 2, a light emitting layer 3, and a cathode 4. In such a structure, the compound represented by Chemical Formula 1 may be included in the light emitting layer.

FIG. 2 depicts an example of an organic light emitting device comprising a substrate 1, an anode 2, a hole injection layer 5, a hole transport layer 6, an electron blocking layer 7, a light emitting layer 3, an electron transport layer 8, an electron injection layer 9, and a cathode 4. In such a structure, the compound represented by Chemical Formula 1 may be included in at least one of the hole injection layer, the hole transport layer, the electron blocking layer, the light emitting layer, the electron transport layer and the electron injection layer, and preferably, it may be included in the light emitting layer.

The organic light emitting device according to the present disclosure may be manufactured by materials and methods known in the art, except that at least one of the organic material layers includes the compound represented by Chemical Formula 1. Further, when the organic light emitting device includes a plurality of organic material layers, the organic material layers may be formed of the same material or different materials.

For example, the organic light emitting device according to the present disclosure can be manufactured by sequentially stacking a first electrode, an organic material layer and a second electrode on a substrate. In this case, the organic light emitting device may be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer and the electron transport layer thereon, and then depositing a material that can be used as the cathode thereon. In addition to such a method, the organic light emitting device may be manufactured by sequentially depositing a cathode material, an organic material layer and an anode material on a substrate.

Further, the compound represented by Chemical Formula 1 may be formed into an organic layer by a solution coating method as well as a vacuum deposition method at the time of manufacturing an organic light emitting device. Herein, the solution coating method means a spin coating, a dip coating, a doctor blading, an inkjet printing, a screen printing, a spray method, a roll coating, or the like, but is not limited thereto.

In addition to such a method, the organic light emitting device may be manufactured by sequentially depositing a cathode material, an organic material layer and an anode material on a substrate (International Publication WO2003/012890). However, the manufacturing method is not limited thereto.

As an example, the first electrode is an anode, and the second electrode is a cathode, or alternatively, the first electrode is a cathode and the second electrode is an anode.

As the anode material, generally, a material having a large work function is preferably used so that holes can be smoothly injected into the organic material layer.

Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SnO_2$:Sb; conductive compounds such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LF/Al or $LiO_2$/Al, and the like, but are not limited thereto.

The hole injection layer is a layer for injecting holes from the electrode, and the hole injection material is preferably a compound which has a capability of transporting the holes, thus has a hole injecting effect in the anode and an excellent hole injecting effect to the light emitting layer or the light emitting material, prevents excitons produced in the light emitting layer from moving to a hole injection layer or the electron injection material, and further is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive polymer, and the like, but are not limited thereto.

The hole transport layer is a layer that receives holes from a hole injection layer and transports the holes to the light emitting layer. The hole transport layer is suitably a material having large mobility to the holes, which may receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The electron blocking layer is formed on the hole transport layer, preferably provided in contact with the light emitting layer, and severs to adjust the hole mobility, prevent excessive movement of electrons and increase the probability of hole-electron coupling, thereby improving the efficiency of the organic light emitting device. The electron blocking layer includes an electron blocking material, and as such electron blocking material, a material having a stable structure in which electrons may not flow out of the light emitting layer is suitable. Specific examples thereof may include an arylamine-based organic material or the like, but are not limited thereto.

The light emitting material is preferably a material which may receive holes and electrons transported from a hole transport layer and an electron transport layer, respectively, and combine the holes and the electrons to emit light in a visible ray region, and has good quantum efficiency to fluorescence or phosphorescence.

Specific examples of the light emitting material include an 8-hydroxy-quinoline aluminum complex ($Alq_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene)(PPV)-based polymer; a spiro compound; polyfluorene, lubrene, and the like, but are not limited thereto.

The light emitting layer may include a host material and a dopant material. The host material may be a fused aromatic ring derivative, a heterocycle-containing compound or the like. Specific examples of the fused aromatic ring derivatives include anthracene derivatives, pyrene derivatives, naphthalene derivatives, pentacene derivatives, phenanthrene compounds, fluoranthene compounds, and the like. Examples of the heterocyclic-containing compounds include carbazole derivatives, dibenzofuran derivatives, ladder-type furan compounds, pyrimidine derivatives, and the like, but are not limited thereto.

Examples of the dopant material include an aromatic amine derivative, a styrylamine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene and the like, which have an arylamino group. The styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, the metal complex includes an iridium complex, a platinum complex, and the like, but is not limited thereto.

The electron transport layer is a layer which receives electrons from an electron injection layer and transports the electrons to a light emitting layer, and an electron transport material is suitably a material which may receive electrons well from a cathode and transfer the electrons to a light emitting layer, and has a large mobility for electrons. Specific examples of the electron transport material include: an Al complex of 8-hydroxyquinoline; a complex including $Alq_3$; an organic radical compound; a hydroxyflavone-metal complex, and the like, but are not limited thereto. The electron transport layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples of the electron injection layer include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato) beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The organic light emitting device according to the present disclosure may be a front side emission type, a back side emission type, or a double side emission type according to the used material.

In addition, the compound represented by Chemical Formula 1 may be included in an organic solar cell or an organic transistor in addition to an organic light emitting device.

The preparation of the compound represented by Chemical Formula 1 and the organic light emitting device containing the same will be described in detail in the following examples. However, these examples are presented for illustrative purposes only, and are not intended to limit the scope of the present disclosure.

Synthesis Example 1: Synthesis of Intermediate Compound Sub 1

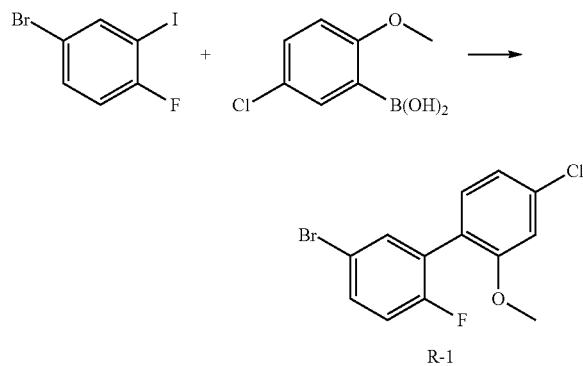

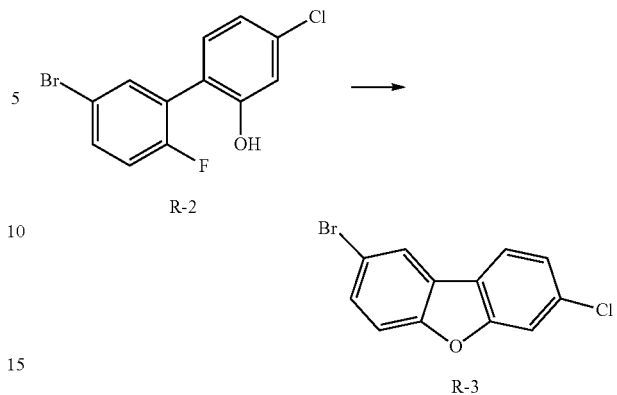

1-Bromo-4-fluoro-3-iodobenzene (50 g, 166.6 mmol) and (5-chloro-2-methoxyphenyl)boronic acid (31.1 g, 166.6 mmol) were dissolved in 800 ml of tetrahydrofuran (THF). Sodium carbonate (Na$_2$CO$_3$) 2M solution (250 mL) and tetrakis(triphenylphosphine)palladium(0) [Pd(PPh$_3$)$_4$] (3.8 g, 3 mol %) were added thereto, and refluxed for 12 hours. After completion of the reaction, the reaction temperature was cooled to room temperature, and the resulting mixture was extracted three times with water and toluene. The toluene layer was separated, dried over magnesium sulfate, and filtered. The filtrate was distilled under reduced pressure, and the resulting mixture was recrystallized three times using chloroform and ethanol to obtain Compound R-1 (27.5 g, yield: 51%; MS:[M+H]$^+$=314).

Compound R-2 (20.0 g, 66.4 mmol) was dissolved in distilled dimethylformamide (DMF) (200 ml). This was cooled to 0° C., and sodium hydride (1.8 g, 72.9 mmol) was slowly added dropwise thereto. The mixture was stirred for 20 minutes and then stirred at 100° C. for 1 hour. After completion of the reaction, the reaction temperature was cooled to room temperature, and 100 ml of ethanol was slowly added thereto. The mixture was distilled under reduced pressure, and recrystallized from chloroform and ethyl acetate to obtain Compound R-3 (15.2 g, yield: 81%; MS:[M+H]$^+$=280).

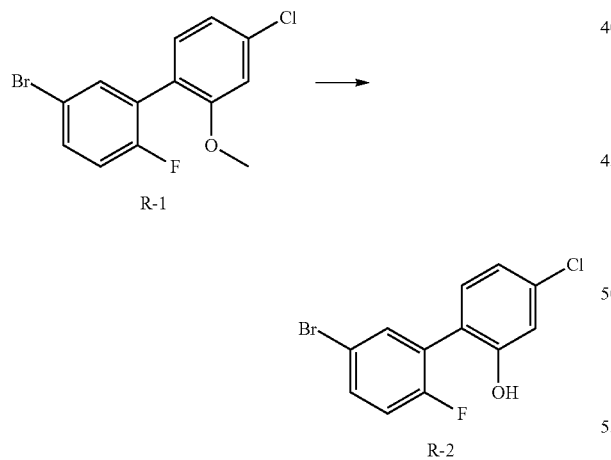

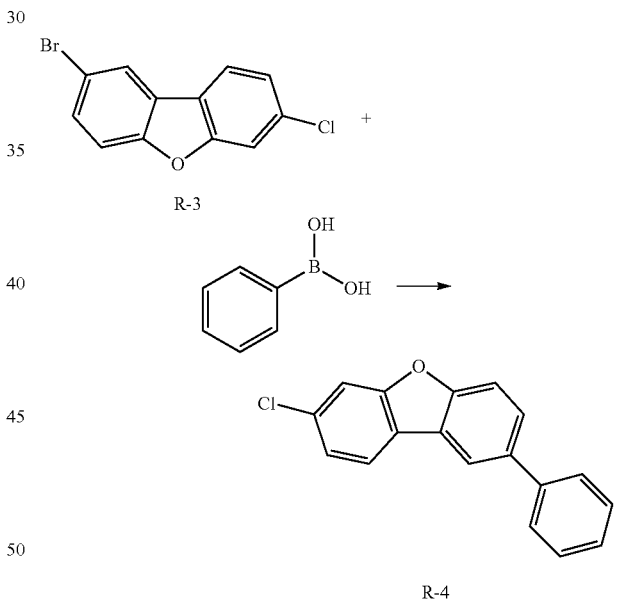

Compound R-1 (25.0 g, 150 mmol) was dissolved in dichloromethane (300 ml), and then cooled to 0° C. Boron tribromide (7.9 ml, 83.2 mmol) was slowly added dropwise and then stirred for 12 hours. After completion of the reaction, the mixture was washed three times with water, dried over magnesium sulfate, and filtered. The filtrate was distilled under reduced pressure and purified by column chromatography to obtain Compound R-2 (23.7 g, yield: 99%; MS:[M+H]$^+$=300).

R-3 (15 g, 53.6 mmol) and phenylboronic acid (6.5 g, 53.6 mmol) were added to 300 ml of tetrahydrofuran under a nitrogen atmosphere, and the mixture was stirred and refluxed. Then, potassium carbonate (22.2 g, 160.8 mmol) was dissolved in 22 ml of water, added thereto and sufficiently stirred, and then tetrakistriphenyl-phosphinopalladium (1.9 g, 1.6 mmol) was added. After the reaction for 2 hours, the reaction mixture was cooled to room temperature and then the organic layer and the aqueous layer were separated, and the organic layer was distilled. This was added again to 298 mL of chloroform, dissolved and washed twice with water. The organic layer was then separated, anhydrous magnesium sulfate was added, stirred and then filtered, and the filtrate was distilled under reduced pressure.

The concentrated compound was recrystallized from chloroform and ethyl acetate to prepare a white solid compound R-4 (10.1 g, 68%, MS: [M+H]$^+$=279.1).

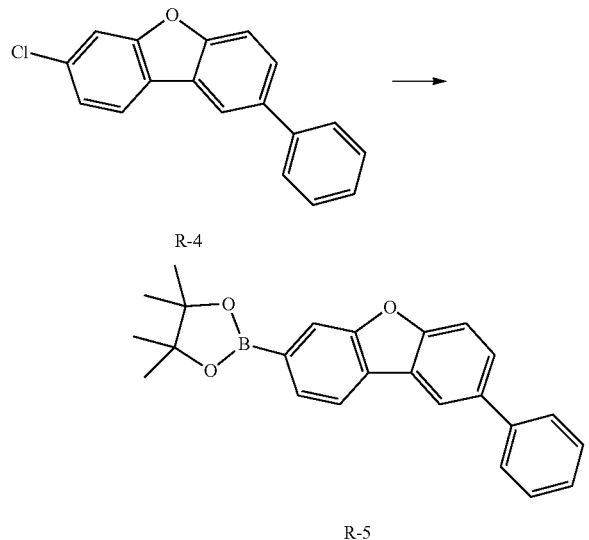

R-4 (10 g, 36 mmol) and bis(pinacolato)diboron (18.3 g, 71.9 mmol) were added to 200 ml of dioxane under a nitrogen atmosphere, and the mixture was stirred and refluxed. Then, potassium acetate (10.4 g, 107.9 mmol) was added thereto and sufficiently stirred, and then palladium dibenzylidene acetone palladium (0.6 g, 1.1 mmol) and tricyclohexylphosphine (0.6 g, 2.2 mmol) were added. After the reaction for 7 hours, the reaction mixture was cooled to room temperature, and then the organic layer was subjected to filtration treatment to remove a salt, and then the filtered organic layer was distilled. This was added again to 133 ml of chloroform, dissolved and washed twice with water. The organic layer was then separated, anhydrous magnesium sulfate was added, stirred and then filtered, and the filtrate was distilled under reduced pressure. The concentrated compound was recrystallized from chloroform and ethanol to prepare a white solid compound R-5 (12 g, 90%, MS: [M+H]$^+$=371.2).

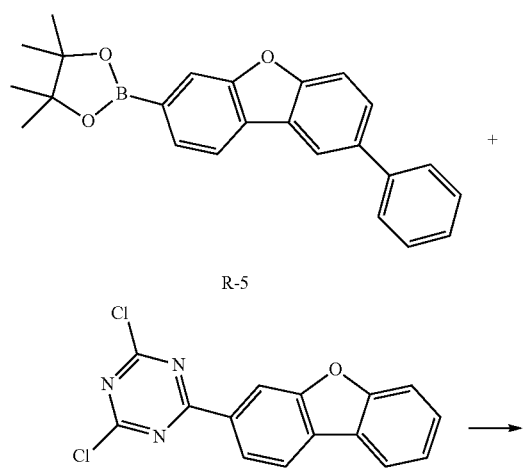

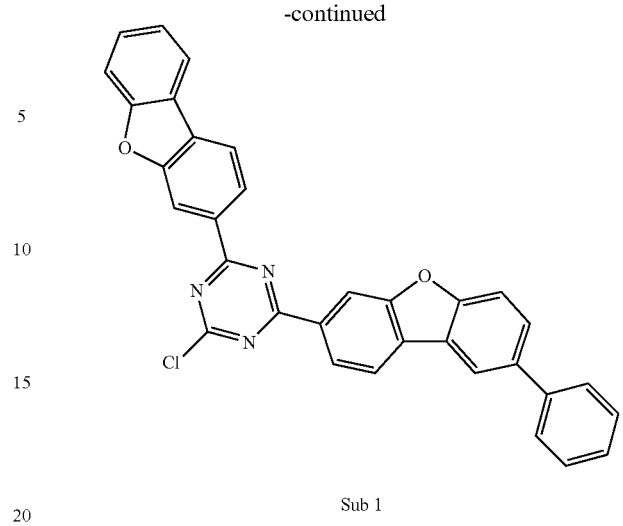

R-5 (10 g, 27 mmol) and 2,4-dichloro-6-(dibenzo[b,d]furan-3-yl)-1,3,5-triazine (3.3 g, 27 mmol) were added to 200 ml of tetrahydrofuran under a nitrogen atmosphere, and the mixture was stirred and refluxed. Then, potassium carbonate (11.2 g, 81 mmol) was dissolved in 11 ml of water, added thereto and sufficiently stirred, and then tetrakistriphenyl-phosphinopalladium (0.9 g, 0.8 mmol) was added. After the reaction for 1 hour, the reaction mixture was cooled to room temperature and then the organic layer and the aqueous layer were separated, and the organic layer was distilled. This was added again to 283 mL of chloroform, dissolved and washed twice with water. The organic layer was then separated, anhydrous magnesium sulfate was added, stirred and then filtered, and the filtrate was distilled under reduced pressure. The concentrated compound was recrystallized from chloroform and ethyl acetate to prepare a white solid compound Sub 1 (11 g, 78%, MS: [M+H]$^+$=524.1).

Synthesis Example 2: Synthesis of Intermediate Compound Sub 2

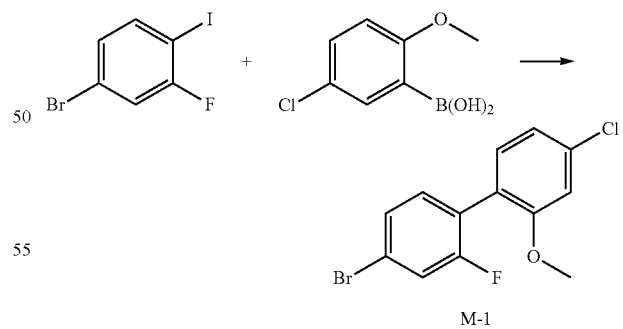

1-Bromo-3-fluoro-4-iodobenzene (50 g, 166.6 mmol), (5-chloro-2-methoxyphenyl) boronic acid (31.1 g, 166.6 mmol) were dissolved in 800 ml of tetrahydrofuran (THF). Sodium carbonate (Na$_2$CO$_3$) 2M solution (250 mL) and tetrakis(triphenylphosphine)palladium(0) [Pd(PPh$_3$)$_4$] (3.8 g, 3 mol %) weres added thereto, and refluxed for 12 hours. After completion of the reaction, the reaction temperature was cooled to room temperature, and the resulting mixture was extracted three times with water and toluene. The toluene layer was separated, dried over magnesium sulfate, and filtered. The filtrate was distilled under reduced pressure, and the resulting mixture was recrystallized three times using chloroform and ethanol to obtain Compound M-1 (27.5 g, yield: 51%; MS:[M+H]$^+$=314)

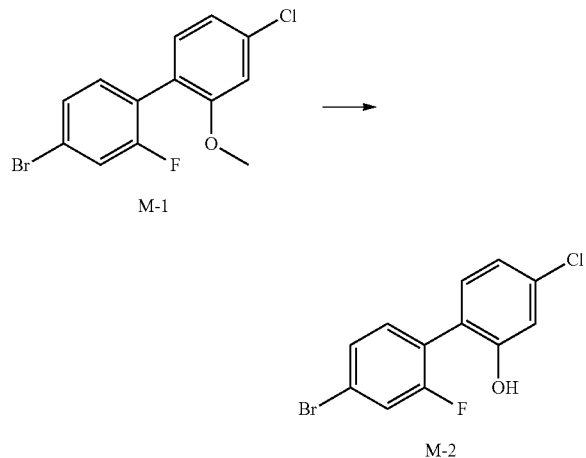

Compound M-1 (25.0 g, 150 mmol) was dissolved in dichloromethane (300 ml), and then cooled to 0° C. Boron tribromide (7.9 ml, 83.2 mmol) was slowly added dropwise and then stirred for 12 hours. After completion of the reaction, the mixture was washed three times with water, dried over magnesium sulfate, and filtered. The filtrate was distilled under reduced pressure and purified by column chromatography to obtain Compound M-2 (23.7 g, yield: 99%; MS:[M+H]$^+$=300).

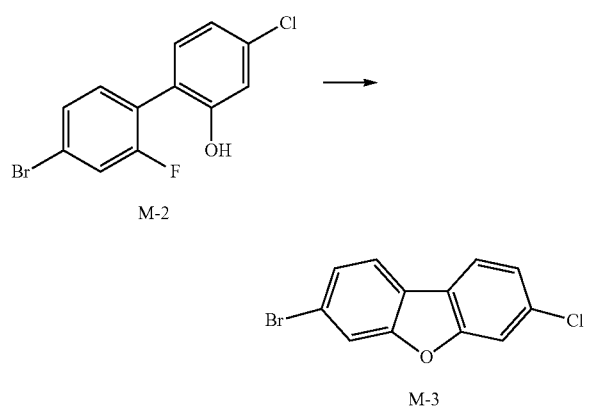

Compound M-2 (20.0 g, 66.4 mmol) was dissolved in distilled dimethylformamide (DMF) (200 ml). This was cooled to 0° C., and sodium hydride (1.8 g, 72.9 mmol) was slowly added dropwise thereto. The mixture was stirred for 20 minutes and then stirred at 100° C. for 1 hour. After completion of the reaction, the reaction temperature was cooled to room temperature, and 100 ml of ethanol was slowly added thereto. The mixture was distilled under reduced pressure, and recrystallized from chloroform and ethyl acetate to obtain Compound M-3 (15.2 g, yield: 81%; MS:[M+H]$^+$=280).

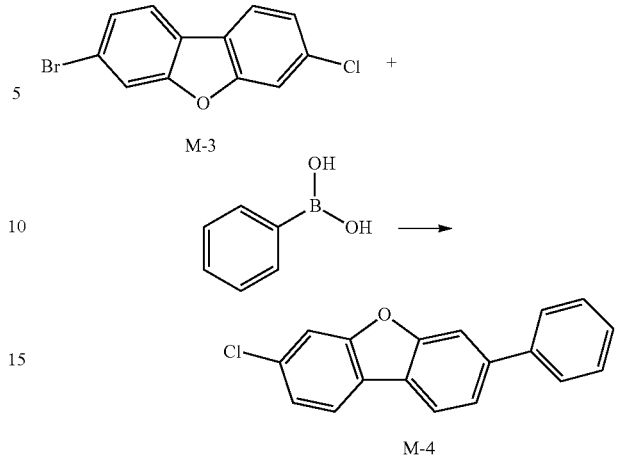

M-3 (15 g, 53.6 mmol) and phenylboronic acid (6.5 g, 53.6 mmol) were added to 300 ml of tetrahydrofuran under a nitrogen atmosphere, and the mixture was stirred and refluxed. Then, potassium carbonate (22.2 g, 160.8 mmol) was dissolved in 22 ml of water, added thereto and sufficiently stirred, and then tetrakistriphenyl-phosphinopalladium (1.9 g, 1.6 mmol) was added. After the reaction for 2 hours, the reaction mixture was cooled to room temperature, and then the organic layer and the aqueous layer were separated, and the organic layer was distilled. This was added again to 298 mL of chloroform, dissolved and washed twice with water. The organic layer was then separated, anhydrous magnesium sulfate was added, stirred and then filtered, and the filtrate was distilled under reduced pressure. The concentrated compound was recrystallized from chloroform and ethyl acetate to prepare a white solid compound M-4 (10.5 g, 71%, MS: [M+H]$^+$=279.1).

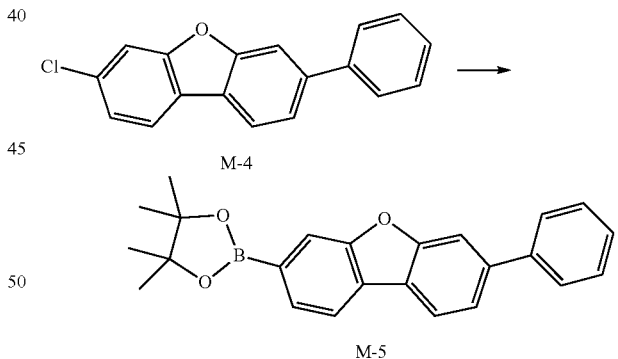

M-4 (10 g, 36 mmol) and bis(pinacolato)diboron (18.3 g, 71.9 mmol) were added to 200 ml of dioxane under a nitrogen atmosphere, and the mixture was stirred and refluxed. Then, potassium acetate (10.4 g, 107.9 mmol) was added thereto and sufficiently stirred, and then palladium dibenzylidene acetone palladium (0.6 g, 1.1 mmol) and tricyclohexylphosphine (0.6 g, 2.2 mmol) were added. After the reaction for 7 hours, the reaction mixture was cooled to room temperature, and then the organic layer was subjected to filtration treatment to remove a salt, and then the filtered organic layer was distilled. This was added again to 133 ml of chloroform, dissolved and washed twice with water. The organic layer was then separated, anhydrous magnesium sulfate was added, stirred and then filtered, and the filtrate was distilled under reduced pressure. The concentrated compound was recrystallized from chloroform and ethanol to prepare a white solid compound M-5 (11.7 g, 88%, MS: [M+H]$^+$=371.2).

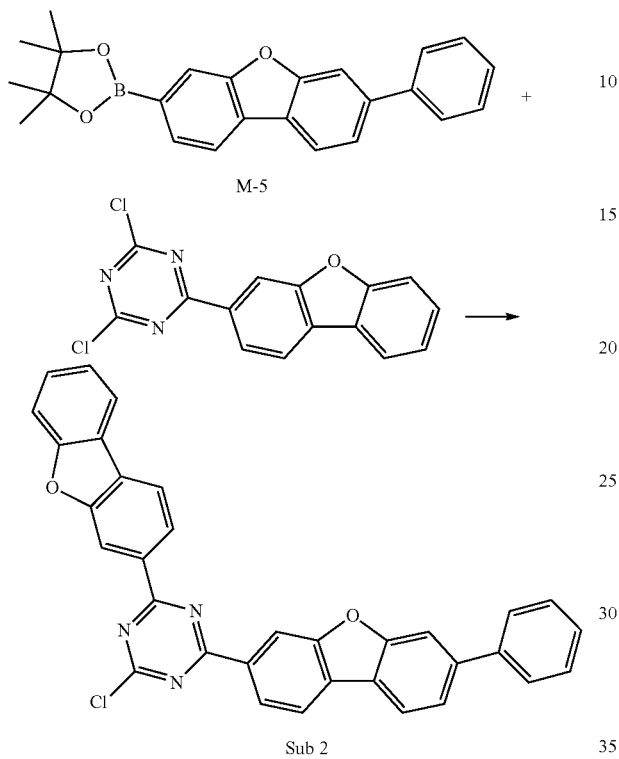

M-5 (10 g, 27 mmol) and 2,4-dichloro-6-(dibenzo[b,d]furan-3-yl)-1,3,5-triazine (3.3 g, 27 mmol) in tetrahydrofuran were added to 200 ml of tetrahydrofuran under a nitrogen atmosphere, and the mixture was stirred and refluxed. Then, potassium carbonate (11.2 g, 81 mmol) was dissolved in 11 ml of water, added thereto and sufficiently stirred, and then tetrakistriphenyl-phosphinopalladium (0.9 g, 0.8 mmol) was added. After the reaction for 1 hour, the reaction mixture was cooled to room temperature and then the organic layer and the aqueous layer were separated, and the organic layer was distilled. This was added again to 283 mL of chloroform, dissolved and washed twice with water. The organic layer was then separated, anhydrous magnesium sulfate was added, stirred and then filtered, and the filtrate was distilled under reduced pressure. The concentrated compound was recrystallized from chloroform and ethyl acetate to prepare a white solid compound Sub 2 (11.3 g, 80%, MS: [M+H]$^+$=524.1).

Synthesis Example 3: Synthesis of Intermediate Compound Sub 3

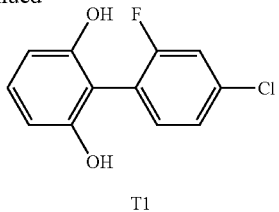

T1

Intermediate 5-1a (40.4 g, yield 75%, MS:[M+H]$^+$=239) was prepared in the same manner as in the method for preparing Intermediate P1 below, except that (4-chloro-2-fluorophenyl)boronic acid was used instead of (3-chloro-2-fluorophenyl)boronic acid.

Intermediate T2 (26.8 g, yield 72%, MS:[M+H]$^+$=219) was prepared in the same manner as in the method for preparing Intermediate P2 below, except that Intermediate T1 was used instead of intermediate P1.

-continued

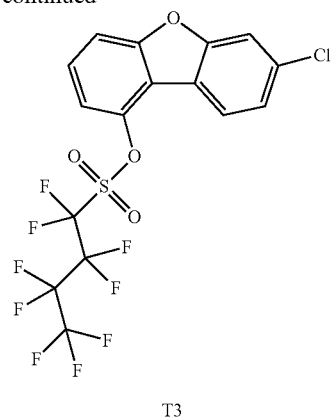

T3

Intermediate T3 (50.1 g, yield: 81%, MS:[M+H]$^+$=500) was prepared in the same manner as in the method for preparing Intermediate P3 below, except that Intermediate T2 was used instead of intermediate P2.

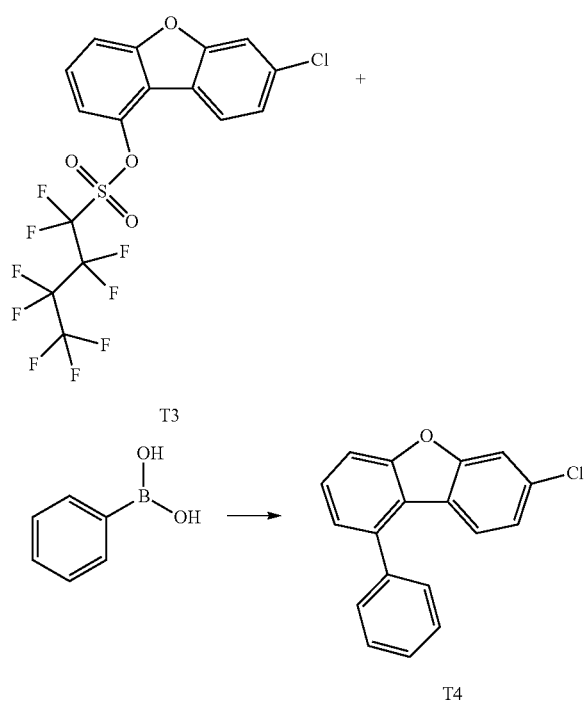

T3 (30 g, 60 mmol) and phenyl boronic acid (7.3 g, 60 mmol) were added to 600 ml of tetrahydrofuran under a nitrogen atmosphere, and the mixture was stirred and refluxed. Then, potassium acetate (24.9 g, 180 mmol) was added to 25 ml of water and sufficiently stirred, and then tetrakistriphenyl-phosphinopalladium (2.1 g, 1.8 mmol) was added. After the reaction for 1 hour, the reaction mixture was cooled to room temperature, and then the organic layer and the aqueous layer were separated, and the organic layer was distilled. This was added again to 334 mL of chloroform, dissolved and washed twice with water. The organic layer was then separated, anhydrous magnesium sulfate was added, stirred and then filtered, and the filtrate was distilled under reduced pressure. The concentrated compound was recrystallized from chloroform and ethyl acetate to prepare a white solid compound T4 (12.8 g, 77%, MS: [M+H]$^+$= 279.1).

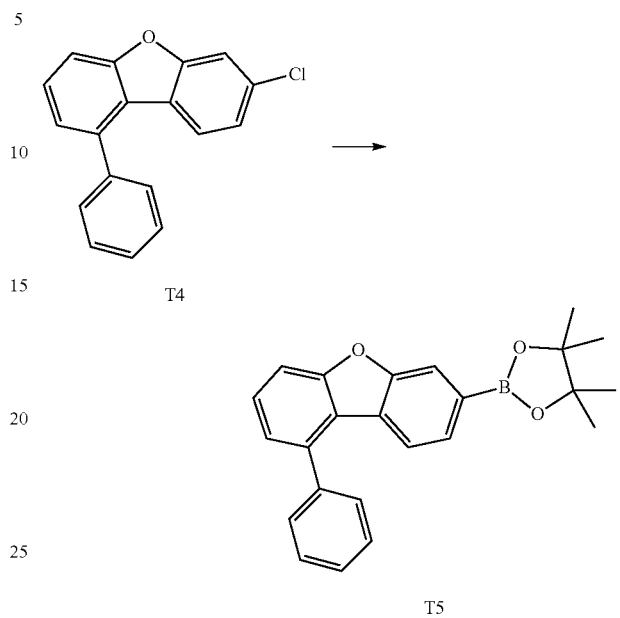

T4 (10 g, 36 mmol) and bis(pinacolato)diboron (18.3 g, 71.9 mmol) were added to 200 ml of dioxane under a nitrogen atmosphere, and then the mixture was stirred and refluxed. Then, potassium acetate (10.4 g, 107.9 mmol) was added thereto and sufficiently stirred, and then palladium dibenzylidene acetone palladium (0.6 g, 1.1 mmol) and tricyclohexylphosphine (0.6 g, 2.2 mmol) were added. After the reaction for 6 hours, the reaction mixture was cooled to room temperature, and then the organic layer was subjected to filtration treatment to remove a salt, and then the filtered organic layer was distilled. This was added again to 133 ml of chloroform, dissolved and washed twice with water. The organic layer was then separated, anhydrous magnesium sulfate was added, stirred and then filtered, and the filtrate was distilled under reduced pressure. The concentrated compound was recrystallized from chloroform and ethanol to prepare a white solid compound T5 (11 g, 83%, MS: [M+H]$^+$=371.2).

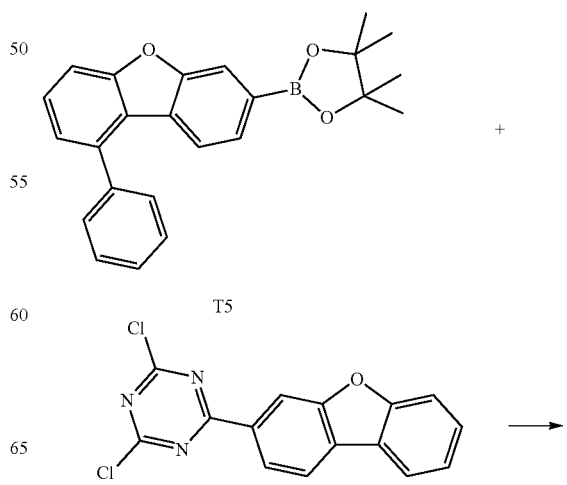

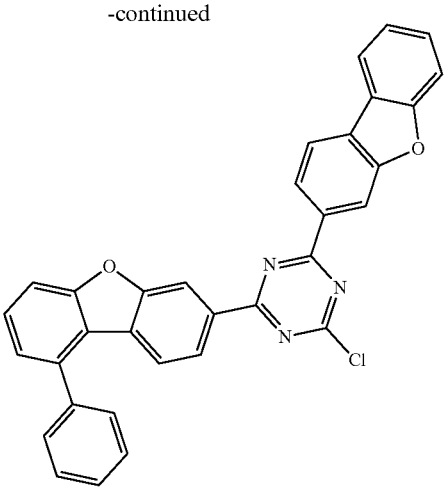

Sub 3

T5(15 g, 40.5 mmol) and 2,4-dichloro-6-(dibenzo[b,d]furan-3-yl)-1,3,5-triazine(12.8 g, 40.5 mmol) were added to 300 ml of tetrahydrofuran under a nitrogen atmosphere, and the mixture was stirred and refluxed. Then, potassium carbonate (16.8 g, 121.6 mmol) was dissolved in 17 ml of water, added thereto and sufficiently stirred, and then tetrakistriphenyl-phosphinopalladium (1.4 g, 1.2 mmol) was added. After the reaction for 2 hours, the reaction mixture was cooled to room temperature, the organic layer and the aqueous layer were separated, and the organic layer was distilled. This was added again to 424 ml of chloroform, dissolved and washed twice with water. The organic layer was then separated, anhydrous magnesium sulfate was added, stirred and then filtered, and the filtrate was distilled under reduced pressure. The concentrated compound was recrystallized from chloroform and ethyl acetate to prepare a white solid compound Sub 3 (15.7 g, 74%, MS: [M+H]$^+$= 524.1).

Synthesis Example 4: Synthesis of Intermediate Compound Sub 4

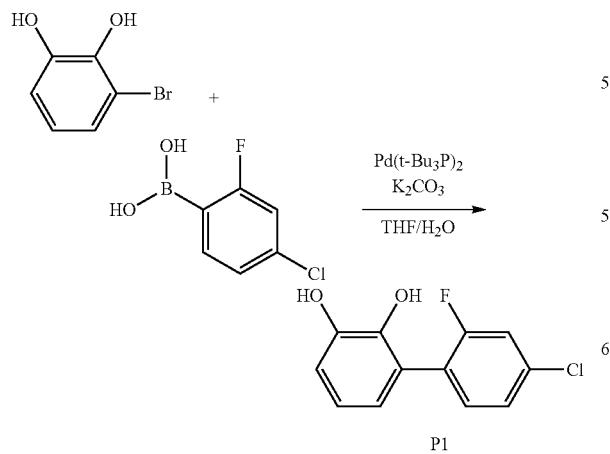

After 3-bromobenzene-1,2-diol (50 g, 0.26 mol) and (4-chloro-2-fluorophenyl)boronic acid (46.1 g, 0.21 mol) were dissolved in tetrahydrofuran (500 mL) in a 2000 mL round bottom flask under a nitrogen atmosphere, 1.5M aqueous potassium carbonate solution (400 mL) was added and bis(tri-tert-butylphosphine)palladium (0) (1.35 g, 2.36 mmol) was added. The mixture was heated and stirred for 1 hour. The temperature was lowered to room temperature and the aqueous layer was separated and removed, dried over anhydrous magnesium sulfate, then concentrated under reduced pressure, recrystallized with hexane, and then dried to prepare Compound P1 (49.8 g, yield: 79%, MS: [M+H]$^+$= 239).

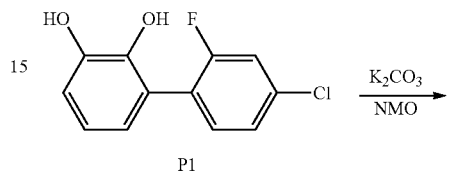

P1

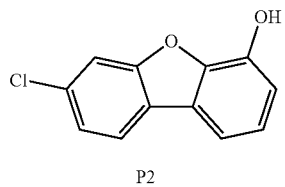

P2

Intermediate P1 (49.8 g, 0.21 mol) and calcium carbonate (57.7 g, 0.42 mol) were dissolved in N-methyl-2-pyrrolidone (200 mL) in a 500 mL round bottom flask, and then the mixture was heated and stirred for 2 hours. The temperature was lowered to room temperature and subjected to reverse precipitation in water, and filtered. The product was completely dissolved in dichloromentane, then washed with water, dried over anhydrous magnesium sulfate, then concentrated under reduced pressure, recrystallized with ethanol, and dried to prepare compound P2 (31.8 g, yield: 70%, MS: [M+H]$^+$=219).

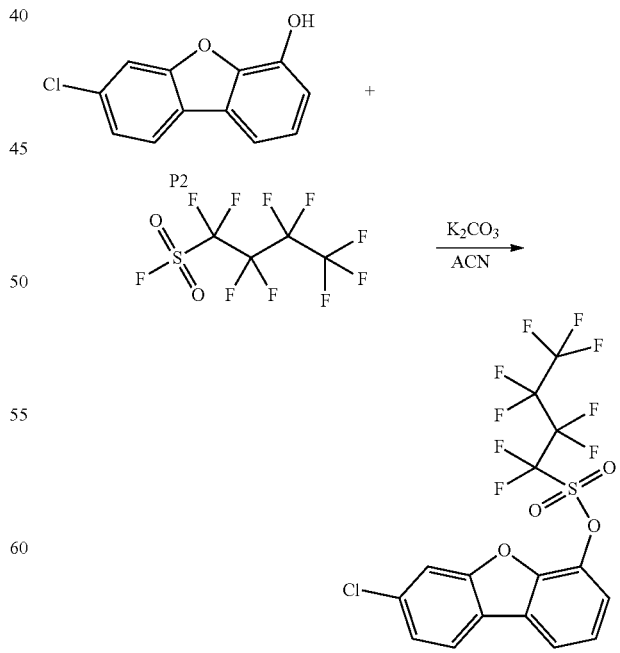

P3

Compound P2 (31.8 g, 0.15 mol) was dissolved in acetonitrile (150 mL) in a 500 mL round bottom flask, and calcium carbonate (33.1 g, 0.24 mol) was dissolved in water (150 mL), added thereto and then nonafluorobutanesulfonyl fluoride (28.7 mL, 0.16 mol) was slowly added dropwise for 30 minutes. Then, the mixture was stirred at room temperature for 3 hours. Upon completion of the reaction, the reaction mixture was filtered, completely dissolved in dichloromentane, then washed with water, dried over anhydrous magnesium sulfate, concentrated under reduced pressure, recrystallized with ethanol, and then dried to prepare compound P3 (53.3 g, yield: 73%, MS: [M+H]+=501).

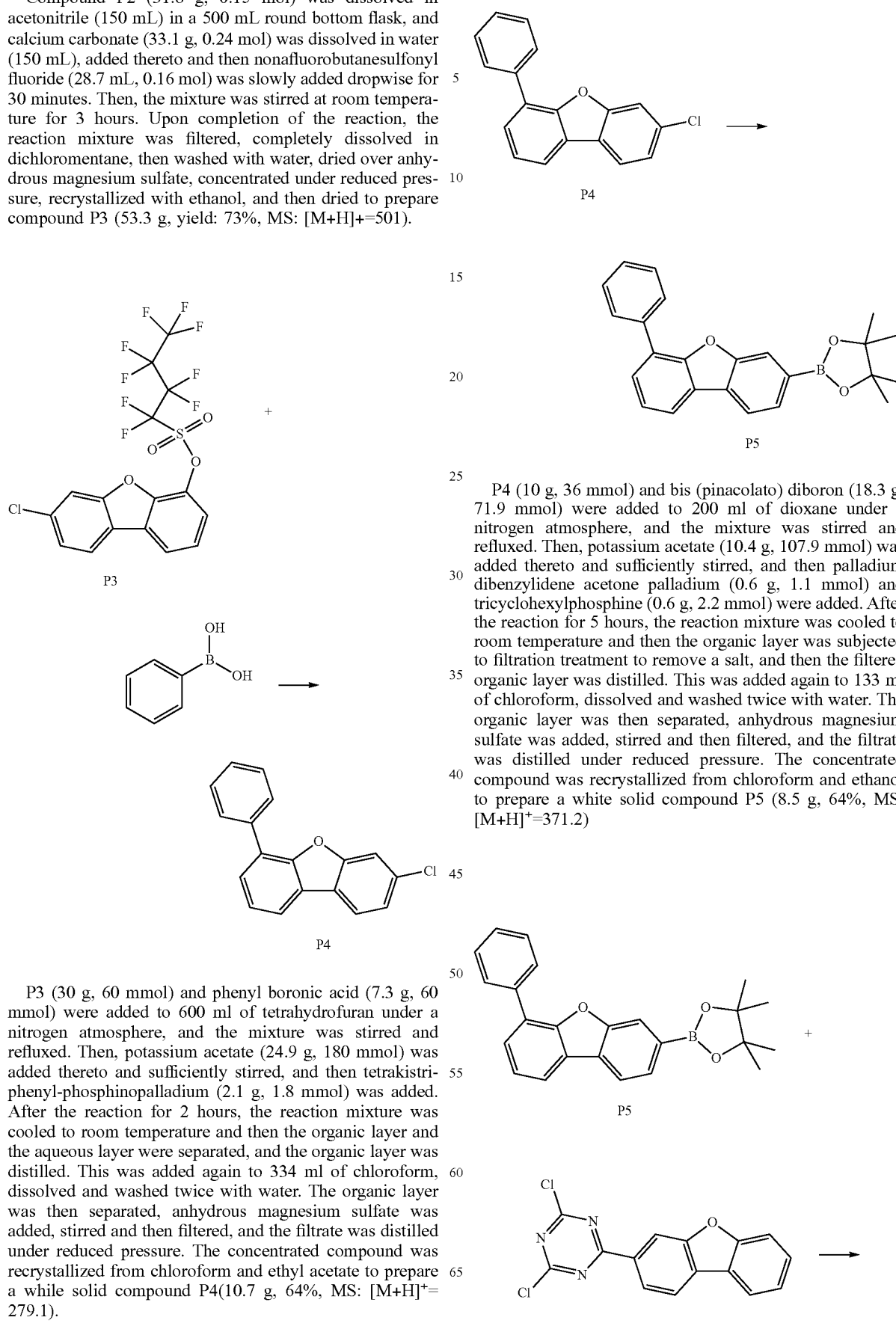

P3 (30 g, 60 mmol) and phenyl boronic acid (7.3 g, 60 mmol) were added to 600 ml of tetrahydrofuran under a nitrogen atmosphere, and the mixture was stirred and refluxed. Then, potassium acetate (24.9 g, 180 mmol) was added thereto and sufficiently stirred, and then tetrakistriphenyl-phosphinopalladium (2.1 g, 1.8 mmol) was added. After the reaction for 2 hours, the reaction mixture was cooled to room temperature and then the organic layer and the aqueous layer were separated, and the organic layer was distilled. This was added again to 334 ml of chloroform, dissolved and washed twice with water. The organic layer was then separated, anhydrous magnesium sulfate was added, stirred and then filtered, and the filtrate was distilled under reduced pressure. The concentrated compound was recrystallized from chloroform and ethyl acetate to prepare a while solid compound P4(10.7 g, 64%, MS: [M+H]+= 279.1).

P4 (10 g, 36 mmol) and bis (pinacolato) diboron (18.3 g, 71.9 mmol) were added to 200 ml of dioxane under a nitrogen atmosphere, and the mixture was stirred and refluxed. Then, potassium acetate (10.4 g, 107.9 mmol) was added thereto and sufficiently stirred, and then palladium dibenzylidene acetone palladium (0.6 g, 1.1 mmol) and tricyclohexylphosphine (0.6 g, 2.2 mmol) were added. After the reaction for 5 hours, the reaction mixture was cooled to room temperature and then the organic layer was subjected to filtration treatment to remove a salt, and then the filtered organic layer was distilled. This was added again to 133 ml of chloroform, dissolved and washed twice with water. The organic layer was then separated, anhydrous magnesium sulfate was added, stirred and then filtered, and the filtrate was distilled under reduced pressure. The concentrated compound was recrystallized from chloroform and ethanol to prepare a white solid compound P5 (8.5 g, 64%, MS: [M+H]+=371.2)

-continued

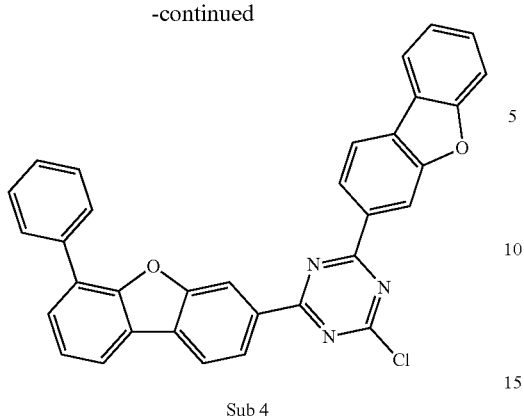

Sub 4

P5 (15 g, 40.5 mmol) and 2,4-dichloro-6-(dibenzo[b,d]furan-3-yl)-1,3,5-triazine (12.8 g, 40.5 mmol) were added to 300 ml of tetrahydrofuran under a nitrogen atmosphere, and the mixture was stirred and refluxed. Then, potassium acetate (16.8 g, 121.6 mmol) was dissolved in 17 mol of water, added thereto and sufficiently stirred, and then tetrakistriphenyl-phosphinopalladium (1.4 g, 1.2 mmol) was added. After the reaction for 1 hour, the reaction mixture was cooled to room temperature and then the organic layer and the aqueous layer were separated, and the organic layer was distilled. This was added again to 424 ml of chloroform, dissolved and washed twice with water. The organic layer was then separated, anhydrous magnesium sulfate was added, stirred and then filtered, and the filtrate was distilled under reduced pressure. The concentrated compound was recrystallized from chloroform and ethyl acetate to prepare a while solid compound Sub 4 (15.3 g, 72%, MS: [M+H]$^+$= 524.1).

Preparation Example 1: Preparation of Compound 1

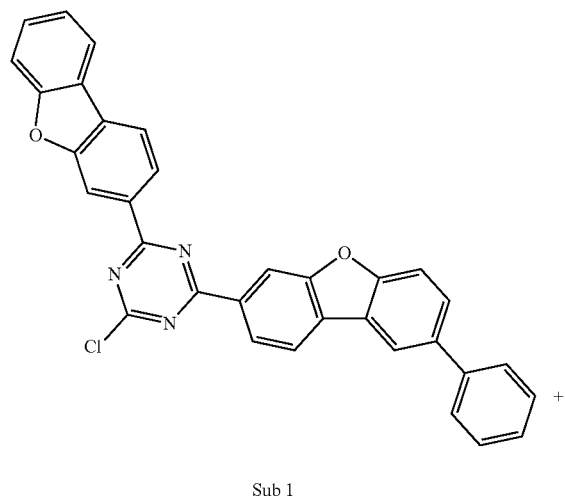

Sub 1

-continued

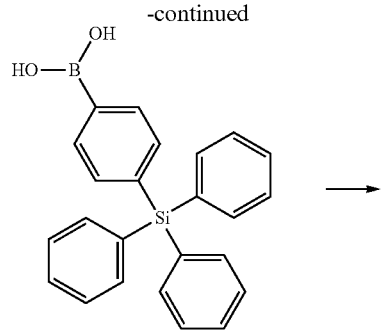

Compound 1

Sub 1 (10 g, 19.1 mmol) and (4-(triphenylsilyl) phenyl) boronic acid (7.3 g, 19.1 mmol) were added to 200 ml of tetrahydrofuran under a nitrogen atmosphere, and the mixture was stirred and refluxed. Then, potassium carbonate (7.9 g, 57.3 mmol) was dissolved in 8 ml of water, added thereto and sufficiently stirred, and then tetrakistriphenyl-phosphinopalladium (0.7 g, 0.6 mmol) was added. After the reaction for 1 hour, the reaction mixture was cooled to room temperature and then the organic layer and the aqueous layer were separated, and the organic layer was distilled. This was added again to 315 mL of chloroform, dissolved and washed twice with water. The organic layer was then separated, anhydrous magnesium sulfate was added, stirred and then filtered, and the filtrate was distilled under reduced pressure. The concentrated compound was recrystallized from chloroform and ethyl acetate to prepare a white solid compound 1 (9.9 g, 63%, MS: [M+H]$^+$=824.3).

Preparation Example 2: Preparation of Compound 2

Preparation Example 3: Preparation of Compound 3

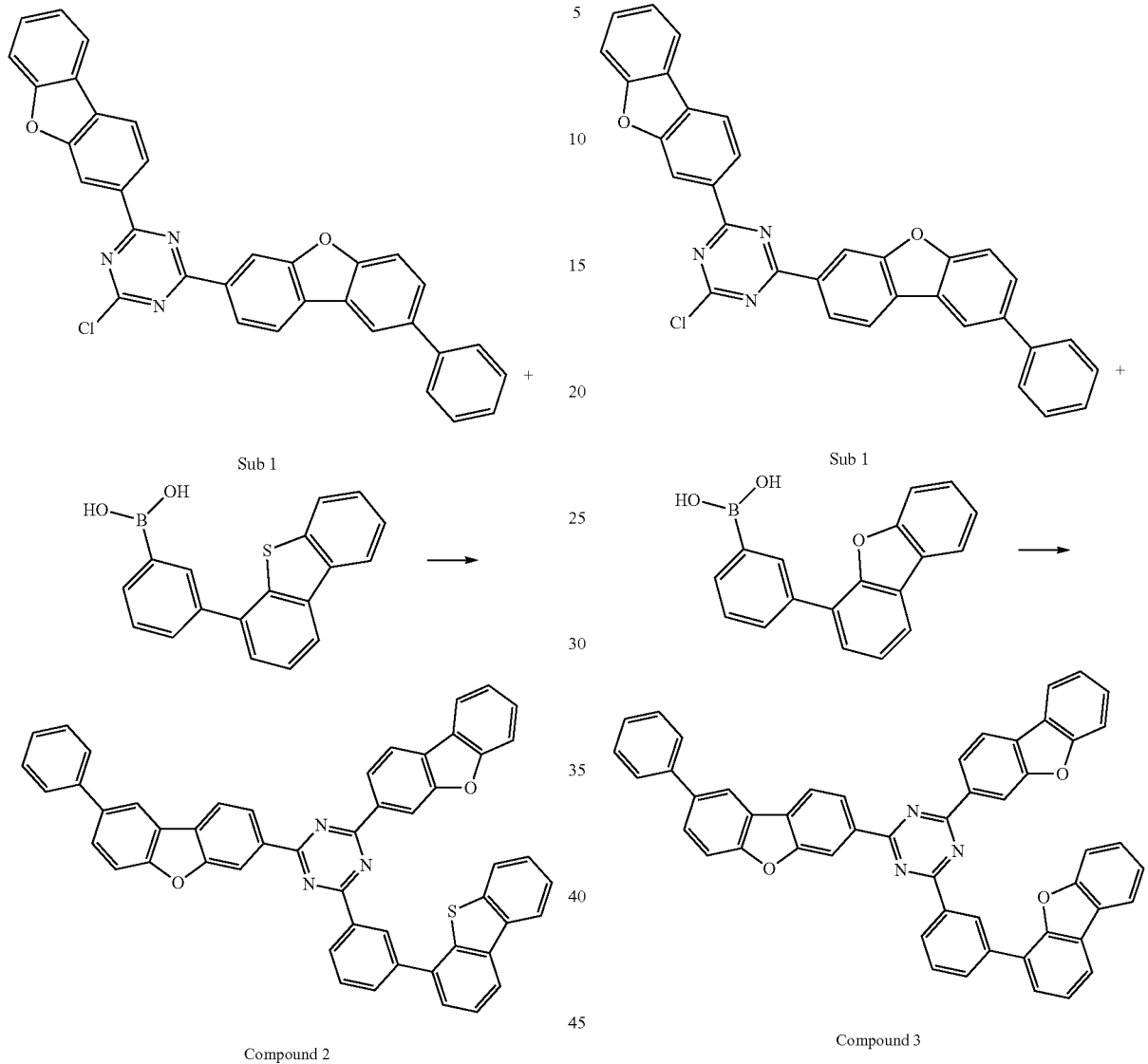

Sub 1 (10 g, 19.1 mmol) and (3-(dibenzo[b,d]thiophen-4-yl)phenyl)boronic acid (5.8 g, 19.1 mmol) were added to 200 ml of tetrahydrofuran under a nitrogen atmosphere, and the mixture was stirred and refluxed. Then, potassium carbonate (7.9 g, 57.3 mmol) was dissolved in 8 ml of water, added thereto and sufficiently stirred, and then tetrakistriphenyl-phosphinopalladium (0.7 g, 0.6 mmol) was added. After the reaction for 2 hours, the reaction mixture was cooled to room temperature and then the organic layer and the aqueous layer were separated, and the organic layer was distilled. This was added again to 286 mL of chloroform, dissolved and washed twice with water. The organic layer was then separated, anhydrous magnesium sulfate was added, stirred and then filtered, and the filtrate was distilled under reduced pressure. The concentrated compound was recrystallized from chloroform and ethyl acetate to prepare a yellow solid compound 2 (10 g, 70%, MS: [M+H]$^+$= 748.2).

Sub 1 (10 g, 19.1 mmol) and (3-(dibenzo[b,d]furan-4-yl)phenyl)boronic acid (5.5 g, 19.1 mmol) were added to 200 ml of tetrahydrofuran under a nitrogen atmosphere, and the mixture was stirred and refluxed. Then, potassium carbonate (7.9 g, 57.3 mmol) was dissolved in 8 ml of water, added thereto and sufficiently stirred, and then tetrakistriphenyl-phosphinopalladium (0.7 g, 0.6 mmol) was added. After the reaction for 1 hour, the reaction mixture was cooled to room temperature and then the organic layer and the aqueous layer were separated, and the organic layer was distilled. This was added again to 280 mL of chloroform, dissolved and washed twice with water. The organic layer was then separated, anhydrous magnesium sulfate was added, stirred and then filtered, and the filtrate was distilled under reduced pressure. The concentrated compound was recrystallized from chloroform and ethyl acetate to prepare a yellow solid compound 3 (9.5 g, 68%, MS: [M+H]$^+$=732.2).

Preparation Example 4: Preparation of Compound 4

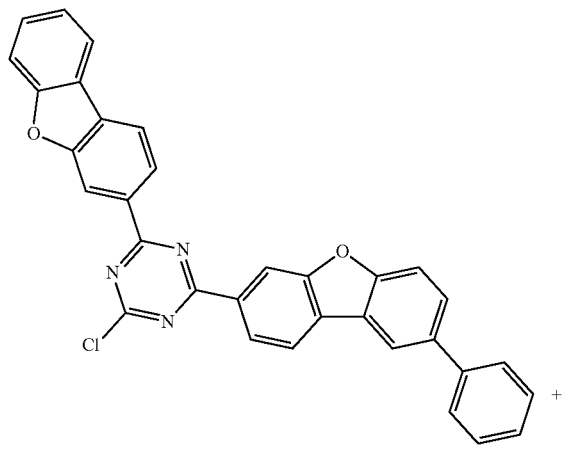

Compound 4

Preparation Example 5: Preparation of Compound 5

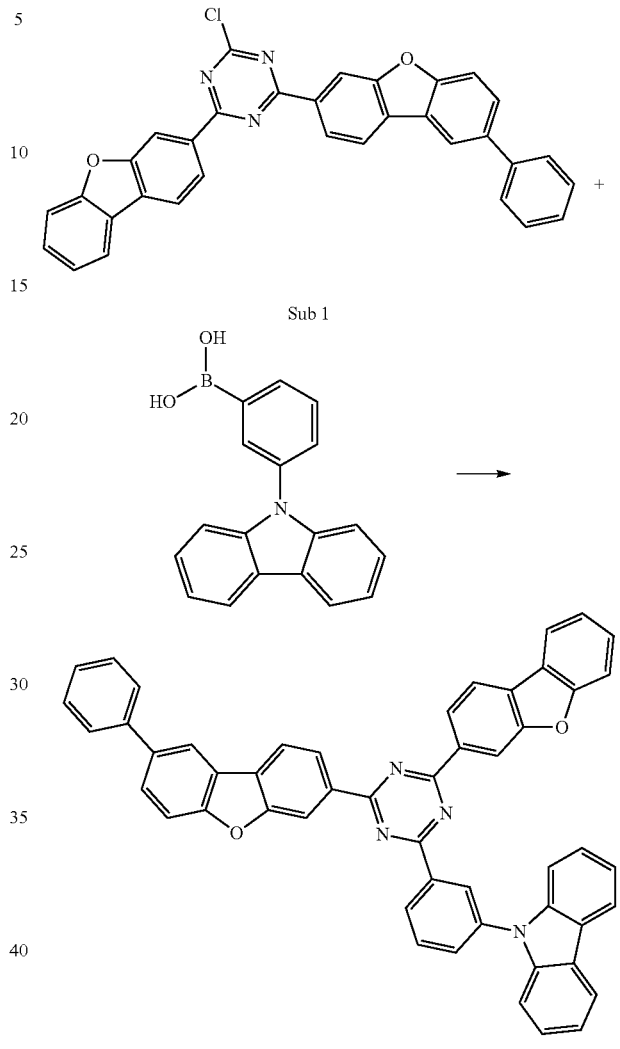

Compound 5

Sub 1 (10 g, 19.1 mmol) and (2-(9H-carbazol-9-yl) phenyl)boronic acid (5.5 g, 19.1 mmol) were added to 200 ml of tetrahydrofuran under a nitrogen atmosphere, and the mixture was stirred and refluxed. Then, potassium carbonate (7.9 g, 57.3 mmol) was dissolved in 9 ml of water, added thereto and sufficiently stirred, and then tetrakistriphenylphosphinopalladium (0.7 g, 0.6 mmol) was added. After the reaction for 1 hour, the reaction mixture was cooled to room temperature and then the organic layer and the aqueous layer were separated, and the organic layer was distilled. This was added again to 279 mL of chloroform, dissolved and washed twice with water. The organic layer was then separated, anhydrous magnesium sulfate was added, stirred and then filtered, and the filtrate was distilled under reduced pressure. The concentrated compound was recrystallized from chloroform and ethyl acetate to prepare a white solid compound 4 (10.2 g, 73%, MS: $[M+H]^+$=731.2).

Sub 1 (10 g, 19.1 mmol) and (3-(9H-carbazol-9-yl)phenyl)boronic acid (5.5 g, 19.1 mmol) were added to 200 ml of tetrahydrofuran under a nitrogen atmosphere, and the mixture was stirred and refluxed. Then, potassium carbonate (7.9 g, 57.3 mmol) was dissolved in 8 ml of water, added thereto and sufficiently stirred, and then tetrakistriphenylphosphinopalladium (0.7 g, 0.6 mmol) was added. After the reaction for 1 hour, the reaction mixture was cooled to room temperature and then the organic layer and the aqueous layer were separated, and the organic layer was distilled. This was added again to 279 mL of chloroform, dissolved and washed twice with water. The organic layer was then separated, anhydrous magnesium sulfate was added, stirred and then filtered, and the filtrate was distilled under reduced pressure. The concentrated compound was recrystallized from chloroform and ethyl acetate to prepare a white solid compound 5 (11.3 g, 81%, MS: $[M+H]^+$=731.2).

Preparation Example 6: Preparation of Compound 6

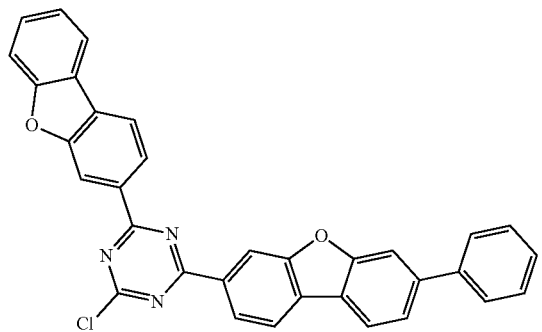

Sub 2

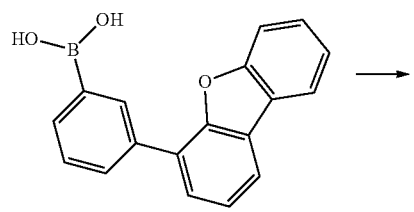

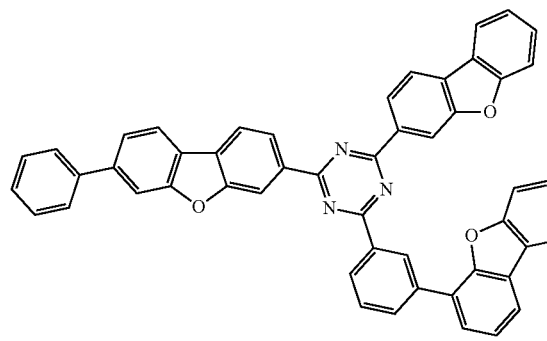

Compound 6

Sub 2 (10 g, 19.1 mmol) and (3-(dibenzo[b,d]furan-4-yl)phenyl)boronic acid (5.5 g, 19.1 mmol) were added to 200 ml of tetrahydrofuran under a nitrogen atmosphere, and the mixture was stirred and refluxed. Then, potassium carbonate (7.9 g, 57.3 mmol) was dissolved in 8 ml of water, added thereto and sufficiently stirred, and then tetrakistriphenylphosphinopalladium (0.7 g, 0.6 mmol) was added. After the reaction for 1 hour, the reaction mixture was cooled to room temperature and then the organic layer and the aqueous layer were separated, and the organic layer was distilled. This was added again to 280 mL of chloroform, dissolved and washed twice with water. The organic layer was then separated, anhydrous magnesium sulfate was added, stirred and then filtered, and the filtrate was distilled under reduced pressure. The concentrated compound was recrystallized from chloroform and ethyl acetate to prepare a yellow solid compound 6 (9.8 g, 70%, MS: [M+H]$^+$=732.2).

Preparation Example 7: Preparation of Compound 7

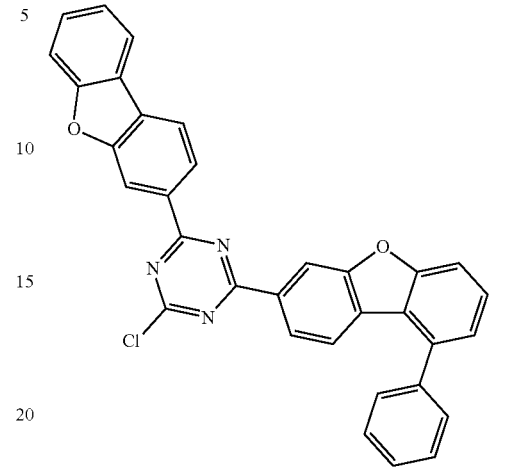

Sub 3

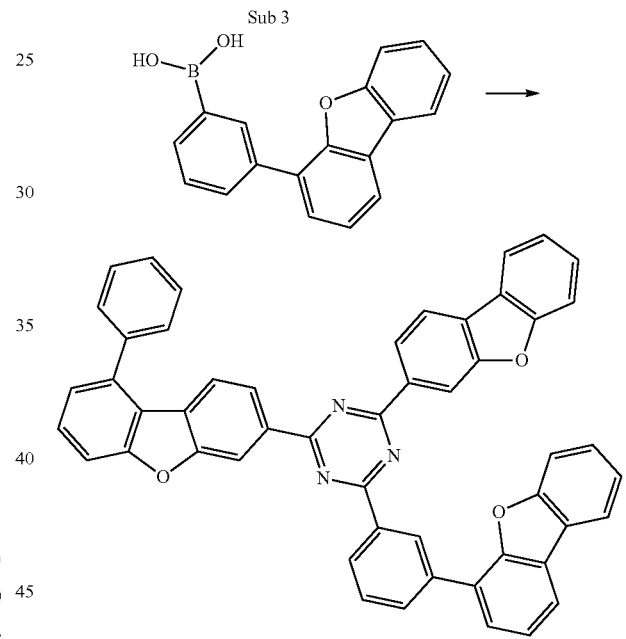

Compound 7

Sub 3 (10 g, 19.1 mmol) and (3-(dibenzo[b,d]furan-4-yl)phenyl)boronic acid (5.5 g, 19.1 mmol) were added to 200 ml of tetrahydrofuran under a nitrogen atmosphere, and the mixture was stirred and refluxed. Then, potassium carbonate (7.9 g, 57.3 mmol) was dissolved in 8 ml of water, added thereto and sufficiently stirred, and then tetrakistriphenylphosphinopalladium (0.7 g, 0.6 mmol) was added. After the reaction for 1 hour, the reaction mixture was cooled to room temperature and then the organic layer and the aqueous layer were separated, and the organic layer was distilled. This was added again to 280 mL of chloroform, dissolved and washed twice with water. The organic layer was then separated, anhydrous magnesium sulfate was added, stirred and then filtered, and the filtrate was distilled under reduced pressure. The concentrated compound was recrystallized from chloroform and ethyl acetate to prepare a yellow solid compound 7 (9.8 g, 70%, MS: [M+H]$^+$=732.2).

Preparation Example 8: Preparation of Compound 8

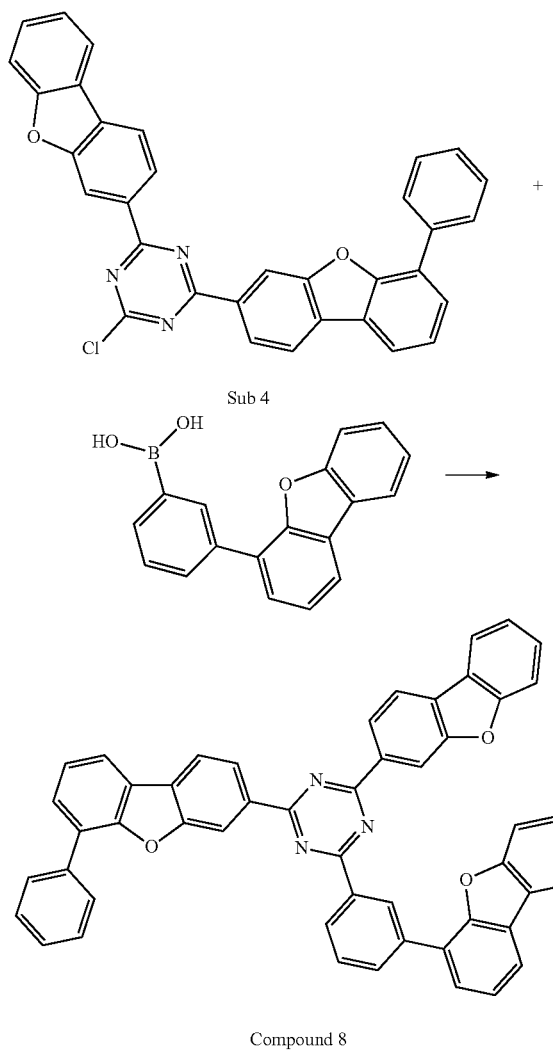

Sub 4

Compound 8

Sub 4 (10 g, 19.1 mmol) and (3-(dibenzo[b,d]furan-4-yl) phenyl)boronic acid (5.5 g, 19.1 mmol) were added to 200 ml of tetrahydrofuran under a nitrogen atmosphere, and the mixture was stirred and refluxed. Then, potassium carbonate (0.7 g, 0.6 mmol) was dissolved in 8 ml of water, added thereto and sufficiently stirred, and then tetrakistriphenylphosphinopalladium (0.7 g, 0.6 mmol) was added. After the reaction for 1 hour, the reaction mixture was cooled to room temperature and then the organic layer and the aqueous layer were separated, and the organic layer was distilled. This was added again to 280 mL of chloroform, dissolved and washed twice with water. The organic layer was then separated, anhydrous magnesium sulfate was added, stirred and then filtered, and the filtrate was distilled under reduced pressure. The concentrated compound was recrystallized from chloroform and ethyl acetate to prepare a yellow solid compound 8 (7.1 g, 51%, MS: $[M+H]^+=732.2$).

EXPERIMENTAL EXAMPLES

Example 1

A glass substrate on which ITO (indium tin oxide) was coated as a thin film to a thickness of 1300 Å was put into distilled water in which a detergent was dissolved, and ultrasonically cleaned. At this time, a product manufactured by Fischer Co. was used as the detergent, and as the distilled water, distilled water filtered twice using a filter manufactured by Millipore Co. was used. After the ITO was cleaned for 30 minutes, ultrasonic cleaning was repeated twice using distilled water for 10 minutes. After the cleaning with distilled water was completed, the substrate was ultrasonically cleaned with solvents of isopropyl alcohol, acetone and methanol, dried, and then transferred to a plasma cleaner. In addition, the substrate was cleaned for 5 minutes using oxygen plasma and then transferred to a vacuum depositor.

On the transparent ITO electrode thus prepared, the following HI-1 was thermally vacuum deposited to a thickness of 50 Å to form a hole injection layer. The following compound HT-1 was thermally vacuum-deposited on the hole injection layer to a thickness of 250 Å to form a hole transport layer, and the following compound HT-2 was vacuum-deposited on the HT-1 deposited layer to a thickness of 50 Å to form an electron blocking layer. The compound 1 prepared in the previous Preparation Example 1, the following compound YGH-1, and a phosphorescent dopant YGD-1 were co-deposited in a weight ratio of 44:44:12 on the HT-2 deposited layer to form a light emitting layer with a thickness of 400 Å. The following compound ET-1 was vacuum-deposited on the light emitting layer to a thickness of 250 Å to form an electron transport layer, and the following compound ET-2 and U were vacuum-deposited in a weight ratio of 98:2 on the electron transport layer to form an electron injection layer with a thickness of 100 Å. Aluminum was deposited on the electron injection layer to a thickness of 1000 Å to form a cathode.

HI-1

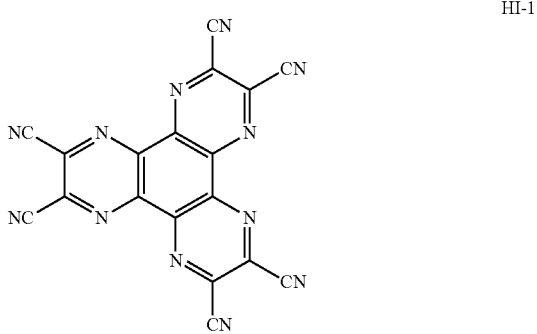

HT-1

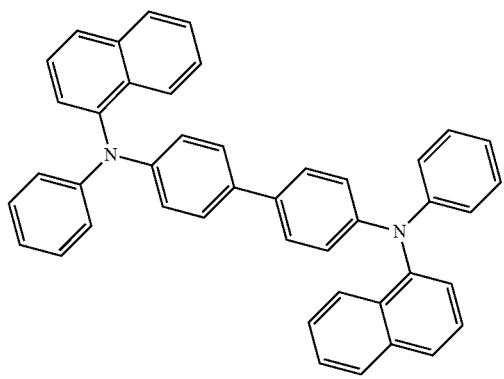

HT-2

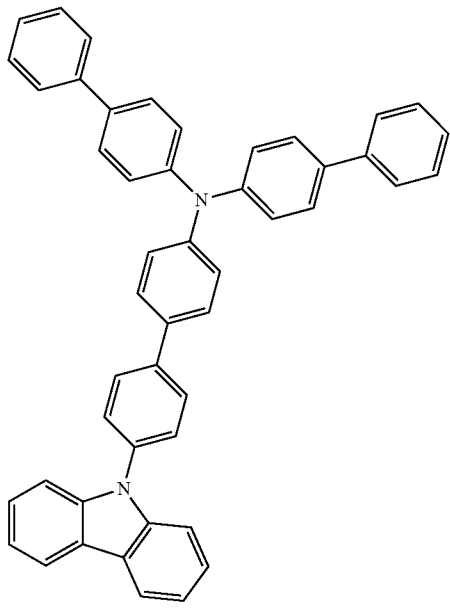

YGH-1

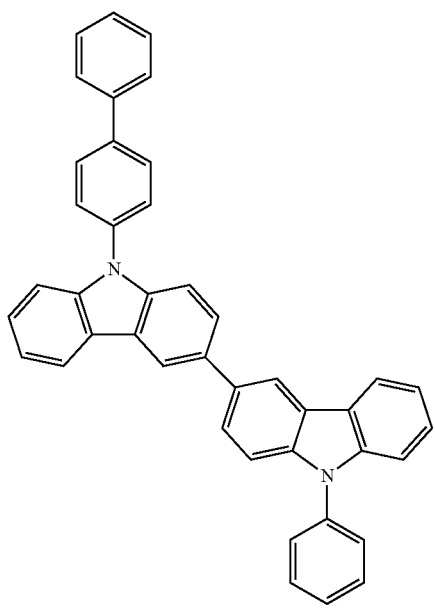

YGD-1

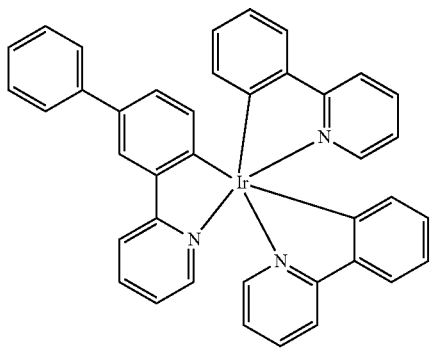

ET-1

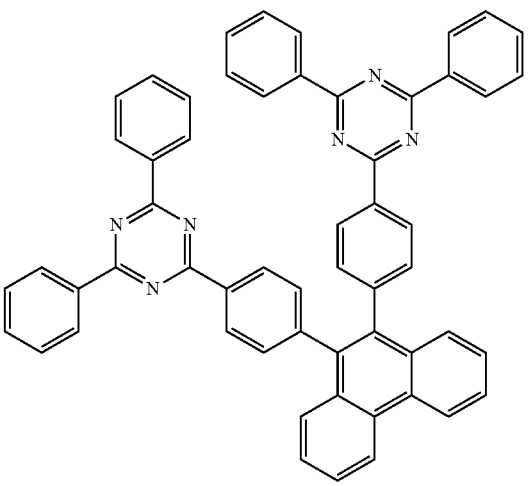

ET-2

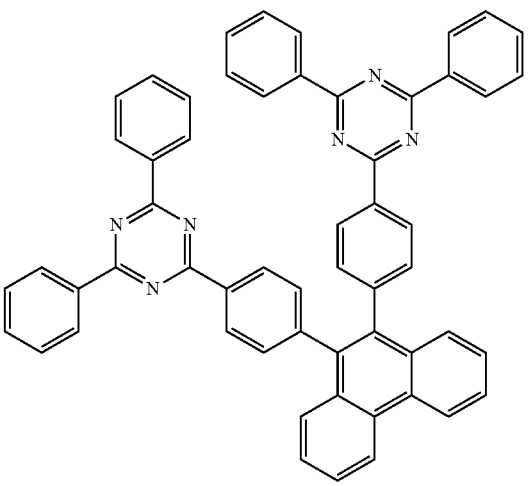

In they above-mentioned process, the vapor deposition rate of the organic material was maintained at 0.4 to 0.7 Å/sec, the deposition rate of aluminum was maintained at 2 Å/sec, and the degree of vacuum during the deposition was maintained at $1 \times 10^{-7}$ to $5 \times 10^{-8}$ torr.

Experimental Examples 2 to 8

An organic light emitting device was manufactured in the same manner as in Experimental Example 1, except that the compounds shown in Table 1 below were used instead of Compound 1 of Preparation Example 1 in Experimental Example 1.

Comparative Experimental Examples 1 to 3

An organic light emitting device was manufactured in the same manner as in Experimental Example 1, except that the compounds shown in Table 1 below were used instead of Compound 1 of Preparation Example 1 in Experimental Example 1. The compounds of CE1 to CE3 shown in Table 1 are as follows.

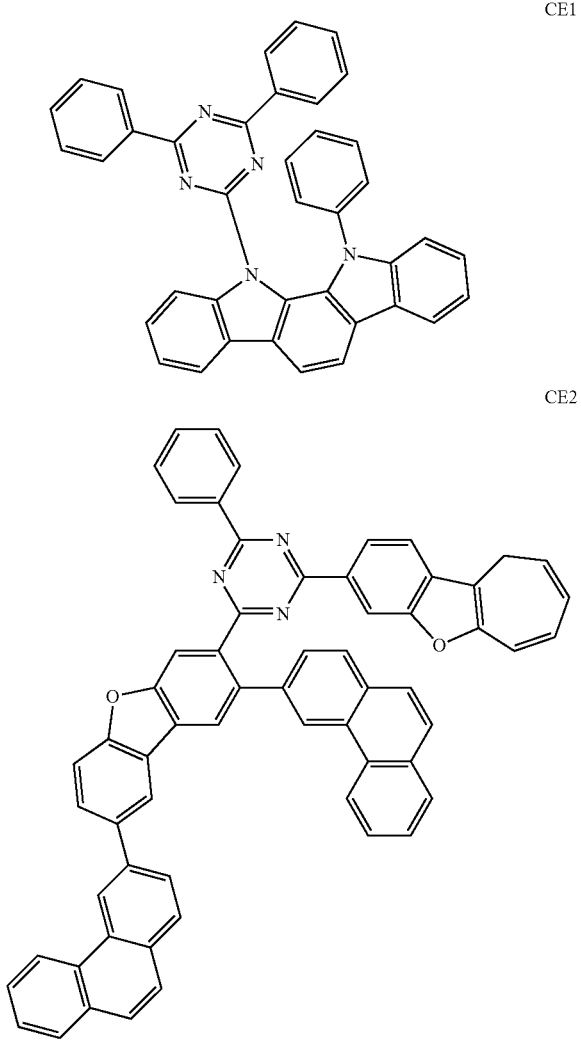

CE1

CE2

CE3

For the organic light emitting devices manufactured in Experimental Examples and Comparative Experimental Examples, the voltage and efficiency were measured at a current density of 10 mA/cm² and the lifetime was measured at a current density of 50 mA/cm². The results are shown in Table 1 below. In this case, $LT_{95}$ means the time required for the luminance to be reduced to 95% of the initial luminance.

TABLE 1

| | Compound | Voltage (V) (@10 mA/cm²) | Efficiency (Cd/A) (@10 mA/cm²) | Color coordinate (x, y) | Lifetime (h) ($LT_{95}$ at 50 mA/cm²) |
|---|---|---|---|---|---|
| Experimental Example 1 | Compound 1 | 3.8 | 82 | 0.45, 0.53 | 170 |
| Experimental Example 2 | Compound 2 | 4.2 | 78 | 0.45, 0.54 | 210 |
| Experimental Example 3 | Compound 3 | 4.1 | 80 | 0.46, 0.53 | 163 |
| Experimental Example 4 | Compound 4 | 4.1 | 79 | 0.46, 0.54 | 222 |
| Experimental Example 5 | Compound 5 | 4.1 | 79 | 0.46, 0.53 | 182 |
| Experimental Example 6 | Compound 6 | 4.2 | 78 | 0.46, 0.54 | 203 |
| Experimental Example 7 | Compound 7 | 4.3 | 82 | 0.46, 0.54 | 156 |
| Experimental Example 8 | Compound 8 | 4.2 | 83 | 0.46, 0.54 | 139 |
| Comparative Experimental Example 1 | CE1 | 4.3 | 79 | 0.46, 0.54 | 77 |
| Comparative Experimental Example 2 | CE2 | 4.5 | 70 | 0.46, 0.55 | 34 |
| Comparative Experimental Example 3 | CE3 | 4.2 | 74 | 0.46, 0.55 | 129 |

As shown in Table 1, it was confirmed that when the compound of the present disclosure was used as an organic light emitting layer material, it exhibited excellent characteristics in terms of efficiency and lifetime as compared with Comparative Experimental Examples.

This result is considered to be due to increased electrical stability caused by substitution of the triazine group by the dibenzofuran substituent. In addition, when an aryl substituent is further substituted in the dibenzofuran group, it has an asymmetric structure and also increases efficiency and lifetime due to the effect of inhibiting crystallinity in the thin film when the device is mounted.

DESCRIPTION OF REFERENCE NUMERALS

| | |
|---|---|
| 1: substrate | 2: anode |
| 3: light emitting layer | 4: cathode |
| 5: hole injection layer | 6: hole transport layer |
| 7: electron blocking layer | 8: electron transport layer |
| 9: electron injection layer | |

The invention claimed is:
1. A compound represented by Chemical Formula 1-1:

[Chemical Formula 1-1]

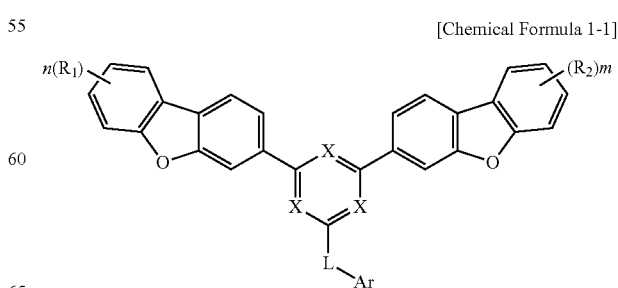

wherein in Chemical Formula 1-1,

X is each independently N or CH, and at least one of X is N, n is an integer of 1 to 3, and m is 0, $R_1$ and $R_2$ are each independently a substituted or unsubstituted $C_{6-10}$ aryl, L is a substituted or unsubstituted $C_{6-60}$ arylene, and Ar is a substituted or unsubstituted $C_{5-60}$ heteroaryl containing any one or more heteroatoms selected from the group consisting of N, O and S, or tri($C_{6-60}$ aryl)silyl.

2. The compound of claim 1, wherein n is 1 or 2.

3. The compound of claim 1, wherein $R_1$ is phenyl.

4. The compound of claim 1, wherein all of X are N.

5. The compound of claim 1, wherein L is phenylene.

6. The compound of claim 1, wherein Ar is any one selected from the group consisting of:

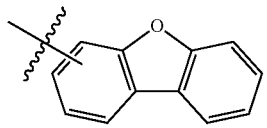

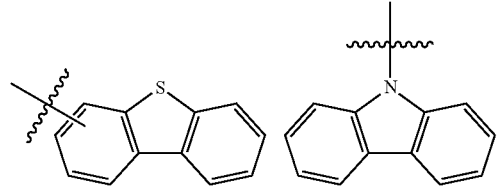

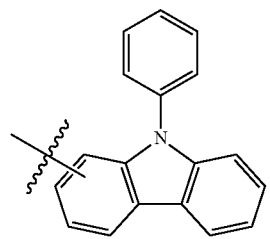

7. The compound of claim 1, wherein the compound represented by Chemical Formula 1-1 is any one selected from the group consisting of the following:

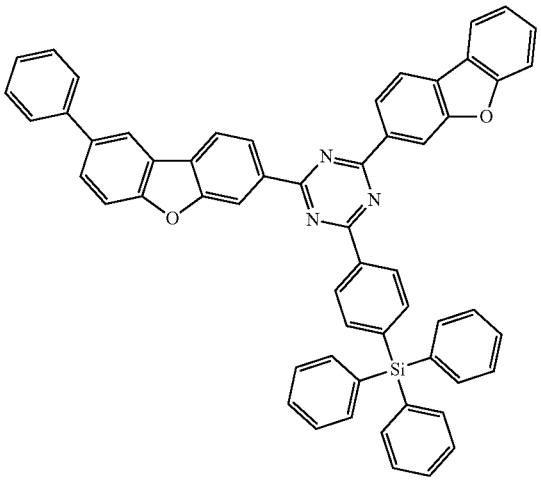

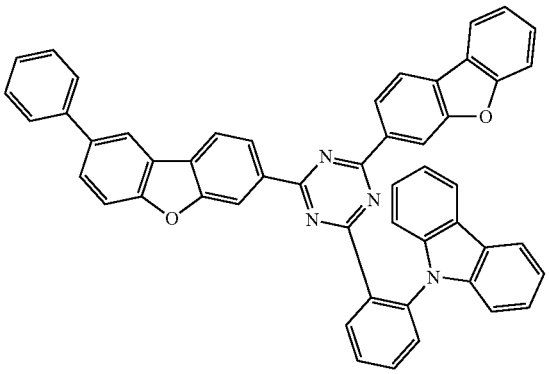

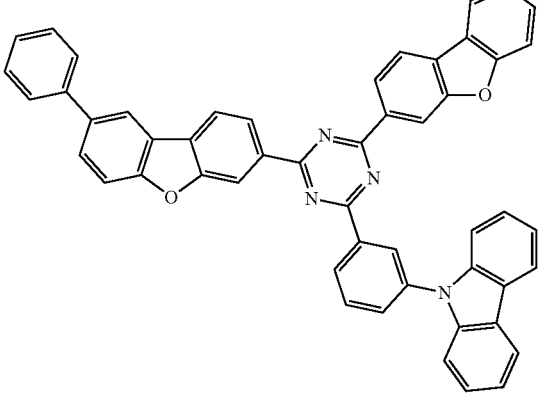

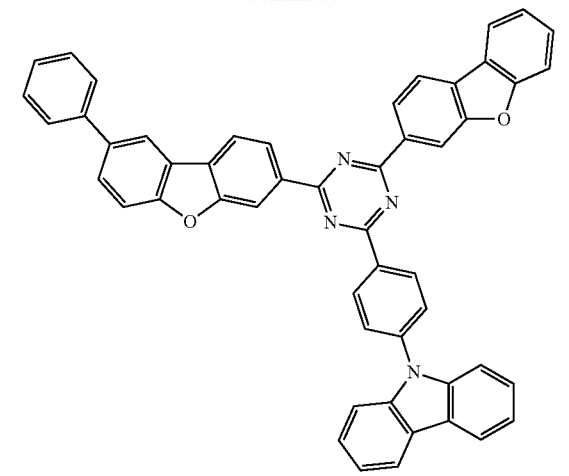
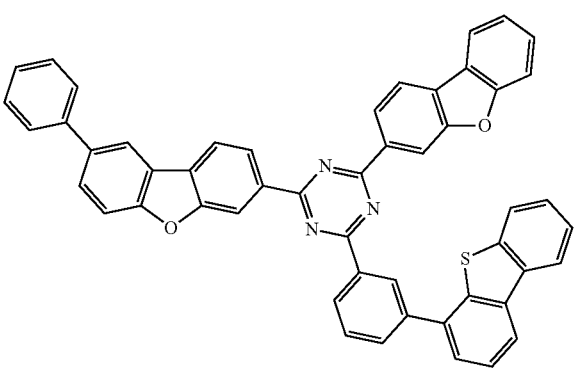
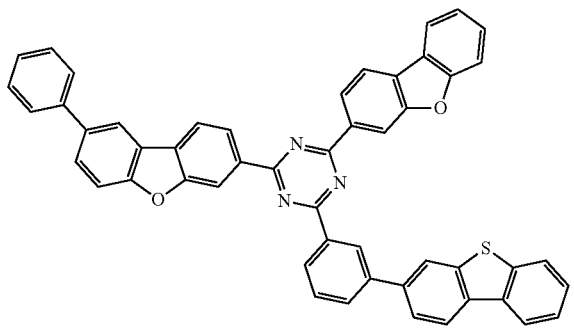
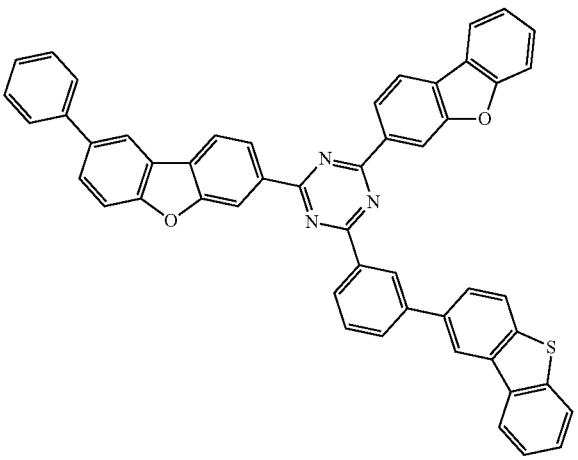
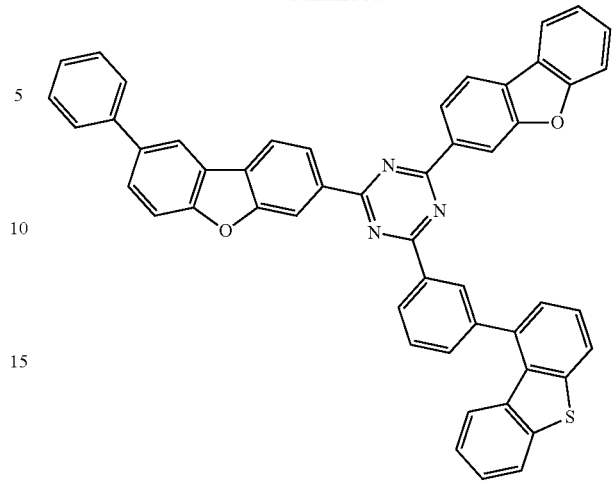
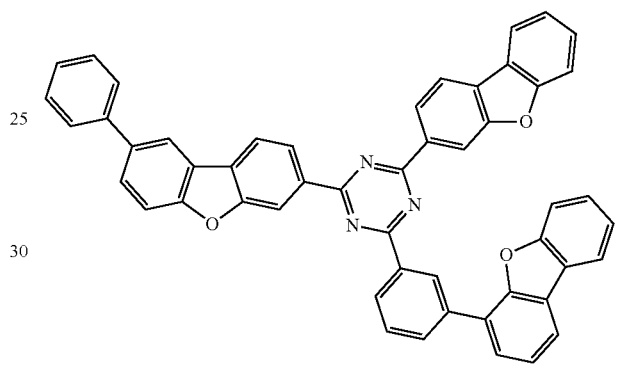
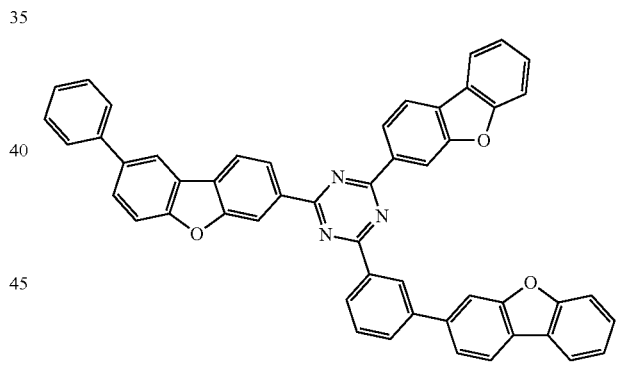
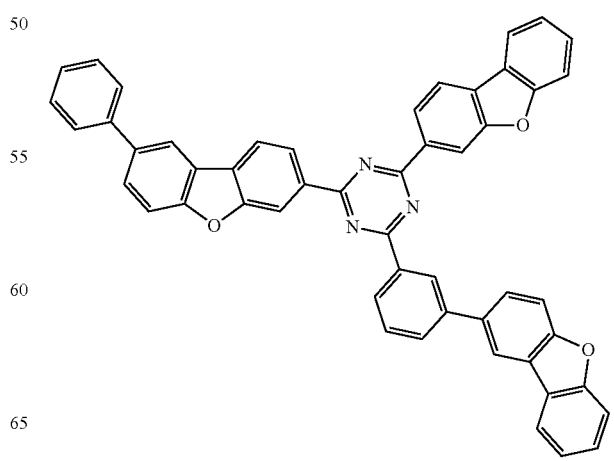

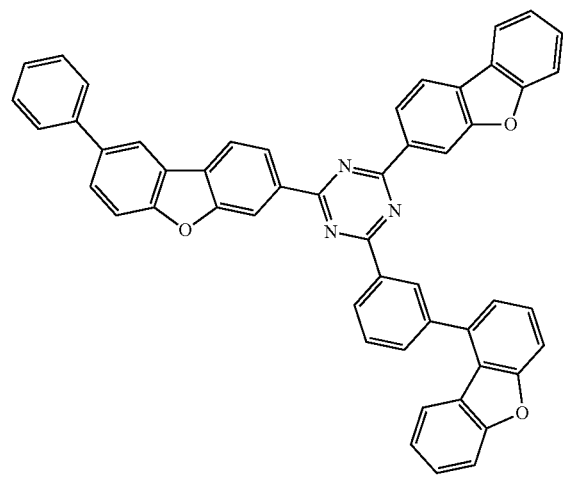
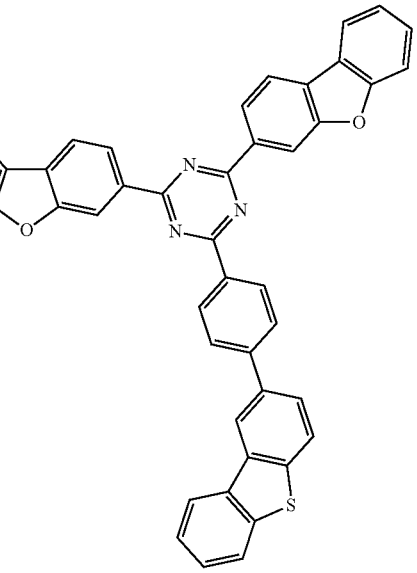
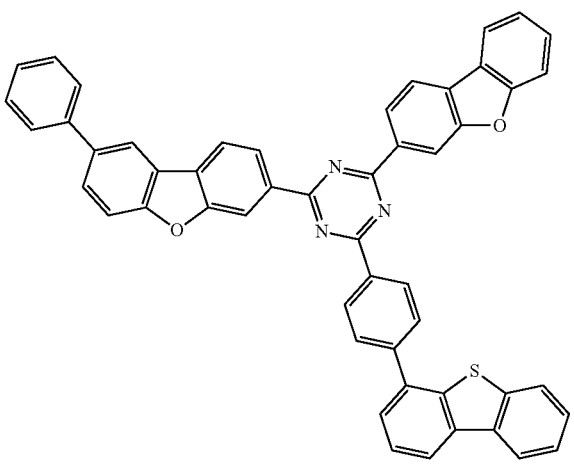
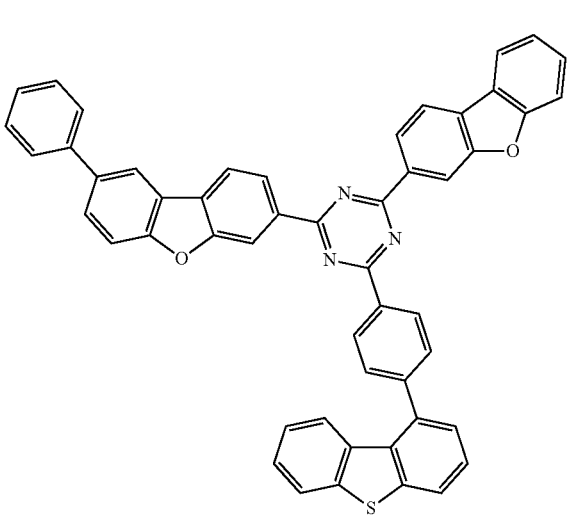
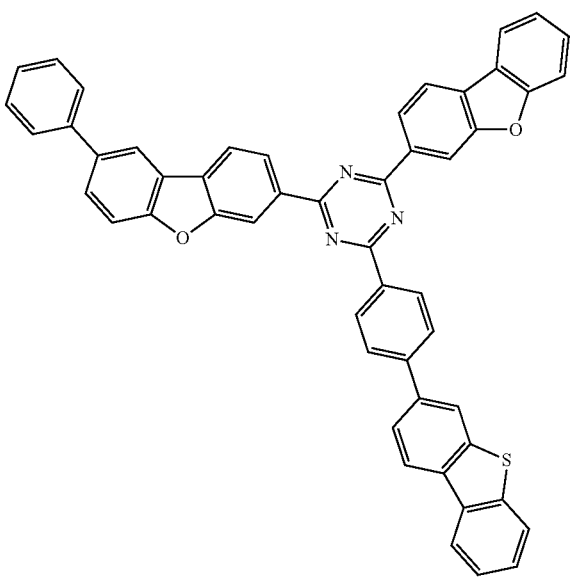
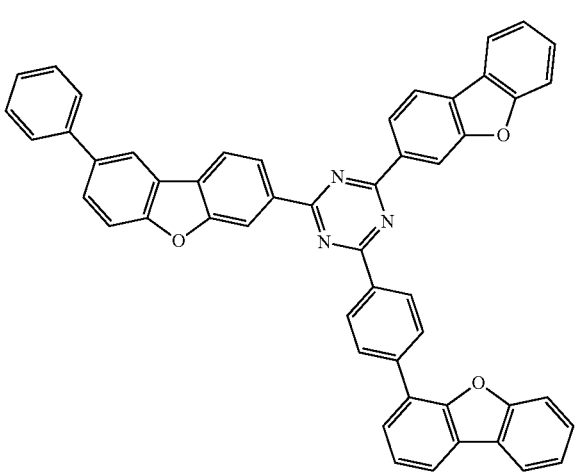

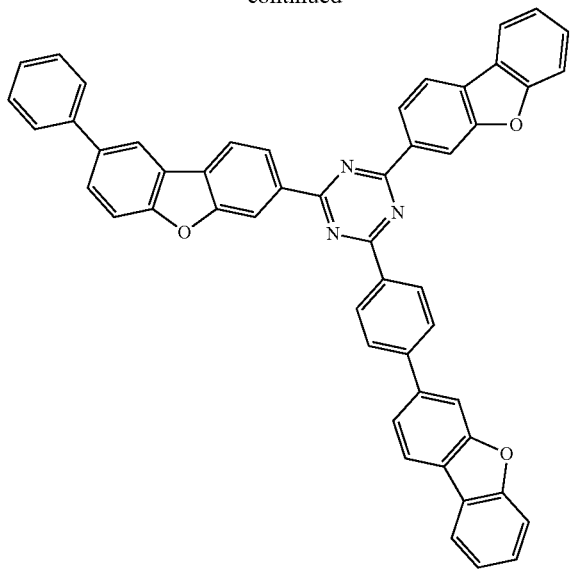
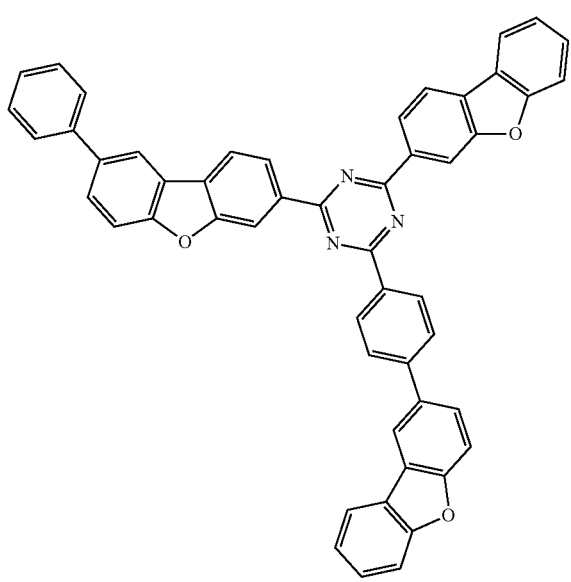
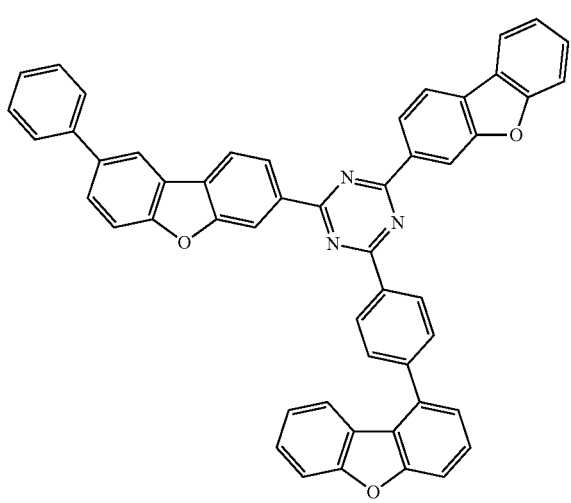
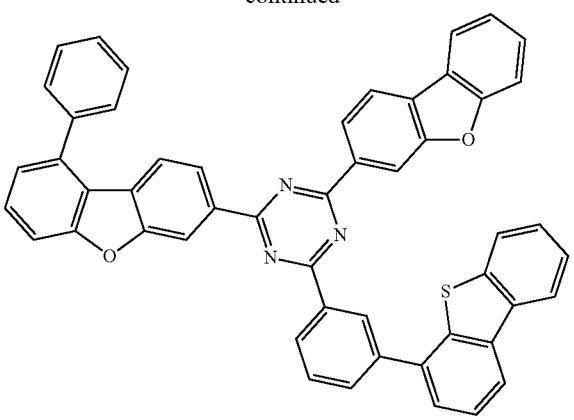
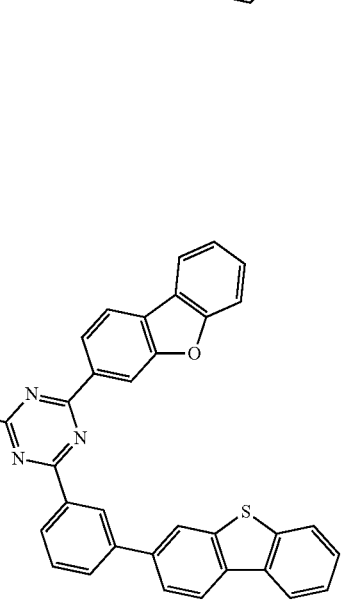
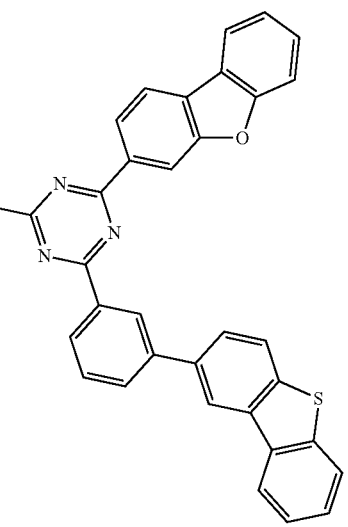

73
-continued
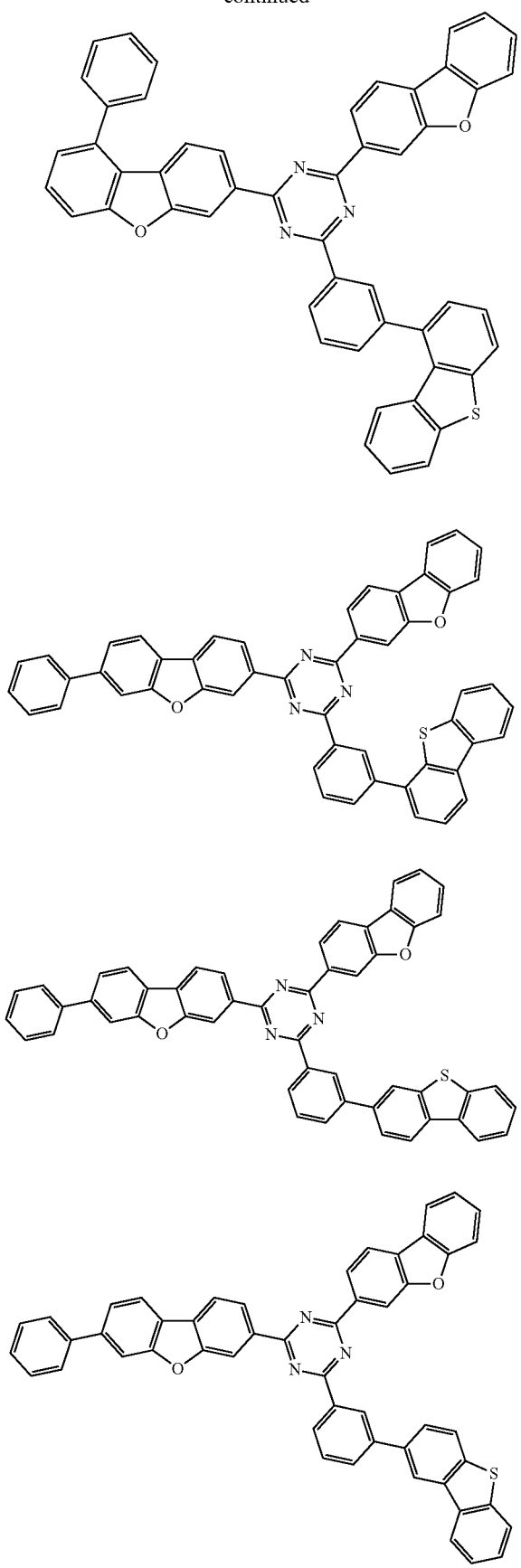
74
-continued
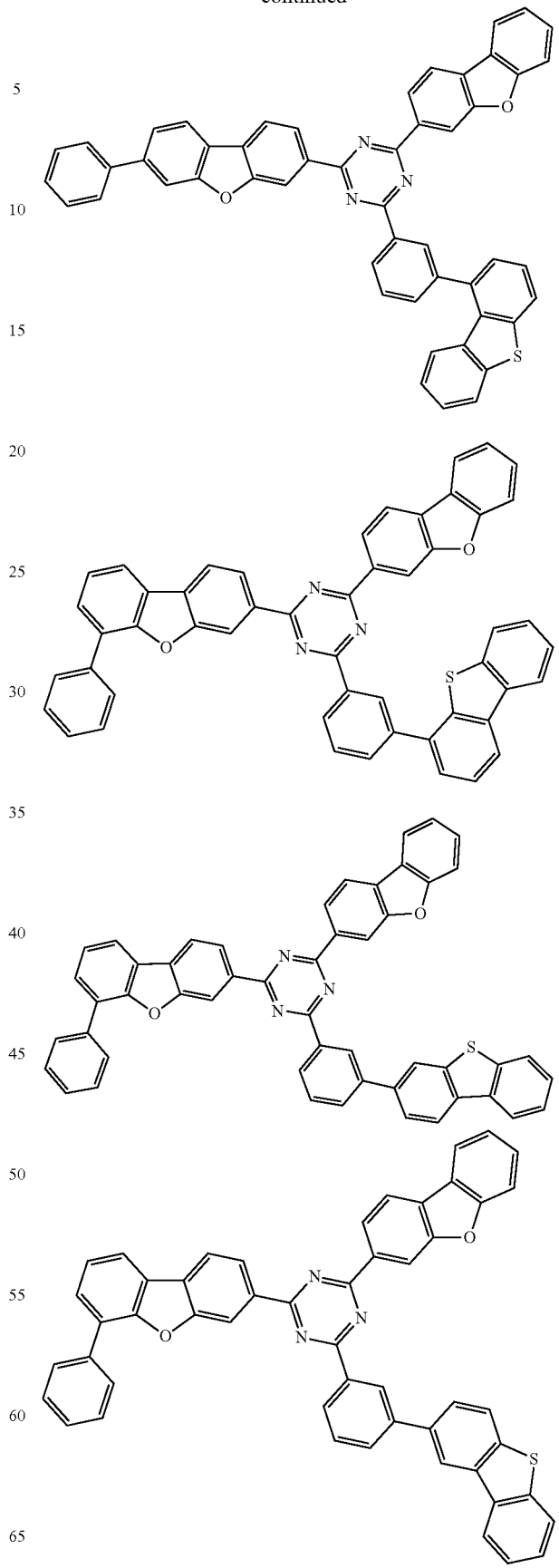

75
-continued
76
-continued
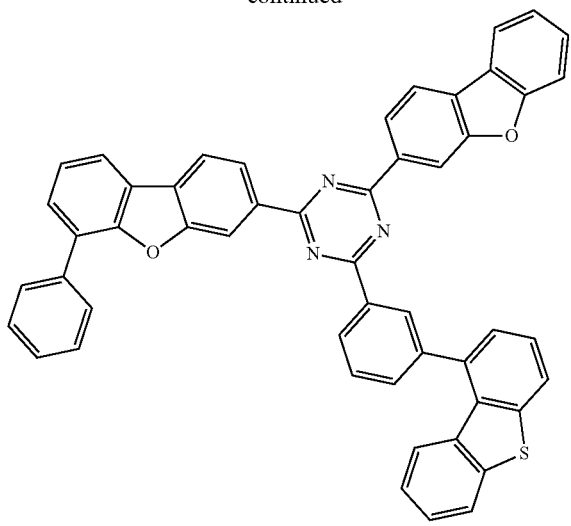
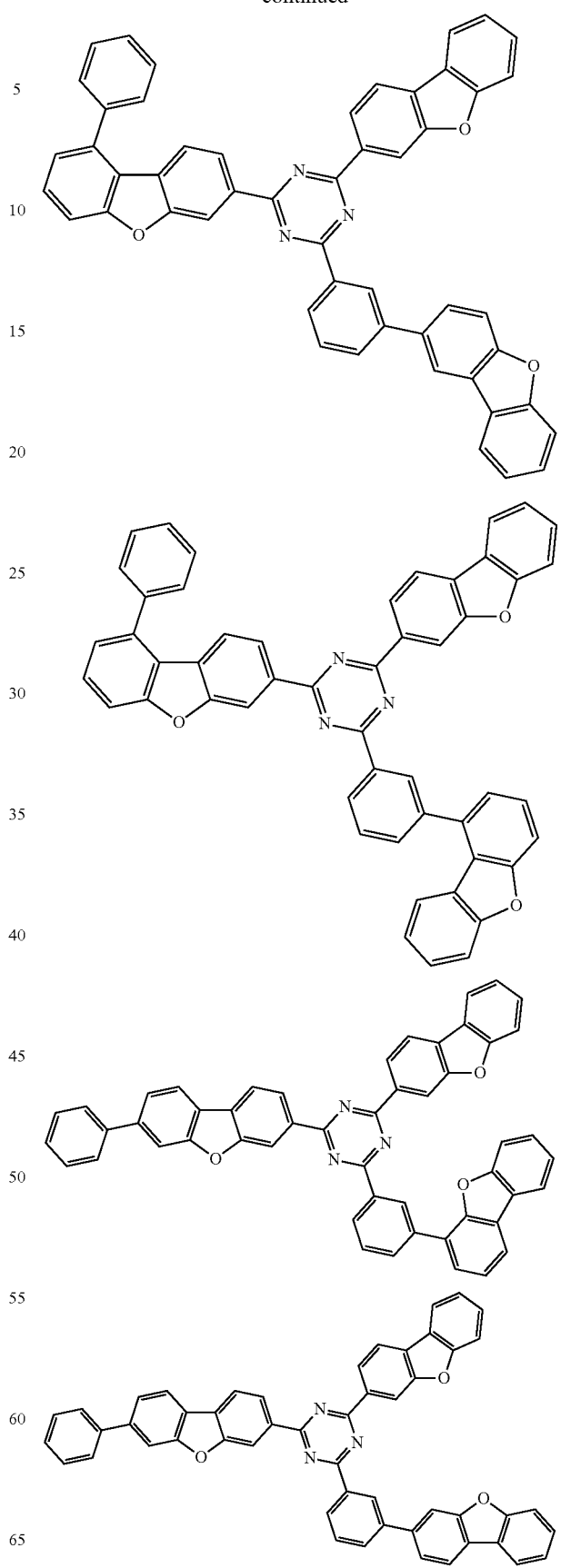

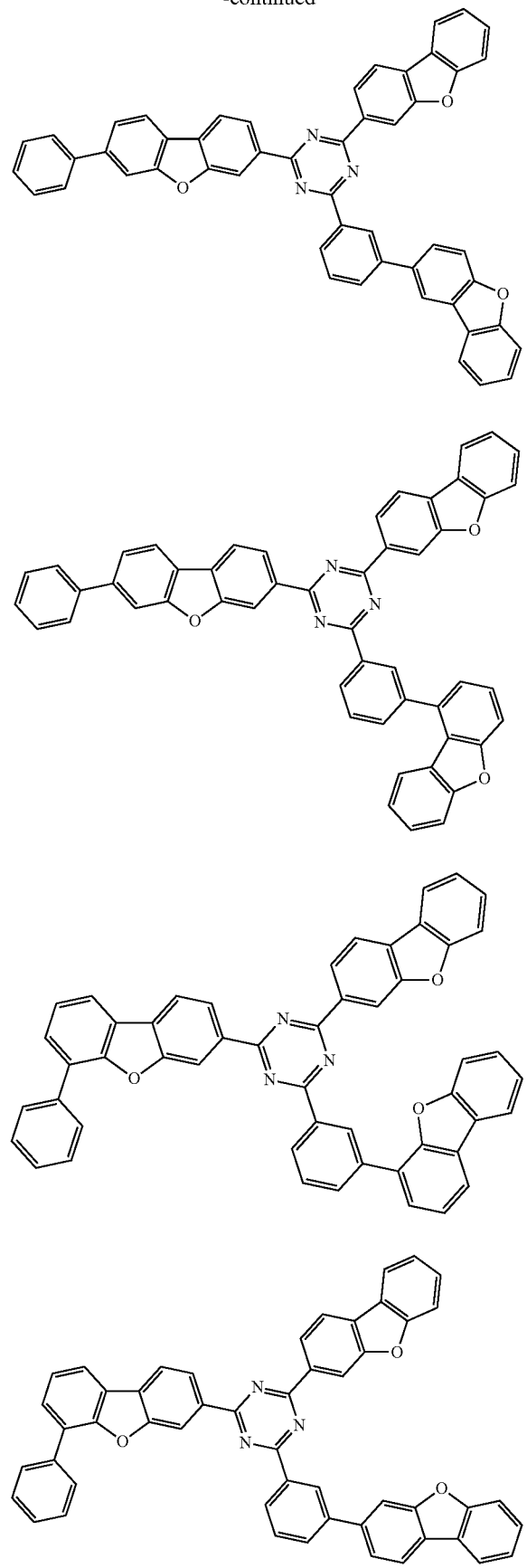
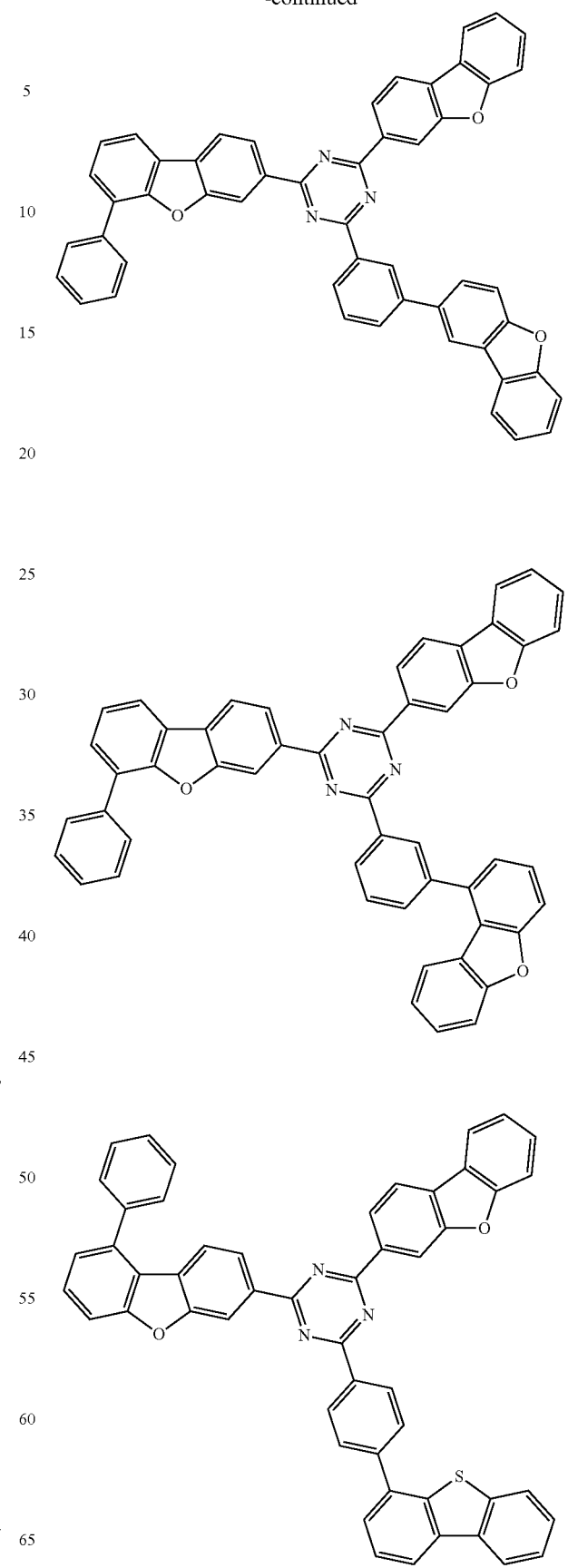

79
-continued
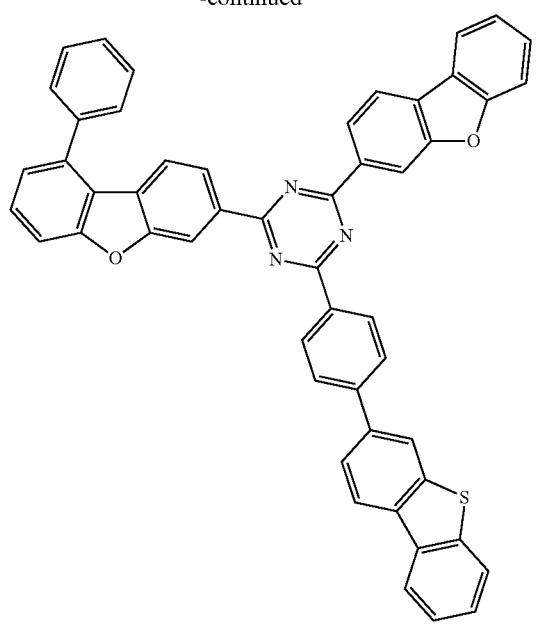
80
-continued
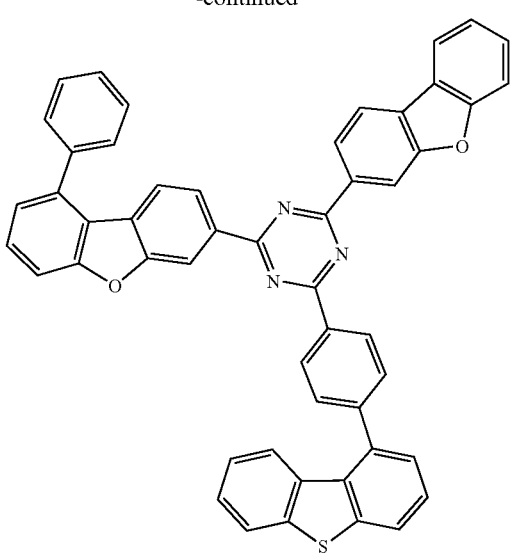
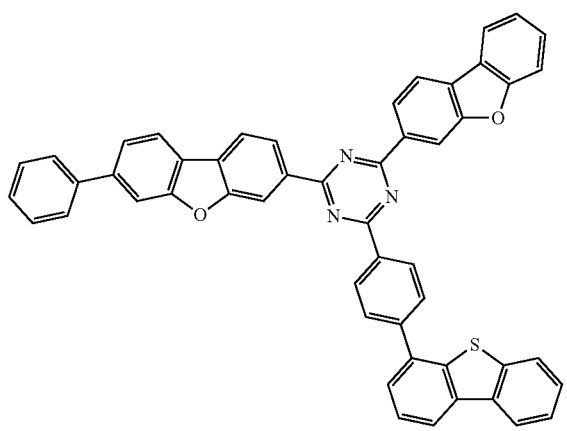
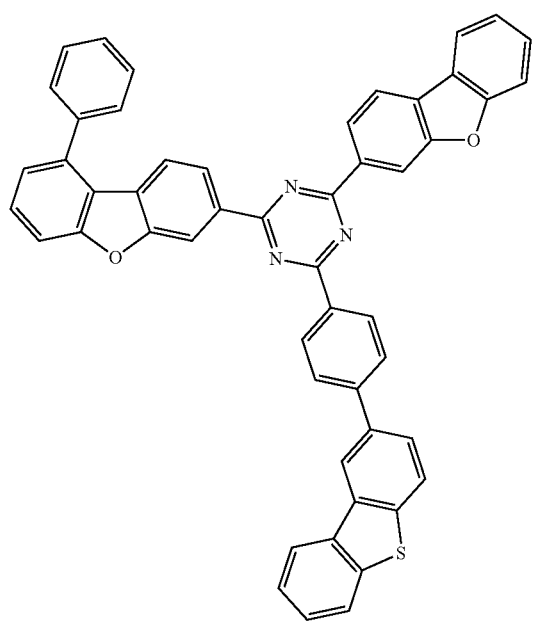

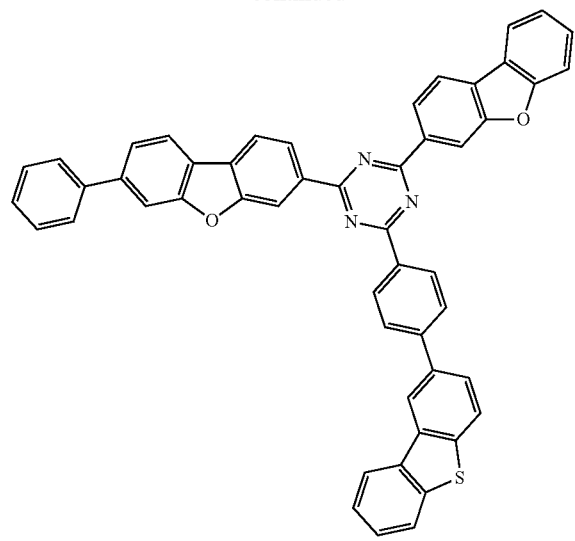
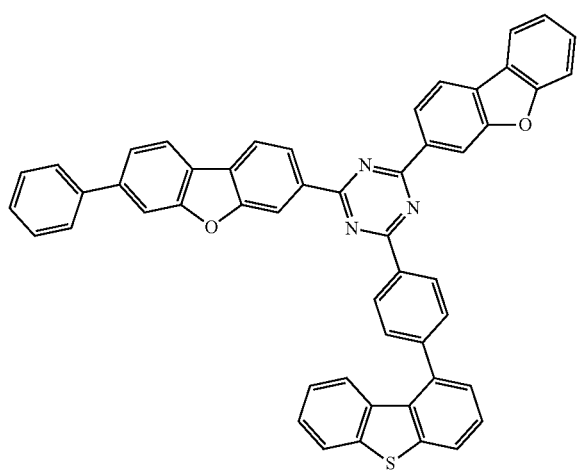
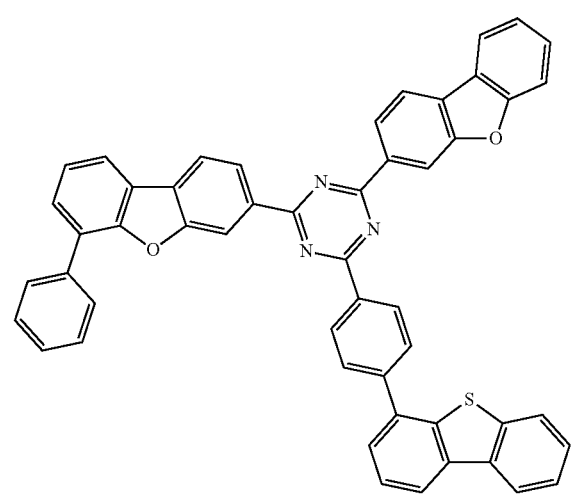
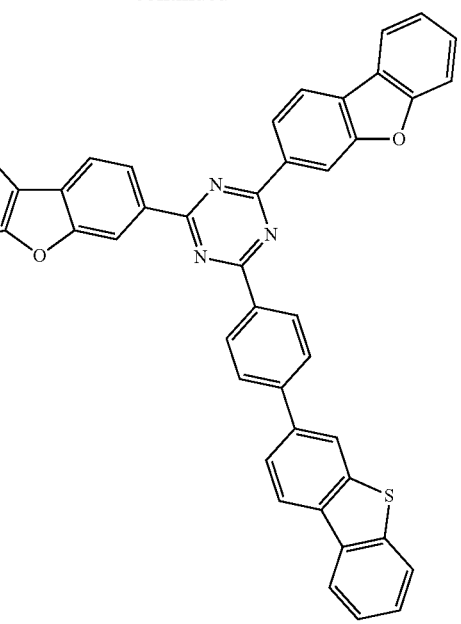
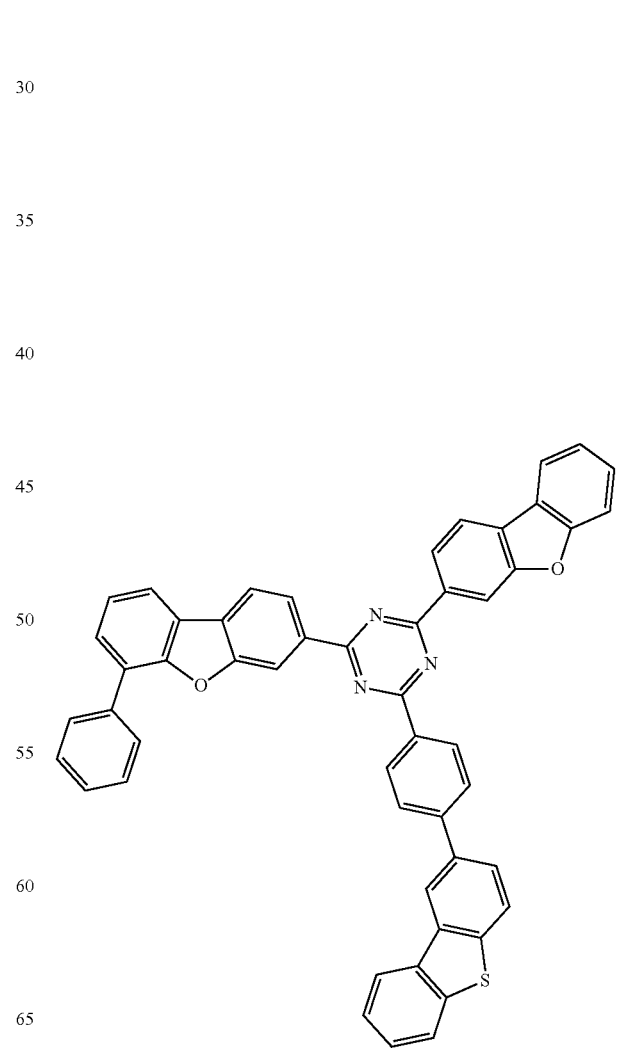

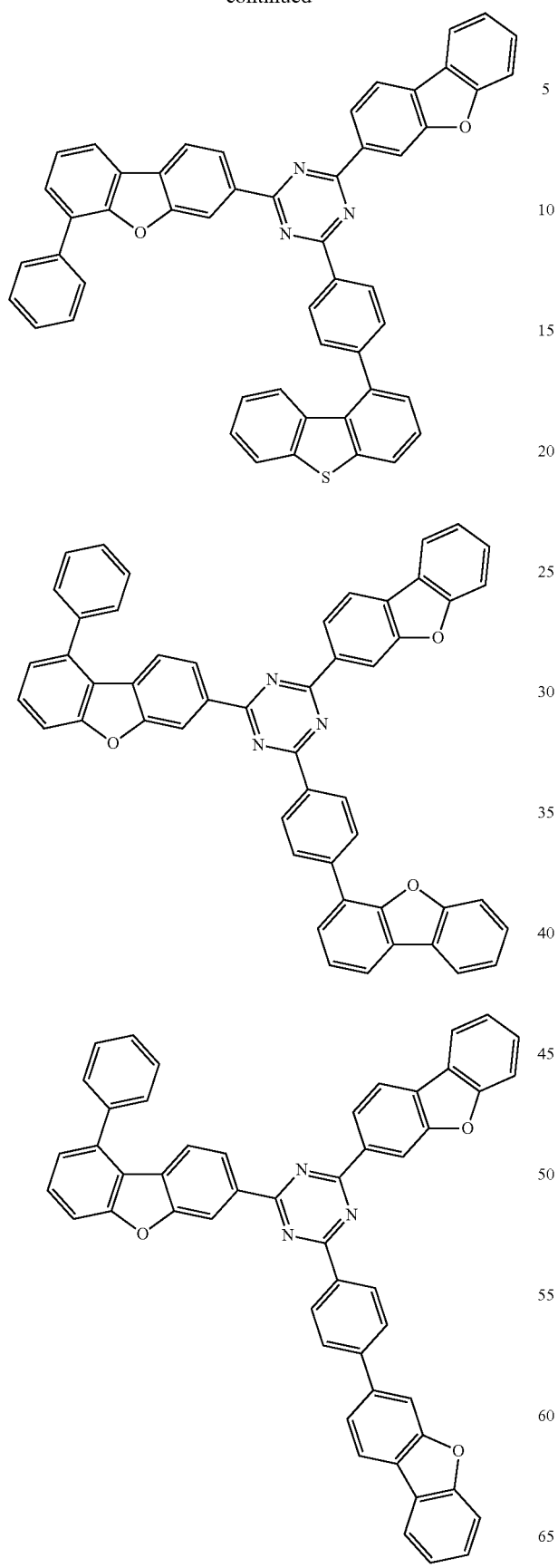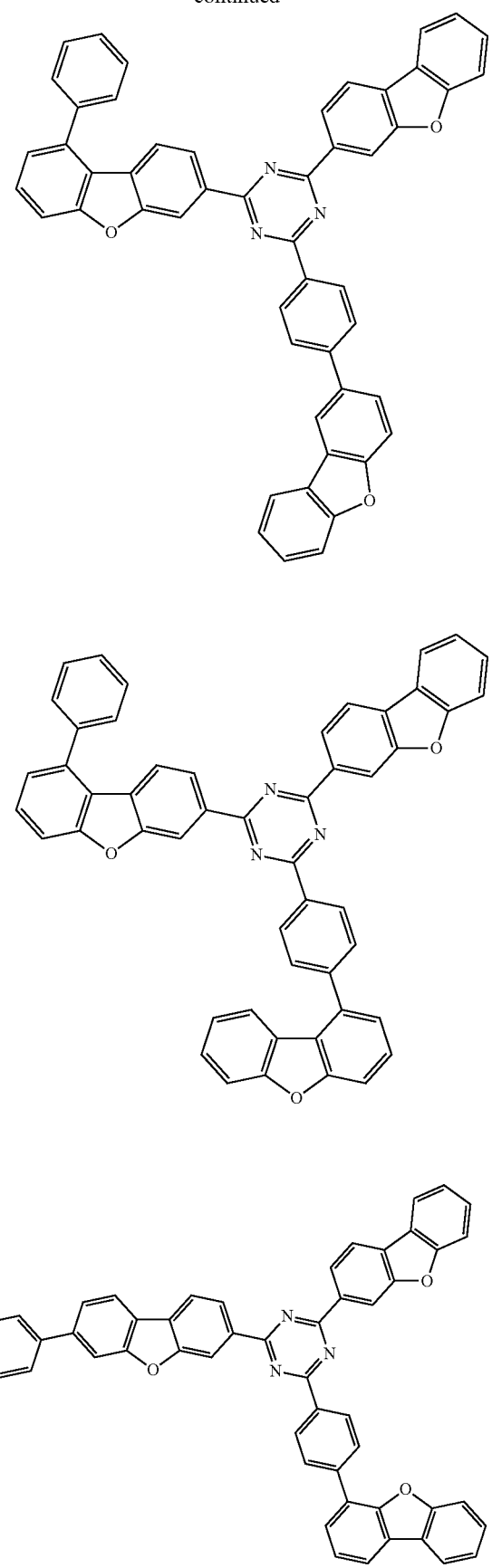

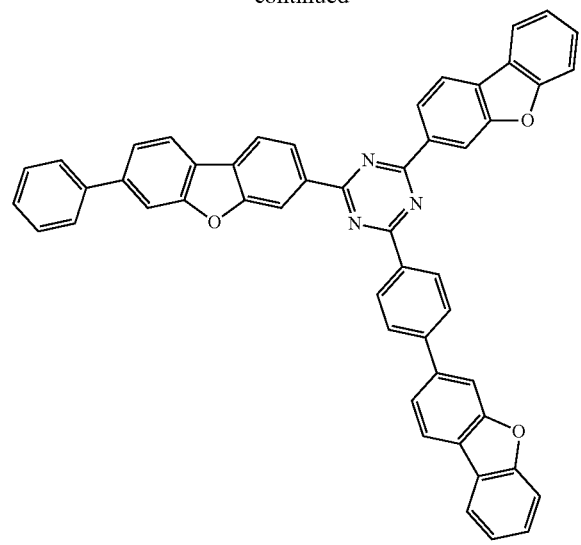
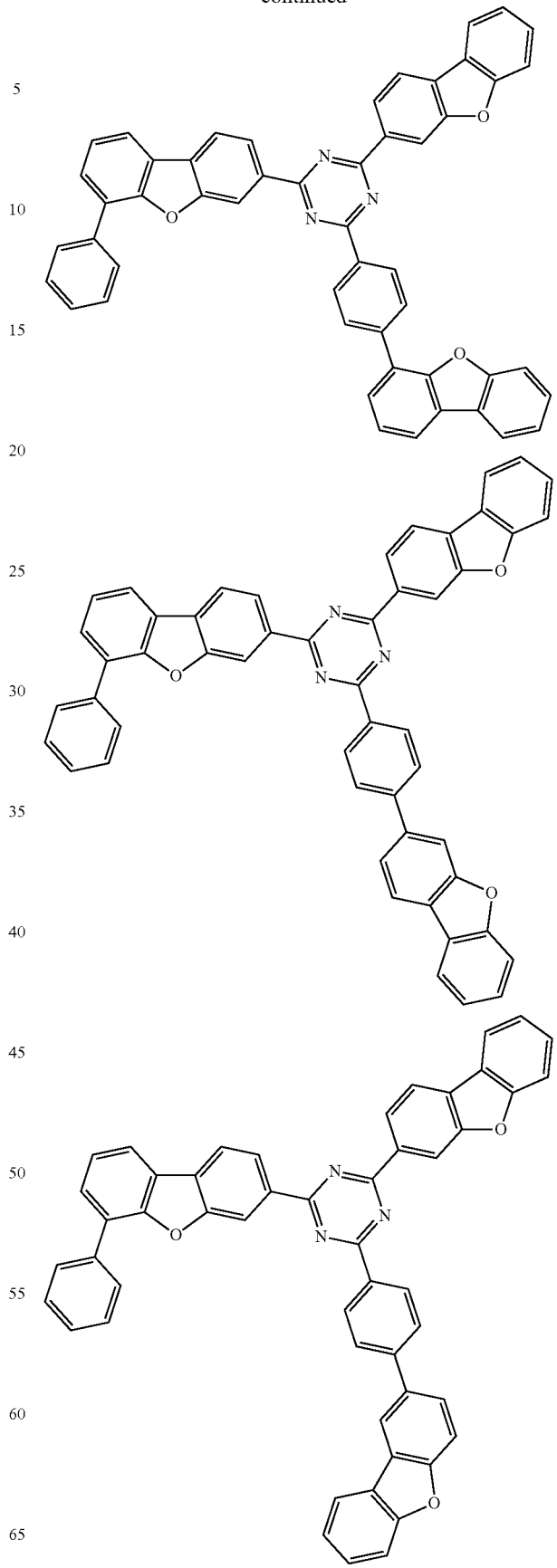

87
-continued

88
-continued

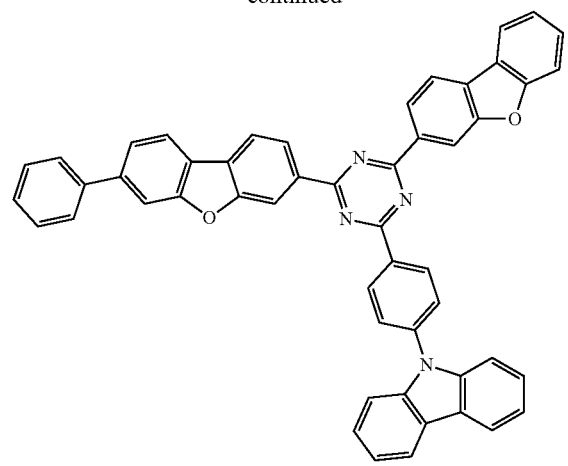
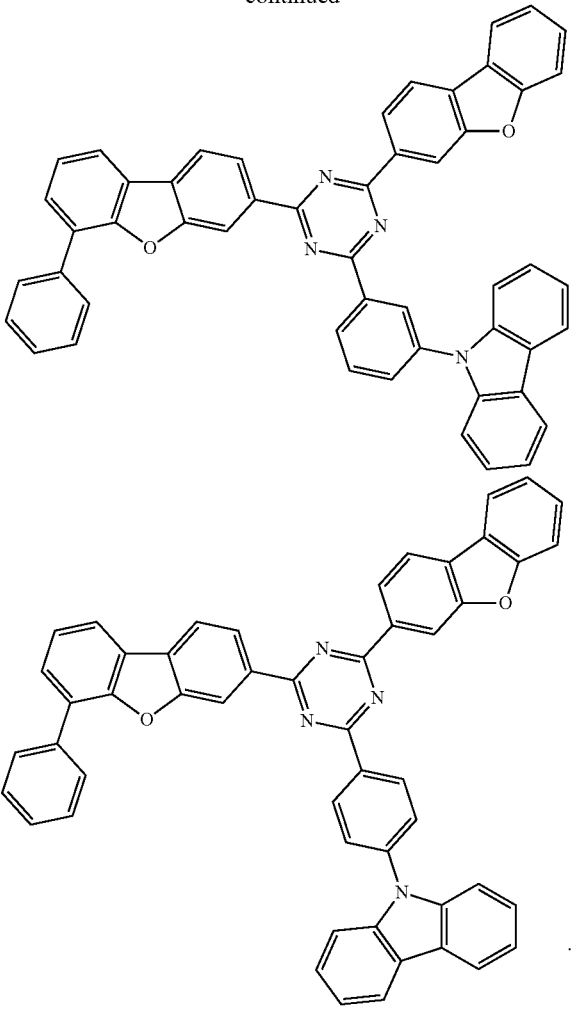
8. An organic light emitting device comprising: a first electrode; a second electrode that is provided to face the first electrode; and one or more organic material layers that are provided between the first electrode and the second electrode, wherein one or more layers of the organic material layers include a compound of claim 1.
* * * * *